US012692556B2

(12) United States Patent
Si et al.

(10) Patent No.: US 12,692,556 B2
(45) Date of Patent: Jul. 28, 2026

(54) **LOW-DENSITY LIQUID-PHASE CHIP FOR *GOSSYPIUM HIRSUTUM* L. BASED ON TARGETED CAPTURE SEQUENCING AND USE THEREOF**

(71) Applicant: ZHEJIANG UNIVERSITY, Hangzhou (CN)

(72) Inventors: Zhanfeng Si, Hangzhou (CN); Yan Hu, Hangzhou (CN); Tianzhen Zhang, Hangzhou (CN); Lei Fang, Hangzhou (CN); Zegang Han, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 19/023,226

(22) Filed: Jan. 15, 2025

(65) Prior Publication Data

US 2025/0215514 A1     Jul. 3, 2025

Related U.S. Application Data

(63) Continuation of application No. PCT/CN2024/099474, filed on Jun. 17, 2024.

(30) Foreign Application Priority Data

Jun. 27, 2023     (CN) .......................... 202310765880.0

(51) Int. Cl.
| | |
|---|---|
| *C12Q 1/68* | (2018.01) |
| *C12Q 1/6874* | (2018.01) |
| *C12Q 1/6895* | (2018.01) |

(52) U.S. Cl.
CPC ......... *C12Q 1/6895* (2013.01); *C12Q 1/6874* (2013.01); *C12Q 2600/13* (2013.01)

(58) Field of Classification Search
CPC .............................. C12Q 1/68; C12Q 2600/13
See application file for complete search history.

(56) References Cited

U.S. PATENT DOCUMENTS

2025/0215514 A1*   7/2025   Si .......................... C12Q 1/6874

FOREIGN PATENT DOCUMENTS

| CN | 105349537 A | 2/2016 | | |
|---|---|---|---|---|
| CN | 108779459 A | 11/2018 | | |
| CN | 113308562 A | 8/2021 | | |
| CN | 116751886 A * | 9/2023 | ........... | C12Q 1/6895 |
| WO | WO-2018085971 A1 * | 5/2018 | .............. | C12N 15/11 |
| WO | WO-2025001891 A1 * | 1/2025 | ........... | C12Q 1/6895 |

OTHER PUBLICATIONS

Cai et al., 2017. High-density 80K SNP array is a powerful tool for genotyping G. hirsutum accessions and genome analysis. BMC genomics, 18(1), 654, pp. 1-14. (Year: 2017).*

Chen et al., Nov. 3, 2022. Identification of elite fiber quality loci in upland cotton based on the genotyping-by-target-sequencing technology. Frontiers in plant science, 13, 1027806, pp. 1-12. (Year: 2022).*

English Translation of CN11330656A, pub. Aug. 27, 2021, pp. 1-4 (Year: 2021).*

English Translation of CN11330656B, pub. Aug. 23, 2022, pp. 1-4 (Year: 2022).*

English Translation of CN116751886A, pub. Sep. 15, 2023, pp. 1-6 (Year: 2023).*

English Translation of WO2018-085971A1, pub. May 17, 2018 (Year: 2018).*

Fang et al., 2017. Genomic analyses in cotton identify signatures of selection and loci associated with fiber quality and yield traits. Nature genetics, 49(7), pp. 1089-1098. (Year: 2017).*

Guo et al., 2019. Development of multiple SNP marker panels affordable to breeders through genotyping by target sequencing (GBTS) in maize. Molecular Breeding, 39(3)37, pp. 1-12. (Year: 2019).*

Hu et al., 2019. Gossypium barbadense and Gossypium hirsutum genomes provide insights into the origin and evolution of allotetraploid cotton. Nature genetics, 51(4), pp. 739-748. (Year: 2019).*

Hulse-Kemp et al., 2015. Development of a 63K SNP array for cotton and high-density mapping of intraspecific and interspecific populations of *Gossypium* spp. G3: Genes, Genomes, Genetics, 5(6), pp. 1187-1209. (Year: 2015).*

Si et al., Epub. Sep. 12, 2022. The design, validation, and utility of the "ZJU CottonSNP40K" liquid chip through genotyping by target sequencing. Industrial Crops and Products, 188, 115629, pp. 1-8. (Year: 2022).*

Song et al., Aug. 5, 2021. Genome-wide association analysis reveals loci and candidate genes involved in fiber quality traits under multiple field environments in cotton (*Gossypium hirsutum*). Frontiers in Plant Science, 12, 695503, pp. 1-14. (Year: 2021).*

Su et al., 2020. Genome-wide association analysis reveals loci and candidate genes involved in fiber quality traits in sea island cotton (*Gossypium barbadense*). BMC plant biology, 20(1), 289, pp. 1-. (Year: 2020).*

Yang et al., Epub. Mar. 29, 2023. Development of SNP marker panels for genotyping by target sequencing (GBTS) and its application in soybean. Molecular Breeding, 43(4), 26, pp. 1-11. (Year: 2023).*

International Search Report (PCT/CN2024/099474); Date of Mailing: Sep. 11, 2024 (10 pages).

Chinese Office Action mailed Jul. 30, 2025, issued in related Chinese Application No. 202310765880.0, 9 pages.

* cited by examiner

*Primary Examiner* — Gary Benzion
*Assistant Examiner* — Olayinka A Oyeyemi
(74) *Attorney, Agent, or Firm* — Wiersch Law Group

(57)     ABSTRACT

A low-density liquid-phase chip for *Gossypium hirsutum* L. based on targeted capture sequencing and use thereof provided. The low-density chip includes 908 SNP loci, where among the 908 SNP loci, 329 loci are significantly related to important agronomic traits, such as fiber quality, yield, and disease resistance of *Gossypium hirsutum* L., 14 loci are common plant transgenic detection loci, and 565 loci are other loci. This chip is adapted for use of detection of transgenic components in *Gossypium hirsutum* L. varieties, resource evaluation and lineage identification, seed purity identification, and genetic improvement of major agronomic traits of *Gossypium hirsutum* L. varieties.

2 Claims, 2 Drawing Sheets

Specification includes a Sequence Listing.

SEQUENCE LISTING

```
Sequence total quantity: 28
SEQ ID NO: 1              moltype = DNA   length = 302
FEATURE                  Location/Qualifiers
source                   1..302
                         mol_type = other DNA
                         organism = synthetic construct
SEQUENCE: 1
gaaggtttct agcaatctct accaaatcta tgcagagagc ttcagagagt gggaagccga   60
tcctactaac ccagctctcc gcgaggaaat gcgtattcaa ttcaacgaca tgaacagcgc  120
cttgaccaca gctatcccat tgttcgcagt ccagaactac caagttcctc tcttgtccgt  180
gtacgttcaa gcagctaatc ttcacctcag cgtgcttcga gacgttagcg tgtttgggca  240
aaggtgggga ttcgatgctg caaccatcaa tagccgttac aacgacctta ctaggctgat  300
cg                                                                  302

SEQ ID NO: 2              moltype = DNA   length = 243
FEATURE                  Location/Qualifiers
source                   1..243
                         mol_type = other DNA
                         organism = synthetic construct
SEQUENCE: 2
gatctgaacc acctcggaag taatcatcat gatgactcaa gcgatgaacc ttctgagtct   60
tcagaaccat gctgcgattc atgcatctgc actaaatcaa tacctcctca atgccattgt  120
acagatatca ggttgaattc gtgtcactcg gcttgcaaat cctgcatgtg tacacgatca  180
atgccaggca agtgtcgttg ccttgacatt gctgatttct gttacaaacc ttgcaagtcc  240
agg                                                                 243

SEQ ID NO: 3              moltype = DNA   length = 333
FEATURE                  Location/Qualifiers
source                   1..333
                         mol_type = other DNA
                         organism = synthetic construct
modified_base            14
                         mod_base = i
SEQUENCE: 3
acggtgaccg tcttcccgtt accntgcgcg ggccgaagac gccgacgccg atcacctacc   60
gcgtgccgat ggcctccgca caggtgaagt ccgccgtgct gctcgccggc ctcaacacgc  120
ccggcatcac gacggtcatc gagccgatca tgacgcgcga tcatacggaa aagatgctgc  180
agggctttgg cgccaacctt accgtcgaga cggatgcgga cggcgtgcgc accatccgcc  240
tggaaggccg cggcaagctc accggccaag tcatcgacgt gccgggcgac ccgtcctcga  300
cggccttccc gctggttgcg gccctgcttg ttc                                333

SEQ ID NO: 4              moltype = DNA   length = 333
FEATURE                  Location/Qualifiers
source                   1..333
                         mol_type = other DNA
                         organism = synthetic construct
SEQUENCE: 4
acggtgatcg tcttccagtt accttgcgtg gaccaaagac tccaacgcca atcacctaca   60
gggtacctat ggcttccgct caagtgaagt ccgctgttct gcttgctggt ctcaacaccc  120
caggtatcac cactgttatc gagccaatca tgactcgtga ccacactgaa aagatgcttc  180
aaggtttttg tgctaacctt accgttgaga ctgatgctga cggtgtgcgt accatccgtc  240
ttgaaggtcg tggtaagctc accggtcaag tgattgatgt tccaggtgat ccatcctcta  300
```

-continued

```
ctgctttccc attggttgct gccttgcttg ttc                             333

SEQ ID NO: 5          moltype = DNA  length = 262
FEATURE               Location/Qualifiers
source                1..262
                      mol_type = other DNA
                      organism = synthetic construct
SEQUENCE: 5
gaaggcacgc aacgcctacg actggacggc cgagtcgacc gtgtacgtct cccccccgcca  60
ccagcggacg ggactgggct ccacgctcta cacccacctg ctgaagtccc tggaggcaca  120
gggcttcaag agcgtggtcg ctgtcatcgg gctgcccaac gacccgagcg tgcgcatgca  180
cgaggcgctc ggatatgccc cccgcggcat gctgcgggcg gccggcttca agcacgggaa  240
ctggcatgac gtgggtttct gg                                          262

SEQ ID NO: 6          moltype = DNA  length = 263
FEATURE               Location/Qualifiers
source                1..263
                      mol_type = other DNA
                      organism = synthetic construct
SEQUENCE: 6
gaaggctagg aacgcttacg attcgacagt tgagagtact gtttacgtgt cacataggca  60
tcaaaggttg ggcctaggat ccacattgta cacacatttg cttaagtcta tggaggcaca  120
aggttttaag tctgtggttg ctgttatagg gccttccaaa cgatccatct gttaggttgc  180
atgaggcttt gggatacaca gcccggggta cattgcgcgc agctggatac aagcatggtg  240
gatggcatga tgttggtttt tgg                                         263

SEQ ID NO: 7          moltype = DNA  length = 1551
FEATURE               Location/Qualifiers
source                1..1551
                      mol_type = other DNA
                      organism = synthetic construct
SEQUENCE: 7
atggataagg cctacgtggc cctcctctcc ttcgcctccc tcttcttgct ccactacctc  60
gtttcccgcc gcaatggcac cgggaagggc agcaaggcca agggcgcgct gccgccaagc  120
cctccatccg ttccgttcct gggccacctc caccttgtca agcgccatt ccacgctgcg  180
ctggcacgcc tcgcggactg ccacggcccg gtcttctccc tgcggatggg agcccgcccc  240
gcagttgtgt gtgtcctcgcc ggagcacgcc aaggagtgct tcacggagca cgacgtggcc  300
ttcgccaacc ggccgcgctt tccctcgcag cagctcgcct ccttcaacgg tgccgcgctg  360
ggttccgcca gctacggccc gtactggcgc aacctccgcc gcgtcgccac cgtccacctc  420
ctgtccgcgc accgcgtcgc gtgcatgacg gggactatcg cggccgaggt gcgggccatg  480
gtgcgacgga tgaaccgcgc cgcgcaggtg gcatcaggcg gcgcggcgcg catcgagctc  540
aagcggaggc tatttgaggt ctcgctcagc gtgcttatgg agaccatcgc gcggaccaag  600
acgtcacgta cggaggcgga cgacgacacg gacatgtcgc ctgaggcccg ggagttcaac  660
cagatcgtgg atgagctcct gcctcacctc ggcacggcta acttgtggga ctacatgccg  720
gtgttgcggt ggttcgacgt gttcggcgtg aggaagaaga tcgtgtccgc ggtgaggaga  780
agggacgcgt tcctgcggca tcttgtcgac gcagagagga cgaggctgga cgacggcaac  840
gatgcgggcg agaagaagag catcattgct atgctgctca ctctgcagaa gtcagagccg  900
gacgtctact cggataccat gatcatggct ctatgtggga acttgtttgg ggccggcaca  960
gagaccacgt cgacgaccac cgaatgggcc atgtctctcc tcctcaacca cccggagaag  1020
ctcaggaagg cgcaggctga gatcgatgct gtcgtgggca catcccgcct tcttaccgcc  1080
gacgacatgc ctcgtctcac ctacctccgc tgcatcatcg acgagaccat gcgcctgtac  1140
ccggccgcac cacttctgct gccacacgag tcctcgacac actgcaaggt cggcggctac  1200
gacgtgcccg ccggcacgat gctgctcgtc aacgtgtacg ccatccacag ggaccccgcg  1260
gtgtgggacg ggccgaccga gttcgtgccg gagcggttcg aggatggcaa ggcagaaggc  1320
cggctgctga tgccgttcgg gatgggacgg cgcaagtgtc ccggcgagac gctccgcgctg  1380
cggacgatcg ggctggtgct cggcacgctg atccagtgtt tcgactggga ccgggttgat  1440
ggtcttgagg tcgacatgac tgaaagtggt gggctcacga tccccagggc tgtcccgttg  1500
gaggccatgt gcaggcctcg tgcgacgatg cgtgaggttt tgcaggagct c          1551

SEQ ID NO: 8          moltype = DNA  length = 1590
FEATURE               Location/Qualifiers
source                1..1590
                      mol_type = other DNA
                      organism = synthetic construct
SEQUENCE: 8
atggcggcga ccatggcgtc caacgctgcg gctgcggctg cggtgtccct ggaccaggcc  60
gtggctgcgt cggcagcgtt ctcgtcgcgg aagcagctgc ggctgcctgc cgcagcgcgc  120
ggaggggatgc gggtgcgggt gcgggcgcgg ggtcggcggg aggcggtggt ggtggcgtcc  180
gcgtcgtcgt cgtcggtggc agcgccggcg gcgaaggctg agatggctaca cggtgcaagc  240
agccggccgg caaccgctcg caaatcttcc ggcctttcgg gaacggtcag gattccgggc  300
gataagtcca tatcccaccg gtcgttcatg ttcggcggtc ttgccagcgg tgagacgcgc  360
atcacgggcc tgcttgaagg tgaggacgtg atcaataccg ggaaggccat gcaggctatg  420
ggagcgcgta tccgcaagga aggtgacaca tggatcattg acgcgttgg gaatggcggt  480
ctgctcgccc ctgaggcccc tctcgacttc ggcaatgcgg cgaagcggct caggctcact  540
atgggactgg tcgggtgta cgacttcgat agcacgttca tcggagacgc ctcgctcaca  600
aagcgcccaa tgggccgcgt tctgaacccg ttgcgcgaga tgggcgtaca ggtcaaatcc  660
gaggatggtg accgtttgcc cgttacgctg cgcgggccga gacgcctac cccgattacc  720
taccgcgtgc caatggcatc cgcccaggtc aagtcagccg tgctcctcgc cggactgaac  780
actccgggca tcaccacggt gatcgagccc atcatgacca gggatcatac cgaaaagatg  840
```

```
cttcaggggt ttggcgccaa cctgacggtc gagacggacg ctgacggcgt caggaccatc     900
cgccttgagg gcaggggtaa actgactggc caagtcatcg atgttccggg agacccgtcg     960
tccacggcct tcccgttggt tgcggcgctg ctcgtgccgg ggagtgacgt gaccatcctg     1020
aacgtcctca tgaacccgac caggaccggc ctgatcctca cgcttcagga gatgggagcc     1080
gacatcgagg tgatcaaccc gcgcctggca ggcggtgaag acgttgcgga tctgcgcgtg     1140
cgctcctcta ccctgaaggg cgtgacggtc ccggaagatc gcgcgccgtc catgatagac     1200
gagtatccta ttctggccgt cgccgctgcg ttcgccgaag gggccacggt catgaacggt     1260
cttgaggaac tccgcgtgaa ggaatcggat cgcctgtcgg cggtggccaa tggcctgaag     1320
ctcaacggtg ttgactgcga cgagggtgag acctcactcg tggtccgtgg ccggcctgat     1380
ggcaagggcc tcggcaacgc cagtggagcg gccgtcgcca cgcacctcga tcatcgcatc     1440
gcgatgtcct tcttggtgat gggtctcgtc tcagagaacc cggtgaccgt cgatgacgcc     1500
acgatgatag cgacgagctt cccagagttc atggatctga tggcgggcct cggggccaag     1560
atcgaactgt ctgacacgaa ggccgcttga                                     1590

SEQ ID NO: 9              moltype = DNA   length = 195
FEATURE                  Location/Qualifiers
source                   1..195
                         mol_type = other DNA
                         organism = synthetic construct
SEQUENCE: 9
gctcctacaa atgccatcat tgcgataaag gaaaggctat cattcaagat gcctctgccg     60
acagtggtcc caaagatgga cccccaccca cgaggagcat cgtggaaaaa gaagacgttc     120
caaccacgtc ttcaaagcaa gtggattgat gtgatacttc cactgacgta agggatgacg     180
cacaatccca ctatc                                                     195

SEQ ID NO: 10             moltype = DNA   length = 210
FEATURE                  Location/Qualifiers
source                   1..210
                         mol_type = other DNA
                         organism = synthetic construct
SEQUENCE: 10
aagacatcca ccgaagactt aaagttagtg ggcatctttg aaagtaatct tgtcaacatc     60
gagcagctgg cttgtgggga ccagacaaaa aaggaatggt gcagaattgt taggcgcacc     120
taccaaaagc atctttgcat ttattgcaaa gataaagcag attcctctag tacaagtggg     180
gaacaaaata acgtggaaaa gagctgtcct                                     210

SEQ ID NO: 11             moltype = DNA   length = 183
FEATURE                  Location/Qualifiers
source                   1..183
                         mol_type = other DNA
                         organism = synthetic construct
SEQUENCE: 11
gccgttttac gtttggaact gacagaaccg caacgttgaa ggagccactc agccgcgggt     60
ttctggagtt taatgagcta agcacatacg tcagaaacca ttattgcgcg ttcaaaagtc     120
gcctaaggtc actatcagct agcaaatatt tcttgtcaaa aatgctccac tgacgttcca     180
taa                                                                  183

SEQ ID NO: 12             moltype = DNA   length = 217
FEATURE                  Location/Qualifiers
source                   1..217
                         mol_type = other DNA
                         organism = synthetic construct
modified_base            78
                         mod_base = i
modified_base            114
                         mod_base = i
SEQUENCE: 12
atcgttcaaa catttggcaa taaagtttct taagattgaa tcctgttgcc ggtcttgcga     60
tgattatcat attaattnct gttgaattac gttaagcatg taataattaa catngtaatc     120
catgacgtta tttatgagat gggttttat gattagagtc ccgcaattat acatttaata     180
cgcgatagaa aacaatatag cgcgcaaact aggataa                            217

SEQ ID NO: 13             moltype = DNA   length = 121
FEATURE                  Location/Qualifiers
source                   1..121
                         mol_type = other DNA
                         organism = synthetic construct
SEQUENCE: 13
gtttcgctca tgtgttgagc gtataagaaa cccttagtat gtatttgtat ttgtaaaata     60
cttctatcaa taaaatttct aattcctaaa accaaaatcc agtactaaaa tccagatccc     120
c                                                                    121

SEQ ID NO: 14             moltype = DNA   length = 795
FEATURE                  Location/Qualifiers
source                   1..795
                         mol_type = other DNA
                         organism = synthetic construct
SEQUENCE: 14
atgattgaac aagatggatt gcacgcaggt tctccggccg cttgggtgga gaggctattc     60
```

-continued

```
ggctatgact gggcacaaca gacaatcggc tgctctgatg ccgccgtgtt ccggctgtca    120
gcgcagggc gcccggttct ttttgtcaag accgacctgt ccggtgccct gaatgaactg     180
caggacgagg cagcgcggct atcgtggctg gccacgacgg gcgttccttg cgcagctgtg    240
ctcgacgttg tcactgaagc gggaagggac tggctgctat tgggcgaagt gccggggcag    300
gatctcctgt catctcacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgcg catgcccgac    540
ggcgatgatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                     795
```

```
SEQ ID NO: 15         moltype = DNA   length = 302
FEATURE               Location/Qualifiers
source                1..302
                      mol_type = other DNA
                      organism = synthetic construct
SEQUENCE: 15
gaaggtttct agcaatctct accaaatcta tgcagagagc ttcagagagt gggaagccga     60
tcctactaac ccagctctcc gcgaggaaat gcgtattcaa cggaacagcgc tgaacagcgc   120
cttgaccaca gctatcccat tgttcgcagt ccagaactac caagttcctc tcttgtccgt    180
gtacgttcaa gcagctaatc ttcacctcag cgtgcttcga gacgttagcg tgtttgggca    240
aaggtgggga ttcgatgctg caaccatcaa tagccgttac aacgacctta ctaggctgat    300
cg                                                                    302
```

```
SEQ ID NO: 16         moltype = DNA   length = 243
FEATURE               Location/Qualifiers
source                1..243
                      mol_type = other DNA
                      organism = synthetic construct
SEQUENCE: 16
gatctgaacc acctcggaag taatcatcat gatgactcaa gcgatgaacc ttctgagtct     60
tcagaaccat gctgcgattc atgcatctgc actaaatcaa tacctcctca atgccattgt    120
acagatatca ggttgaattc gtgtcactcg gcttgcaaat cctgcatgtg tacacgatca    180
atgccaggca agtgtcgttg ccttgacatt gctgatttct gttacaaacc ttgcaagtcc    240
agg                                                                   243
```

```
SEQ ID NO: 17         moltype = DNA   length = 333
FEATURE               Location/Qualifiers
source                1..333
                      mol_type = other DNA
                      organism = synthetic construct
modified_base         14
                      mod_base = i
SEQUENCE: 17
acggtgaccg tcttcccgtt accntgcgcg ggccgaagac gccgacgccg atcacctacc     60
gcgtgccgat ggcctccgca caggtgaagt ccgccgtgct gctcgccggc ctcaacacgc    120
ccggcatcac gacggtcatc gagccgatca tgacgcgcga tcatacggaa aagatgctgc    180
agggctttgg cgccaacctt accgtcgaga cggatgcgga cggcgtgcgc accatccgcc    240
tggaaggccg cggcaagctc accggccaag tcatcgacgt gccgggcgac ccgtcctcga    300
cggccttccc gctggttgcg gccctgcttg ttc                                 333
```

```
SEQ ID NO: 18         moltype = DNA   length = 333
FEATURE               Location/Qualifiers
source                1..333
                      mol_type = other DNA
                      organism = synthetic construct
SEQUENCE: 18
acggtgatcg tcttccagtt accttgcgtg gaccaaagac tccaacgcca atcacctaca     60
gggtacctat ggcttccgct caagtgaagt ccgctgttct gcttgctggt ctcaacaccc    120
caggtatcac cactgttatc gagccaatca tgactcgtga ccacactgaa aagatgcttc    180
aaggttttgg tgctaacctt accgttgaga ctgatgctga cggtgtgcgt accatccgtc    240
ttgaaggtcg tggtaagctc accggtcaag tgattgatgt tccaggtgat ccatcctcta    300
ctgctttccc attggttgct gccttgcttg ttc                                 333
```

```
SEQ ID NO: 19         moltype = DNA   length = 262
FEATURE               Location/Qualifiers
source                1..262
                      mol_type = other DNA
                      organism = synthetic construct
SEQUENCE: 19
gaaggcacgc aacgcctacg actggacggc cgagtcgacc gtgtacgtct ccccccgcca     60
ccagcggacg ggactgggct ccacgctcta cacccacctg ctgaagtccc tggaggcaca    120
gggcttcaag agcgtggtcg ctgtcatcgg gctgcccaac gacccgagcg tgcgcatgca    180
cgaggcgctc ggatatgccc cccgcggcat gctgcgggcg gccggcttca agcacgggaa    240
ctggcatgac gtgggtttct gg                                              262
```

```
SEQ ID NO: 20              moltype = DNA   length = 263
FEATURE                    Location/Qualifiers
source                     1..263
                           mol_type = other DNA
                           organism = synthetic construct
SEQUENCE: 20
gaaggctagg aacgcttacg attcgacagt tgagagtact gtttacgtgt cacataggca    60
tcaaaggttg ggcctaggat ccacattgta cacacatttg cttaagtcta tggaggcgca   120
aggtttttaag tctgtggttg ctgttatagg gccttccaaa cgatccatct gttaggttgc   180
atgaggcttt gggatacaca gcccggggta cattgcgcgc agctggatac aagcatggtg   240
gatggcatga tgttggtttt tgg                                           263

SEQ ID NO: 21              moltype = DNA   length = 1551
FEATURE                    Location/Qualifiers
source                     1..1551
                           mol_type = other DNA
                           organism = synthetic construct
SEQUENCE: 21
atggataagg cctacgtggc cctcctctcc ttcgcctccc tcttcttgct ccactacctc    60
gtttccgcc gcaatggcac cgggaagggc agcaaggcca agggcgcgct gccgccaagc   120
cctccatccg ttccgttcct gggccacctc caccttgtca agacgccatt ccacgctgcg   180
ctggcacgcc tcgcggactg ccacggcccg gtcttctccc tcggatggg agcccgcccc   240
gcagttgtgg tgtcctcgcc ggagcacgcc aaggagtgct tcacggagca cgacgtggcc   300
ttcgccaacc ggccgcgctt tccctcgcag cagctcgcct ccttcaacgg tgccgcgctg   360
ggttccgcca gctacggccc gtactggcgc aacctccgcc gcgtcgccac cgtccacctc   420
ctgtccgcgc accgcgtcgc gtgcatgacg gggactatcg cggcgaggt gcggccatg   480
gtgcgacgga tgaaccgcgc cgcgcaggtg gcatcaggcg gcgcggcgcg catcgagctc   540
aagcggaggc tatttgaggt ctcgctcagc gtgcttatgg agaccatcgc gcggaccaag   600
acgtcacgta cggaggcgga cgacgacacg gacatgtcgc ctgaggcccg ggagttcaag   660
cagatcgtgg atgagctcct gcctcacctc ggcacggcta acttgtggga ctacatgccg   720
gtgttgcggt ggttcgacgt gttcggcgtg aggaagaaga tcgtgtccgc ggtgaggaga   780
agggacgcgt tcctgcggca tcttgtcgac gcagagagga cgaggctgga cgacggcaac   840
gatgcgggcg agaagaagag catcattgct atgctgctca ctctgcagaa gtcagagccg   900
gacgtctact cggataccat gatcatggct ctatgtggga acttgtttgg ggccggcaca   960
gagaccacgt cgacgaccac cgaatgggcc atgtctctcc tcctcaacca cccggagaag  1020
ctcaggaagg cgcaggctga gatcgatgct gtcgtgggca catcccgcct tcttaccgcc  1080
gacgacatgc tcgtctcac ctacctccgc tgcatcatcg acgagaccat gcgcctgtac  1140
ccggccgcac cacttctgct gccacacgag tcctcgacac actgcaaggt cggcggctac  1200
gacgtgcccg ccggcacgat gctgctcgtc aacgtgtacg ccatccacag ggaccccgcg  1260
gtgtgggacg ggccgaccga gttcgtgccg gagcggttcg aggatggcaa ggcagaaggc  1320
cggctgctga tgccgttcgg gatgggacgg cgcaagtgtc ccggcgagac gctcgcgctg  1380
cggacgatcg ggctggtgct cggcacgctg atccagtgtt tcgactggga ccgggttgat  1440
ggtcttgagg tcgacatgac tgaaagtggt gggctcacga tccccagggc tgtcccgttg  1500
gaggccatgt gcaggcctcg tgcgacgatg cgtgaggttt tgcaggagct c           1551

SEQ ID NO: 22              moltype = DNA   length = 1590
FEATURE                    Location/Qualifiers
source                     1..1590
                           mol_type = other DNA
                           organism = synthetic construct
SEQUENCE: 22
atggcggcga ccatggcgtc caacgctgcg gctcgcggctg cggtgtccct ggaccaggcc    60
gtggctgcgt cggcagcgtt ctcgtcgcgg aagcagctgc ggctgcctgc cgcagcgcgc   120
ggagggatgc gggtgcgggt gcgggcgcgg ggtcggcggg aggcggtggt ggtggcgtcc   180
gcgtcgtcgt cgtcggtggc agcgccggcg gcgaaggctg agatgctaca cggtgcaagc   240
agccggccgg caaccgctcg caaatcttcc ggcctttcgg gaacggtcag gattccgggc   300
gataagtcca tatcccaccg gtcgttcatg ttcggcggtc ttgccagcgg tgagacgcgc   360
atcacgggcc tgcttgaagg tgaggacgtg atcaataccg ggaaggccat gcaggctatg   420
ggagcgcgta tccgcaagga aggtgacaca tggatcattg acgcgttgg gaatggcggt   480
ctgctcgccc ctgaggcccc tctcgacttc ggcaatgcgg cgacgggctg caggctcact   540
atgggactgg tcgggtgta cgacttcgat agcacgttca tcggagacgc ctcgctcaca   600
aagcgcccaa tgggccgcgt tctgaacccg ttgcgcgaga tgggcgtaca ggtcaaatcc   660
gaggatggtg accgtttgcc cgttacgctg cgcgggccga agacgcctac cccgattacc   720
taccgcgtgc caatggcatc cgcccaggtc aagtcagccg tgctcctcgc ggactgaac   780
actccgggca tcaccacggt gatcgagccc atcatgacca gggatcatac cgaaaagatg   840
cttcaggggt ttggcgccaa cctgacggtc gagacggacg ctgacggcgt caggaccatc   900
cgccttgagg gcaggggtaa actgactggc caagtcatcg atgttccggg agaccgtcg   960
tccacggcct tcccgttggt tgcggcgctg ctcgtgccgg ggagtgacgt gaccatcgtg  1020
aacgtcctca tgaacccgac caggaccggc ctgatcctca cgcttcagga gatgggagcc  1080
gacatcgagg tgatcaaccc gcgcctggca ggcggtgaag acgttgcgga tctgcgcgtg  1140
cgctcctcta ccctgaaggg cgtgacggtc ccggaagatc gcgcgccgtc catgatagac  1200
gagtatccta ttctggccgt cgccgctgcg ttcgccgaag gggccacggt catgaacggt  1260
cttgaggaac tccgcgtgaa ggaatcggat cgcctgtcgg cggtggccaa tggcctgaag  1320
ctcaacgtgg ttgactgcga cgagggtgag acctcactcg tggtccgtgg ccggcctgat  1380
ggcaagggcc tcgccaacgc cagtggagcg gccgtcgcca cgcacctcga tcatcgcatc  1440
gcgatgtcct tcttggtgat gggtctcgtc tcagagaacc cggtgaccgt cgatgacgcc  1500
acgatgatag cgacgagctt cccagagttc atggatctga tggcgggcct cggggccaag  1560
atcgaactgt ctgacacgaa ggccgcttga                                   1590
```

-continued

```
SEQ ID NO: 23          moltype = DNA   length = 195
FEATURE                Location/Qualifiers
source                 1..195
                       mol_type = other DNA
                       organism = synthetic construct
SEQUENCE: 23
gctcctacaa atgccatcat tgcgataaag gaaaggctat cattcaagat gcctctgccg   60
acagtggtcc caaagatgga cccccaccca cgaggagcat cgtggaaaaa gaagacgttc   120
caaccacgtc ttcaaagcaa gtggattgat gtgatacttc cactgacgta agggatgacg   180
cacaatccca ctatc                                                    195

SEQ ID NO: 24          moltype = DNA   length = 210
FEATURE                Location/Qualifiers
source                 1..210
                       mol_type = other DNA
                       organism = synthetic construct
SEQUENCE: 24
aagacatcca ccgaagactt aaagttagtg ggcatctttg aaagtaatct tgtcaacatc   60
gagcagctgg cttgtgggga ccagacaaaa aaggaatggt gcagaattgt taggcgcacc   120
taccaaaagc atctttgcat ttattgcaaa gataaagcag attcctctag tacaagtggg   180
gaacaaaata acgtggaaaa gagctgtcct                                    210

SEQ ID NO: 25          moltype = DNA   length = 183
FEATURE                Location/Qualifiers
source                 1..183
                       mol_type = other DNA
                       organism = synthetic construct
SEQUENCE: 25
gccgttttac gtttggaact gacagaaccg caacgttgaa ggagccactc agccgcgggt   60
ttctggagtt taatgagcta agcacatacg tcagaaacca ttattgcgcg ttcaaaagtc   120
gcctaaggtc actatcagct agcaaatatt tcttgtcaaa aatgctccac tgacgttcca   180
taa                                                                 183

SEQ ID NO: 26          moltype = DNA   length = 217
FEATURE                Location/Qualifiers
source                 1..217
                       mol_type = other DNA
                       organism = synthetic construct
modified_base          78
                       mod_base = i
modified_base          114
                       mod_base = i
SEQUENCE: 26
atcgttcaaa catttggcaa taaagtttct taagattgaa tcctgttgcc ggtcttgcga   60
tgattatcat attaattnct gttgaattac gttaagcatg taataattaa catngtaatc   120
catgacgtta tttatgagat gggttttat gattagagtc ccgcaattat acatttaata   180
cgcgatagaa aacaatatag cgcgcaaact aggataa                            217

SEQ ID NO: 27          moltype = DNA   length = 121
FEATURE                Location/Qualifiers
source                 1..121
                       mol_type = other DNA
                       organism = synthetic construct
SEQUENCE: 27
gtttcgctca tgtgttgagc gtataagaaa cccttagtat gtatttgtat ttgtaaaata   60
cttctatcaa taaaatttct aattcctaaa accaaaatcc agtactaaaa tccagatccc   120
c                                                                   121

SEQ ID NO: 28          moltype = DNA   length = 795
FEATURE                Location/Qualifiers
source                 1..795
                       mol_type = other DNA
                       organism = synthetic construct
SEQUENCE: 28
atgattgaac aagatggatt gcacgcaggt tctccggccg cttgggtgga gaggctattc   60
ggctatgact gggcacaaca gacaatcggc tgctctgatg ccgccgtgtt ccggctgtca   120
gcgcagggc gcccggttct ttttgtcaag accgacctgt ccggtgccct gaatgaactg   180
caggacgagg cagcgcggct atcgtggctg gccacgacgg gcgttccttg cgcagctgtg   240
ctcgacgttg tcactgaagc gggaagggac tggctgctat tgggcgaagt gccggggcag   300
gatctcctgt catctcacct tgctcctgcc gagaaagtat ccatcatggc tgatgcaatg   360
cggcggctgc atacgcttga tccggctacc tgcccattcg accaccaagc gaaacatcgc   420
atcgagcgag cacgtactcg gatggaagcc ggtcttgtcg atcaggatga tctggacgaa   480
gagcatcagg ggctcgcgcc agccgaactg ttcgccaggc tcaaggcgcg catgcccgac   540
ggcgatgatc tcgtcgtgac ccatggcgat gcctgcttgc cgaatatcat ggtggaaaat   600
ggccgctttt ctggattcat cgactgtggc cggctgggtg tggcggaccg ctatcaggac   660
atagcgttgg ctacccgtga tattgctgaa gagcttggcg gcgaatgggc tgaccgcttc   720
ctcgtgcttt acggtatcgc cgctcccgat tcgcagcgca tcgccttcta tcgccttctt   780
gacgagttct tctga                                                    795
```

LOW-DENSITY LIQUID-PHASE CHIP FOR *GOSSYPIUM HIRSUTUM* L. BASED ON TARGETED CAPTURE SEQUENCING AND USE THEREOF

CROSS-REFERENCE TO RELATED APPLICATIONS

The present application is a Continuation Application (CON) of International Application No. PCT/CN2024/099474 filed on Jun. 17, 2024, which claims a priority to Chinese Patent Application No. 2023107658800, filed on Jun. 27, 2023, both of which are hereby incorporated by reference in their entireties.

REFERENCE TO SEQUENCE LISTING

The present application is being filed along with a Sequence Listing in electronic format. The Sequence Listing is provided as a file entitled with "DF242868US-Sequence Listing ST.26", and created on Jan. 9, 2025, which is approximately 20.3 KB in size. The "DF242868US-Sequence Listing ST.26" is replaced with a revised Sequence Listing of "DF242868US-Sequence Listing ST.26-2ed", created on Mar. 21, 2025, which is approximately 20.3 KB in size. And the "DF242868US-Sequence Listing ST.26-2ed" is replaced with a revised Sequence Listing of "DF242868US-Sequence Listing ST.26-3rd", created on Nov. 24, 2025, which is approximately 39.6 KB in size. The information in the electronic format of the "DF242868US-Sequence Listing ST.26-3rd" is incorporated herein by reference in its entirety.

TECHNICAL FIELD

The present disclosure relates to the fields of genetics, molecular biology, bioinformatics and cotton molecular breeding, in particular to a Low-density liquid-phase chip for *Gossypium hirsutum* L. based on targeted capture sequencing and use thereof.

BACKGROUND

Single Nucleotide Polymorphism (SNP) refers to the variation of a single nucleotide in a genome, which is a variation form formed by substitution, transversion, insertion or deletion of a single nucleotide pair. As the third generation genetic marker, single nucleotide polymorphism is an ideal genotyping target because of a large number of SNPs, dense distribution and easy detection. In view of the innovation of molecular marker technology, single nucleotide polymorphism (SNP) based on DNA sequence variation is close to the ultimate standard for mutation detection at the molecular level. It is expected that the development of molecular detection technology and platform in the next few years will be promoted and improved on this basis. Therefore, efficient and low-cost SNP genotyping technology has become the best choice for developing sharing technology and platform.

Genotyping by target sequencing (GBTS) technology based on SNP is to select specific target loci from genomic DNAs for sequencing and genotyping. This targeted or fixed simplified genome sequencing greatly reduces the amount of DNA sequencing, simplifies biological information analysis and data processing, and improves the adaptability to various genotyping platforms. Moreover, this technique is adapted for the detection of all marker loci, including known loci (such as cloned genes), functionally unknown loci (candidate genes) and neutral loci. The flexibility of the number of systematic markers provides a huge elastic space for various applications, which is basically adapted for all scenarios requiring different numbers of markers, including e.g., marker-assisted major gene selection, backcross breeding and its background selection, polygenic polymerization breeding, seed purity detection, transgenic component identification and the like. Therefore, GBTS will be the first choice for genotyping for a long time to come.

Cotton SNP chips, such as Illumina 80K and ZJU40K, that have been developed have been widely used by breeding enterprises and scientific research units for genotyping, genome selection and genetic diversity analysis of germplasm resources. The SNP density of these chips is generally high, and the Illumina 80K solid-phase chip still has the disadvantage of being unable to be customized. The design of chip loci is generally based on the evenly distributed loci in the whole genome, without considering the correlation with traits, therefore the typing cost is high and the purposiveness of selection is not strong. Traditional breeding has a long cycle and unpredictable phenotypic variation, which mainly depends on the experience of breeders. Other excellent traits may be easily lost when improving the breeding target traits. Molecular marker-assisted breeding is to use the characteristics of close linkage between molecular markers and genes that determine target traits. By detecting molecular markers, the target genes and loci are detected to achieve the purpose of selecting target traits which has the advantages of rapidness, accuracy and no interference from environmental conditions, with its key limiting factor being the accurate identification of loci associated with traits.

To sum up, it is urgent to develop a low-density liquid-phase SNP chip for *Gossypium hirsutum* L. genotyping, transgenic detection, germplasm resource evaluation and molecular marker-assisted selection based on the loci significantly correlated with *Gossypium hirsutum* L. fiber quality, yield, disease resistance and other important agronomic traits excavated by genome sequencing and genome-wide association study of *Gossypium hirsutum* L.

SUMMARY

In view of the shortcomings of the prior art, it is an object of the present disclosure to find and screen 894 SNP loci, and develop a liquid-phase gene chip by using the 894 SNP loci and 14 major transgenes of *Gossypium hirsutum* L. for detecting transgenic components and genotyping of *Gossypium hirsutum* L.

The technical solution adopted by the present disclosure is as follows:

the present disclosure relates to a Low-density liquid-phase chip for *Gossypium hirsutum* L. based on targeted capture sequencing. A whole genome low-density SNP chip of *Gossypium hirsutum* L. consists of probes for detecting 894 SNP loci and 14 major transgenes; the 14 major transgenes comprise: A1Bt, referring to *Bacillus thuringiensis* gene, which comprises nucleotide sequences set forth in SEQ ID NO. 15; A2CPTI, referring to Cowpea Trypsin Inhibitor, which comprises nucleotide sequences set forth in SEQ ID NO. 16; A3CP4-epsps, referring to 5-enolpyruvylshikimate-3-phosphate synthase gene derived from *Agrobacterium* sp. Cp-4, which comprises nucleotide sequences set forth in SEQ ID NO. 17; A4CP4-epsps, referring to 5-enolpyruvylshikimate-3-phosphate synthase gene derived from *Agrobacterium* sp. Cp-4 2, which comprises nucleotide sequences set forth in SEQ ID NO. 18; A5bar, referring to bialaphos resistance gene, which comprises nucleotide sequences set forth in SEQ ID NO. 19; A6pat, referring to phosphinthricin acetyltransferase gene, which comprises nucleotide sequences set forth in SEQ ID NO. 20; A7CdP450, referring to Cytochrome P450, which comprises nucleotide sequences set forth in SEQ ID NO. 21; A8cp4-epsps, referring to 5-enolpyruvylshikimate-3-phosphate synthase gene derived from *Agrobacterium* sp. Cp-4, which comprises nucleotide sequences set forth in SEQ ID NO. 22; B.1CaMV35S, referring to 35S promoter from cauliflower mosaic virus, which comprises nucleotide sequences set forth in SEQ ID NO. 23; B.2FMV35S, referring to 35S promoter from figwort mosaic virus, which comprises nucleotide sequences set forth in SEQ ID NO. 24; B.3NOS, referring to promoter of nopaline synthase gene, which comprises nucleotide sequences set forth in SEQ ID NO. 25; B.4NOS, referring to terminator of nopaline synthase gene, which comprises nucleotide sequences set forth in SEQ ID NO. 26; B.5CaMV35S, referring to 35S terminator from the cauliflower mosaic virus, which comprises nucleotide sequences set forth in SEQ ID NO. 27; and NPTII, referring to neomycin-3'-phosphotransferase gene, which comprises nucleotide sequences set forth in SEQ ID NO. 28; the 894 SNP loci are shown in Table 1.

Further, the probes for detecting the 14 major transgenes are shown as SEQ ID NOs. 1-14.

The gene chip of that present disclosure is a liquid-phase chi, in which probes are designed based on the liquid-phase probe capture technology to synthesize a kit containing information of 908 loci based on, and can be used for detecting whether there are 14 common transgenic components in *Gossypium hirsutum* L., *Gossypium hirsutum* L. resource evaluation, lineage identification, seed purity identification and genetic improvement of major agronomic traits of *Gossypium hirsutum* L. varieties.

Further, the major agronomic traits comprise fiber quality trait, yield trait and disease resistance.

The liquid-phase chip technology system used in the present disclosure is a GenoBaits technology system. The working principle is that the probes designed based on the target SNP markers carries out complementary combination and sequencing of the target sequences with the DNA of the test sample, so as to achieve the purpose of genotyping of the target SNP marker of the test sample. In the present disclosure, all probes that can accurately detect 894 SNP loci and 14 major transgenes can achieve the same technical effect. The use of the chip can greatly improve the accuracy of genotyping, improve the detection level, reduce the detection cost, and provide important technical support for cotton molecular breeding.

DESCRIPTION OF EMBODIMENTS

The present disclosure will be further described in detail with reference to specific embodiments.

Example 1: Design and Preparation of the Low-Density Liquid-Phase Chip for *Gossypium hirsutum* L. Based on Targeted Capture Sequencing The specific method is as follows:

1. Based on VCF files obtained by resequencing three populations (Fang et al. Genomic analyses in cotton identify signatures of selection and loci associated with fiber quality and yield traits. Nature genetics, 2017, 49 (7): 1089; Liu et al. Association mapping of seed oil and protein contents in upland cotton. Euphytica, 2015, 205 (2): 637-645), and taking the cotton genome TM-1_V2.1 (Hu et al. *Gossypium barbadense* and *Gossypium hirsutum* genomes provide insights into the origin and evolution of allotetraploid cotton. Nature genetics, 2019, 51 (4): 739-748.) as a reference, 601 SNP loci (background loci) were screened according to the principles of MAF>0.35, heterozygosity rate<15%, NA ratio<10% and uniform chromosome distribution for the SNP loci in the populations.

2. According to the GWAS association results of major agronomic traits (Fang et al. Genomic analyses in cotton identify signatures of selection and loci associated with fiber quality and yield traits. Nature genetics, 2017, 49 (7): 1089; Liu et al. Association mapping of seed oil and protein contents in upland cotton. Euphytica, 2015, 205 (2): 637-645; Li et al. Genomic Insights into the Genetic Basis of Cotton Breeding in China, Molecular Plant 16, 662-677), 634 SNP loci (foreground loci) significantly related to agronomic traits and disease resistance were selected.

3. A total of 1235 target segments of *Gossypium hirsutum* L. genomes were obtained, and 1148 candidate target segments were obtained after screening by detecting whether the positions and locus genotypes of candidate SNPs were consistent with the reference genome TM-1V2.1 (cotton.zj-u.edu.cn) of *Gossypium hirsutum* L.

Figure 1:
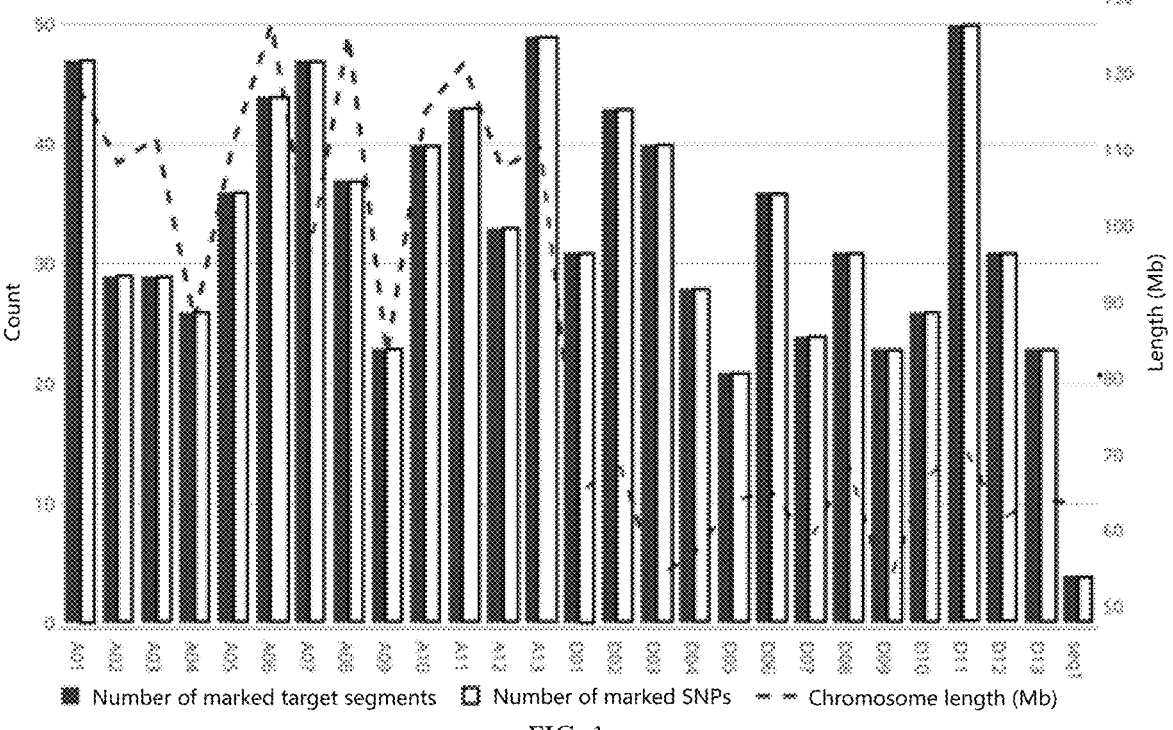
FIG. 1 is a statistical diagram of SNP marker chromosome distribution; statistical results of the number of SNP markers on different chromosomes: a. the abscissa is the chromosome number; B. the left ordinate indicates the number of loci and segments; c. the right ordinate indicates the chromosome length (Mb)
Figure 2:
FIG. 2 shows the distribution of SNP loci on chromosomes.

4. According to 1148 candidate target segments, probe design was carried out. The design principles were as follows: all probes with a length of 100-120 bp in the coverable area were selected; the GC content of the probe in the coverable target region was calculated; the number of homology regions of the probe was calculated, where the three situations, namely, a. 40 bp above being exactly the same, b. the similarity being 85% and the length being 80 bp and c. the similarity being 95% and the length being 70 bp, were regarded as a homology region. The probe selection principles were as follows: selecting probes with a GC content between 30% and 70%; the number of homology regions being less than or equal to 5; the selected probe region not containing SSR and N regions. According to the above design and selection principles, a total of 1795 probes were designed and selected, which could detect 894 target segments. The information of core SNP loci corresponding to 894 target segments is shown in Table 1, and the statistics of SNP marker chromosome distribution are shown in FIG. 1 and FIG. 2.

5. According to the 14 common detection sequences of cotton transgenic detection published by the Ministry of Agriculture, 14 detection probes were designed. The 14 detection probes provided in this example are shown as SEQ ID NOs. 1-14, which respectively detected A1Bt, A2CPTI, A3CP4-epsps, A4CP4-epsps, A5bar, A6pat, A7CdP450, A8cp4-epsps, B.1CaMV35S, B.2FMV35S, B.3NOS, B.4NOS, B.5CaMV35S and NPTII genes; the high-throughput sequencing sum analysis for the amplified product of the primer pair combination can be carried out for one time to complete the detection of transgenic components in the sample. Among them, the probes (SEQ ID NO. 3 and SEQ ID NO. 12) for detecting the A3CP4-epsps gene and B.4NOS gene are shown in the table; where I is hypoxanthine.

direct detection of transgenes during the breeding process. At present, the transgenic detection is generally targeted at a single gene/promoter sequence, so detecting 14 target

| | Sequence length | Sequence information | Gene name |
|---|---|---|---|
| SEQ ID NO. 3 | 333 | ACGGTGACCG TCTTCCCGTT ACCITGCGCG GGCCGAAGAC GCCGACGCCG ATCACCTACC GCGTGCCGAT GGCCTCCGCA CAGGTGAAGT CCGCCGTGCT GCTCGCCGGC CTCAACACGC CCGGCATCAC GACGGTCATC GAGCCGATCA TGACGCGCGA TCATACGGAAAAGATGCTGC AGGGCTTTGG CGCCAACCTT ACCGTCGAGA CGGATGCGGA CGGCGTGCGC ACCATCCGCC TGGAAGGCCG CGGCAAGCTC ACCGGCCAAG TCATCGACGT GCCGGGCGAC CCGTCCTCGA CGGCCTTCCC GCTGGTTGCG GCCCTGCTTG TTC | A3CP4-epsps |
| SEQ ID NO. 12 | 217 | ATCGTTCAAA CATTTGGCAA TAAAGTTTCT TAAGATTGAA TCCTGTTGCC GGTCTTGCGA TGATTATCAT ATTAATTICTG TTGAATTACG TTAAGCATGT AATAATTAAC ATIGTAATCCA TGACGTTATT TATGAGATGG GTTTTTATGA TTAGAGTCCC GCAATTATAC ATTTAATACG CGATAGAAAA CAATATAG CGCGCAAACT AGGATAA | B.4NOS |

6. The probes for detecting 894 SNP loci and 14 major transgenes were composed into a Low-density liquid-phase chip for *Gossypium hirsutum* L. based on targeted capture sequencing; wherein, 329 loci were significantly related to important agronomic traits such as fiber quality, yield and disease resistance of *Gossypium hirsutum* L., 14 loci were common plant transgenic detection loci, and 565 were other loci.

In this example, the capture probes synthesized by MOL-BREEDING Biotechnology Co., Ltd. were used to construct the chip, which was based on the targeted genotyping (GBTS) technology of liquid phase probe hybridization: GenoBaits. The working principle of GenoBaits is based on the complementary combination of target probes and target sequences for fixed-point capture. Firstly, the gDNA library of the materials to be tested was constructed. At the same time, a probe covering the target SNP was designed at each locus to be tested according to the principle of DNA complementarity, and the target probe was labeled with a Biotin label. Then, in a liquid state, the target probe labeled with Biotin hybridized with the target region of the genome to form a double strand. Subsequently, the target probe with the Biotin label was subjected to molecular adsorption by magnetic beads coated with streptavidin, so as to capture the target that hybridized with the probe. Finally, elution, target amplification, library building and sequencing were carried out on the captured target sequence, and finally the genotype of the target SNP was obtained.

The 894 SNP loci studied by the inventor are involved by *Gossypium hirsutum* L. itself, while are selected with full consideration of the distribution of these SNPs on chromosomes, and of the detection efficiency of the probes designed based on SNP markers in the population. Among them, 329 SNP loci are significantly associated with important agronomic traits, and 565 SNP loci are background loci. Therefore, the probes designed adopting these SNP markers can directly select target traits in breeding, as well as detecting the recovery rate of genetic background. For example, breeding target loci improve fiber quality, thus individuals with excellent haplotypes and high background recovery rate can be selected from the population based on fiber associated SNP markers, thereby enhancing the targeting of breeding, and accelerating the breeding process. The chip also includes probes for 14 major transgenes, allowing for fragments requires 14 PCR reactions, making the detection method cumbersome. The chip developed by the inventor can detect 14 major transgenic sequences while detecting 894 SNP haplotypes, improving detection efficiency.

TABLE 1

Information of 894 core SNP loci

| SNP number | Chromosome | Genome position | Ref | Alt | Whether it is a functional locus |
|---|---|---|---|---|---|
| 001 | A01 | 110747518 | C | T | Yes |
| 002 | A03 | 11727109 | T | C | Yes |
| 003 | A03 | 20665441 | A | G | Yes |
| 004 | A03 | 2166240 | A | G | Yes |
| 005 | A03 | 22543857 | C | T | Yes |
| 006 | A03 | 8450966 | A | T | Yes |
| 007 | A05 | 766233 | C | A | Yes |
| 008 | A10 | 111125064 | A | G | Yes |
| 009 | A10 | 111437317 | G | A | Yes |
| 010 | A10 | 112338179 | A | T | Yes |
| 011 | A10 | 112651380 | T | G | Yes |
| 012 | A10 | 112940238 | G | A | Yes |
| 013 | A10 | 113053553 | G | A | Yes |
| 014 | A11 | 30523772 | A | G | Yes |
| 015 | A12 | 87529643 | A | G | Yes |
| 016 | A13 | 103027858 | C | A | Yes |
| 017 | D02 | 4110390 | T | G | Yes |
| 018 | D03 | 15331946 | G | A | Yes |
| 019 | D03 | 31088497 | C | T | Yes |
| 020 | D03 | 34610610 | A | G | Yes |
| 021 | D03 | 39193206 | C | T | Yes |
| 022 | D03 | 39600506 | A | T | Yes |
| 023 | D03 | 40070059 | G | A | Yes |
| 024 | D03 | 43229382 | A | G | Yes |
| 025 | D03 | 43511381 | A | G | Yes |
| 026 | D03 | 43821808 | A | G | Yes |
| 027 | D03 | 44126802 | T | C | Yes |
| 028 | D03 | 45101555 | G | A | Yes |
| 029 | D03 | 45114135 | A | G | Yes |
| 030 | D03 | 45162922 | A | T | Yes |
| 031 | D03 | 45219545 | C | T | Yes |
| 032 | D03 | 45904637 | A | C | Yes |
| 033 | D03 | 46030279 | A | C | Yes |
| 034 | D04 | 53296491 | T | A | Yes |
| 035 | D04 | 53338317 | A | G | Yes |
| 036 | D04 | 55873730 | G | T | Yes |
| 037 | D04 | 55895101 | A | T | Yes |
| 038 | D06 | 11366732 | G | T | Yes |
| 039 | D09 | 7626032 | T | C | Yes |

7  8

TABLE 1-continued

Information of 894 core SNP loci

| SNP number | Chromosome | Genome position | Ref | Alt | Whether it is a functional locus |
|---|---|---|---|---|---|
| 040 | D10 | 5613642 | C | T | Yes |
| 041 | D10 | 65188256 | T | C | Yes |
| 042 | D11 | 171062 | T | C | Yes |
| 043 | D11 | 23848335 | T | C | Yes |
| 044 | D11 | 23889334 | T | C | Yes |
| 045 | D11 | 23957256 | A | T | Yes |
| 046 | D11 | 24042912 | C | T | Yes |
| 047 | D11 | 9255660 | C | T | Yes |
| 048 | D13 | 4503413 | G | A | Yes |
| 049 | A02 | 103887986 | G | A | Yes |
| 050 | A02 | 103969684 | T | C | Yes |
| 051 | A02 | 103980780 | A | G | Yes |
| 052 | A03 | 7639601 | A | G | Yes |
| 053 | A04 | 4584038 | G | A | Yes |
| 054 | A04 | 4584101 | C | T | Yes |
| 055 | A05 | 69623179 | C | T | Yes |
| 056 | A06 | 28180129 | G | G | Yes |
| 057 | A06 | 28338559 | T | C | Yes |
| 058 | A06 | 28760155 | A | G | Yes |
| 059 | A06 | 37577336 | T | C | Yes |
| 060 | A07 | 10774519 | G | A | Yes |
| 061 | A07 | 89225727 | T | C | Yes |
| 062 | A07 | 90178382 | T | C | Yes |
| 063 | A07 | 90300535 | G | T | Yes |
| 064 | A07 | 90432981 | T | C | Yes |
| 065 | A07 | 90438470 | G | A | Yes |
| 066 | A07 | 90497386 | C | T | Yes |
| 067 | A09 | 4830640 | G | A | Yes |
| 068 | A09 | 77528103 | G | T | Yes |
| 069 | A10 | 109602998 | G | A | Yes |
| 070 | A10 | 112187864 | C | A | Yes |
| 071 | A10 | 112213784 | T | C | Yes |
| 072 | A10 | 75431311 | A | G | Yes |
| 073 | A10 | 75517245 | C | G | Yes |
| 074 | A10 | 7883291 | T | C | Yes |
| 075 | A11 | 114890178 | C | T | Yes |
| 076 | A11 | 15811782 | G | A | Yes |
| 077 | A11 | 23909944 | C | | Yes |
| 078 | A11 | 360614 | A | C | Yes |
| 079 | A11 | 90244406 | C | A | Yes |
| 080 | A12 | 57229716 | A | G | Yes |
| 081 | A12 | 88694205 | C | T | Yes |
| 082 | A12 | 90492050 | C | T | Yes |
| 083 | A12 | 98576530 | C | T | Yes |
| 084 | A13 | 105476632 | G | T | Yes |
| 085 | A13 | 105477213 | G | A | Yes |
| 086 | A13 | 105486165 | G | A | Yes |
| 087 | A13 | 105603690 | T | C | Yes |
| 088 | D01 | 64087028 | G | C | Yes |
| 089 | D02 | 1013903 | T | C | Yes |
| 090 | D02 | 1396386 | T | C | Yes |
| 091 | D03 | 43272859 | G | C | Yes |
| 092 | D03 | 43289074 | A | T | Yes |
| 093 | D05 | 23684485 | C | A | Yes |
| 094 | D05 | 5720265 | G | T | Yes |
| 095 | D05 | 57485276 | C | A | Yes |
| 096 | D05 | 58079007 | G | A | Yes |
| 097 | D05 | 58177617 | C | T | Yes |
| 098 | D06 | 12003138 | G | A | Yes |
| 099 | D06 | 17773574 | A | G | Yes |
| 100 | D06 | 60207647 | G | C | Yes |
| 101 | D06 | 8776619 | G | | Yes |
| 102 | D07 | 19075384 | A | G | Yes |
| 103 | D07 | 51856497 | T | C | Yes |
| 104 | D07 | 6729179 | A | C | Yes |
| 105 | D08 | 2896926 | A | C | Yes |
| 106 | D08 | 2901847 | A | G | Yes |
| 107 | D08 | 2904400 | A | G | Yes |
| 108 | D08 | 5505113 | G | T | Yes |
| 109 | D08 | 63065133 | G | C | Yes |
| 110 | D09 | 6549285 | G | A | Yes |
| 111 | D10 | 2524436 | C | A | Yes |
| 112 | D11 | 57041068 | C | T | Yes |
| 113 | D11 | 58261390 | A | C | Yes |
| 114 | D11 | 64752270 | C | A | Yes |
| 115 | D11 | 64756382 | T | C | Yes |
| 116 | D11 | 64904998 | G | C | Yes |
| 117 | D11 | 64926164 | C | T | Yes |
| 118 | D11 | 64930470 | T | C | Yes |
| 119 | D11 | 64937064 | G | C | Yes |
| 120 | D11 | 65065455 | C | A | Yes |
| 121 | D12 | 53158662 | G | A | Yes |
| 122 | D12 | 60059695 | T | C | Yes |
| 123 | D13 | 1774748 | C | T | Yes |
| 124 | D13 | 229536 | C | G | Yes |
| 125 | D13 | 45090184 | T | G | Yes |
| 126 | D13 | 53340754 | A | C | Yes |
| 127 | D13 | 8371110 | A | C | Yes |
| 128 | seq1 | 39098148 | T | A | Yes |
| 129 | seq1 | 39098165 | A | C | Yes |
| 130 | seq1 | 39098173 | G | C | Yes |
| 131 | seq1 | 9660644 | C | G | Yes |
| 132 | A01 | 2102346 | T | C | Yes |
| 133 | A01 | 8820452 | A | C | Yes |
| 134 | A02 | 1689682 | C | T | Yes |
| 135 | A03 | 51260473 | T | A | Yes |
| 136 | A04 | 6518897 | C | T | Yes |
| 137 | A05 | 11730945 | G | A | Yes |
| 138 | A05 | 75751203 | T | C | Yes |
| 139 | A06 | 8750649 | T | C | Yes |
| 140 | A07 | 1032070 | A | C | Yes |
| 141 | A07 | 1032071 | G | T | Yes |
| 142 | A07 | 12032478 | C | T | Yes |
| 143 | A07 | 95507309 | C | G | Yes |
| 144 | A07 | 989813 | T | A | Yes |
| 145 | A08 | 117118370 | A | G | Yes |
| 146 | A08 | 119190686 | T | C | Yes |
| 147 | A08 | 124176460 | A | G | Yes |
| 148 | A08 | 6187342 | T | C | Yes |
| 149 | A08 | 97074019 | C | T | Yes |
| 150 | A09 | 13706113 | T | C | Yes |
| 151 | A10 | 109236405 | A | G | Yes |
| 152 | A10 | 114220963 | C | T | Yes |
| 153 | A12 | 94150095 | C | T | Yes |
| 154 | A13 | 106412709 | C | T | Yes |
| 155 | A13 | 109879969 | C | T | Yes |
| 156 | A13 | 6433021 | T | C | Yes |
| 157 | D01 | 1150200 | T | A | Yes |
| 158 | D01 | 18933398 | C | T | Yes |
| 159 | D01 | 600285 | C | T | Yes |
| 160 | D02 | 12661527 | T | C | Yes |
| 161 | D02 | 1920733 | C | G | Yes |
| 162 | D02 | 1946913 | A | G | Yes |
| 163 | D02 | 44762375 | T | C | Yes |
| 164 | D02 | 6392666 | G | A | Yes |
| 165 | D02 | 68951786 | C | A | Yes |
| 166 | D03 | 2487227 | A | G | Yes |
| 167 | D04 | 1347244 | A | G | Yes |
| 168 | D04 | 52647897 | A | G | Yes |
| 169 | D05 | 26764654 | C | T | Yes |
| 170 | D05 | 45810951 | A | G | Yes |
| 171 | D06 | 1497967 | G | A | Yes |
| 172 | D06 | 1624645 | A | C | Yes |
| 173 | D06 | 54504155 | A | T | Yes |
| 174 | D06 | 59180787 | G | A | Yes |
| 175 | D06 | 61085437 | T | A | Yes |
| 176 | D07 | 46303166 | A | G | Yes |
| 177 | D08 | 61439658 | G | A | Yes |
| 178 | D08 | 68631323 | C | T | Yes |
| 179 | D08 | 9335830 | C | T | Yes |
| 180 | D09 | 2749569 | A | C | Yes |
| 181 | D09 | 38068242 | T | C | Yes |
| 182 | D11 | 1280801 | G | A | Yes |
| 183 | D12 | 15727440 | T | C | Yes |
| 184 | D12 | 58551591 | C | T | Yes |
| 185 | D12 | 7113678 | G | A | Yes |

TABLE 1-continued

Information of 894 core SNP loci

| SNP number | Chromosome | Genome position | Ref | Alt | Whether it is a functional locus |
|---|---|---|---|---|---|
| 186 | D13 | 59655465 | T | G | Yes |
| 187 | D13 | 60649746 | G | A | Yes |
| 188 | A01 | 110967771 | A | C | Yes |
| 189 | A02 | 107361717 | T | A | Yes |
| 190 | A02 | 1707434 | G | A | Yes |
| 191 | A02 | 26551420 | G | A | Yes |
| 192 | A05 | 14504864 | C | T | Yes |
| 193 | A05 | 14504889 | A | G | Yes |
| 194 | A05 | 15429410 | C | G | Yes |
| 195 | A07 | 42902490 | C | G | Yes |
| 196 | A07 | 90603512 | T | G | Yes |
| 197 | A07 | 90783146 | G | A | Yes |
| 198 | A08 | 112071927 | C | T | Yes |
| 199 | A10 | 110613300 | T | C | Yes |
| 200 | A11 | 104539963 | T | C | Yes |
| 201 | D02 | 1913626 | A | G | Yes |
| 202 | D02 | 1915388 | T | C | Yes |
| 203 | D02 | 6362048 | C | T | Yes |
| 204 | D04 | 1546736 | T | A | Yes |
| 205 | D05 | 14240130 | T | G | Yes |
| 206 | D06 | 45390691 | C | T | Yes |
| 207 | D06 | 46672551 | C | T | Yes |
| 208 | D08 | 18841330 | A | C | Yes |
| 209 | D11 | 20428933 | A | T | Yes |
| 210 | A01 | 114857126 | G | A | Yes |
| 211 | A01 | 115721972 | A | G | Yes |
| 212 | A01 | 117760175 | T | C | Yes |
| 213 | A01 | 117760658 | T | A | Yes |
| 214 | A02 | 106224475 | A | G | Yes |
| 215 | A02 | 3111851 | A | G | Yes |
| 216 | A03 | 110233891 | A | G | Yes |
| 217 | A04 | 67550448 | A | T | Yes |
| 218 | A04 | 86560855 | C | T | Yes |
| 219 | A04 | 86568861 | C | T | Yes |
| 220 | A05 | 105715349 | A | G | Yes |
| 221 | A05 | 15876258 | T | C | Yes |
| 222 | A05 | 15876308 | C | G | Yes |
| 223 | A05 | 1874595 | A | G | Yes |
| 224 | A05 | 2124121 | C | T | Yes |
| 225 | A05 | 22775565 | G | A | Yes |
| 226 | A05 | 22924264 | T | A | Yes |
| 227 | A05 | 22938538 | A | T | Yes |
| 228 | A05 | 31423050 | T | C | Yes |
| 229 | A06 | 119255407 | C | T | Yes |
| 230 | A06 | 124093748 | C | T | Yes |
| 231 | A06 | 1503775 | C | G | Yes |
| 232 | A07 | 21563371 | C | T | Yes |
| 233 | A07 | 23460168 | C | T | Yes |
| 234 | A07 | 83188617 | G | C | Yes |
| 235 | A07 | 88838111 | C | T | Yes |
| 236 | A07 | 90625054 | C | T | Yes |
| 237 | A07 | 90633925 | C | T | Yes |
| 238 | A07 | 90639206 | T | C | Yes |
| 239 | A08 | 104027372 | A | G | Yes |
| 240 | A08 | 107661059 | T | G | Yes |
| 241 | A08 | 123086263 | C | G | Yes |
| 242 | A08 | 123101111 | T | C | Yes |
| 243 | A08 | 31131479 | C | T | Yes |
| 244 | A08 | 6469161 | T | A | Yes |
| 245 | A09 | 73717101 | C | A | Yes |
| 246 | A10 | 108187386 | C | T | Yes |
| 247 | A10 | 114006682 | G | A | Yes |
| 248 | A10 | 2516523 | C | T | Yes |
| 249 | A10 | 4309496 | C | A | Yes |
| 250 | A11 | 118950829 | A | T | Yes |
| 251 | A11 | 24222 | G | A | Yes |
| 252 | A11 | 9073286 | G | A | Yes |
| 253 | A11 | 99926974 | A | G | Yes |
| 254 | A12 | 104493499 | T | A | Yes |
| 255 | A12 | 95983460 | C | G | Yes |
| 256 | A13 | 100671788 | C | T | Yes |
| 257 | A13 | 104864916 | T | G | Yes |
| 258 | A13 | 107008682 | A | G | Yes |

TABLE 1-continued

Information of 894 core SNP loci

| SNP number | Chromosome | Genome position | Ref | Alt | Whether it is a functional locus |
|---|---|---|---|---|---|
| 259 | A13 | 5759232 | A | G | Yes |
| 260 | A13 | 68442801 | C | A | Yes |
| 261 | A13 | 89442130 | G | A | Yes |
| 262 | A13 | 98283310 | T | C | Yes |
| 263 | D01 | 19034036 | T | A | Yes |
| 264 | D01 | 54855218 | T | C | Yes |
| 265 | D01 | 54866986 | C | T | Yes |
| 266 | D01 | 54890106 | T | C | Yes |
| 267 | D01 | 54896281 | G | A | Yes |
| 268 | D01 | 57261588 | A | G | Yes |
| 269 | D01 | 58881229 | C | T | Yes |
| 270 | D02 | 51851185 | A | G | Yes |
| 271 | D02 | 52987299 | A | G | Yes |
| 272 | D02 | 53034743 | G | T | Yes |
| 273 | D02 | 53253589 | A | C | Yes |
| 274 | D02 | 54901956 | C | T | Yes |
| 275 | D02 | 63310106 | T | C | Yes |
| 276 | D02 | 6401616 | T | A | Yes |
| 277 | D02 | 68030533 | A | T | Yes |
| 278 | D02 | 7489387 | T | G | Yes |
| 279 | D02 | 7531127 | A | G | Yes |
| 280 | D03 | 2503186 | G | T | Yes |
| 281 | D04 | 52350838 | T | G | Yes |
| 282 | D04 | 6848742 | A | C | Yes |
| 283 | D04 | 6861687 | C | T | Yes |
| 284 | D04 | 851577 | G | A | Yes |
| 285 | D05 | 14718765 | A | G | Yes |
| 286 | D05 | 55154526 | T | C | Yes |
| 287 | D05 | 56805649 | A | G | Yes |
| 288 | D06 | 18372518 | T | A | Yes |
| 289 | D06 | 47311286 | G | T | Yes |
| 290 | D06 | 64318600 | T | C | Yes |
| 291 | D07 | 10130687 | G | C | Yes |
| 292 | D07 | 54754308 | T | C | Yes |
| 293 | D07 | 54818140 | G | A | Yes |
| 294 | D07 | 54821539 | T | A | Yes |
| 295 | D08 | 2748641 | C | T | Yes |
| 296 | D08 | 430878 | C | A | Yes |
| 297 | D08 | 4868113 | C | T | Yes |
| 298 | D08 | 608978 | C | T | Yes |
| 299 | D09 | 49092148 | A | G | Yes |
| 300 | D09 | 6069425 | C | T | Yes |
| 301 | D10 | 63443095 | G | C | Yes |
| 302 | D10 | 63918764 | C | T | Yes |
| 303 | D10 | 64184291 | A | T | Yes |
| 304 | D10 | 826050 | A | G | Yes |
| 305 | D11 | 10658879 | T | C | Yes |
| 306 | D11 | 13890576 | T | C | Yes |
| 307 | D11 | 21988164 | G | A | Yes |
| 308 | D11 | 23924389 | T | A | Yes |
| 309 | D11 | 23924409 | C | T | Yes |
| 310 | D11 | 23944152 | C | T | Yes |
| 311 | D11 | 24002127 | A | G | Yes |
| 312 | D11 | 24004889 | C | T | Yes |
| 313 | D11 | 24034422 | G | C | Yes |
| 314 | D11 | 24036519 | A | G | Yes |
| 315 | D11 | 3229941 | A | G | Yes |
| 316 | D11 | 3230659 | C | T | Yes |
| 317 | D11 | 62899476 | G | A | Yes |
| 318 | D12 | 1201966 | C | A | Yes |
| 319 | D12 | 2093018 | T | G | Yes |
| 320 | D12 | 2108978 | A | G | Yes |
| 321 | D12 | 2237848 | G | A | Yes |
| 322 | D12 | 49521512 | A | G | Yes |
| 323 | D12 | 49927212 | G | A | Yes |
| 324 | D12 | 53455112 | T | A | Yes |
| 325 | D12 | 55839588 | C | T | Yes |
| 326 | D12 | 61139512 | A | C | Yes |
| 327 | D12 | 61140550 | C | T | Yes |
| 328 | D13 | 44115715 | T | G | Yes |
| 329 | D13 | 45131566 | A | G | Yes |
| 330 | A01 | 102077466 | C | T | No |
| 331 | A01 | 103023924 | G | A | No |

TABLE 1-continued

Information of 894 core SNP loci

| SNP number | Chromosome | Genome position | Ref | Alt | Whether it is a functional locus |
|---|---|---|---|---|---|
| 332 | A01 | 109299115 | A | G | No |
| 333 | A01 | 110128160 | A | G | No |
| 334 | A01 | 110687776 | A | T | No |
| 335 | A01 | 113567604 | C | T | No |
| 336 | A01 | 114087981 | G | A | No |
| 337 | A01 | 11692652 | C | T | No |
| 338 | A01 | 17937689 | T | C | No |
| 339 | A01 | 19586649 | T | C | No |
| 340 | A01 | 20011715 | C | T | No |
| 341 | A01 | 23552093 | C | T | No |
| 342 | A01 | 25130938 | T | C | No |
| 343 | A01 | 29630645 | A | G | No |
| 344 | A01 | 30304909 | A | G | No |
| 345 | A01 | 30655283 | T | C | No |
| 346 | A01 | 31298172 | T | A | No |
| 347 | A01 | 37097863 | G | A | No |
| 348 | A01 | 39816020 | G | C | No |
| 349 | A01 | 44008051 | G | A | No |
| 350 | A01 | 45886993 | C | T | No |
| 351 | A01 | 48030807 | G | A | No |
| 352 | A01 | 50753667 | C | A | No |
| 353 | A01 | 52461718 | G | C | No |
| 354 | A01 | 53550328 | A | G | No |
| 355 | A01 | 55361298 | T | C | No |
| 356 | A01 | 5665093 | A | G | No |
| 357 | A01 | 59440674 | A | G | No |
| 358 | A01 | 60660225 | T | C | No |
| 359 | A01 | 62406568 | T | C | No |
| 360 | A01 | 69399954 | A | G | No |
| 361 | A01 | 72356977 | A | G | No |
| 362 | A01 | 73066978 | C | T | No |
| 363 | A01 | 83056539 | G | C | No |
| 364 | A01 | 9307886 | T | C | No |
| 365 | A01 | 94433050 | C | G | No |
| 366 | A01 | 97114671 | G | A | No |
| 367 | A01 | 9928461 | A | G | No |
| 368 | A01 | 9992909 | T | C | No |
| 369 | A02 | 104702522 | C | G | No |
| 370 | A02 | 106564817 | G | A | No |
| 371 | A02 | 126465 | A | G | No |
| 372 | A02 | 18537125 | A | G | No |
| 373 | A02 | 19418124 | T | C | No |
| 374 | A02 | 3608260 | T | A | No |
| 375 | A02 | 3753565 | C | G | No |
| 376 | A02 | 39122586 | T | C | No |
| 377 | A02 | 44761669 | C | A | No |
| 378 | A02 | 44836527 | T | C | No |
| 379 | A02 | 52198772 | A | G | No |
| 380 | A02 | 63519897 | A | G | No |
| 381 | A02 | 64573030 | C | T | No |
| 382 | A02 | 64810766 | A | G | No |
| 383 | A02 | 71898039 | G | C | No |
| 384 | A02 | 76764218 | C | A | No |
| 385 | A02 | 79665360 | C | T | No |
| 386 | A02 | 82773518 | A | G | No |
| 387 | A02 | 8356092 | C | T | No |
| 388 | A02 | 95037408 | T | G | No |
| 389 | A03 | 10432099 | T | C | No |
| 390 | A03 | 104900576 | A | C | No |
| 391 | A03 | 106410955 | G | A | No |
| 392 | A03 | 16588547 | T | C | No |
| 393 | A03 | 35348610 | T | C | No |
| 394 | A03 | 36068818 | T | C | No |
| 395 | A03 | 41629111 | T | C | No |
| 396 | A03 | 62010341 | C | T | No |
| 397 | A03 | 72339471 | A | G | No |
| 398 | A03 | 81970703 | T | C | No |
| 399 | A03 | 91791344 | T | C | No |
| 400 | A03 | 93575802 | T | C | No |
| 401 | A03 | 93642770 | G | T | No |
| 402 | A03 | 95039694 | T | C | No |
| 403 | A03 | 95047213 | A | G | No |
| 404 | A03 | 95068176 | A | C | No |

TABLE 1-continued

Information of 894 core SNP loci

| SNP number | Chromosome | Genome position | Ref | Alt | Whether it is a functional locus |
|---|---|---|---|---|---|
| 405 | A03 | 95073577 | T | A | No |
| 406 | A03 | 95086199 | C | T | No |
| 407 | A03 | 95090581 | A | G | No |
| 408 | A03 | 95091209 | G | A | No |
| 409 | A03 | 97554243 | A | T | No |
| 410 | A04 | 11004835 | T | G | No |
| 411 | A04 | 11910166 | C | T | No |
| 412 | A04 | 12158377 | C | T | No |
| 413 | A04 | 12243883 | A | G | No |
| 414 | A04 | 13827618 | T | C | No |
| 415 | A04 | 16789748 | A | G | No |
| 416 | A04 | 1886870 | C | T | No |
| 417 | A04 | 1958101 | A | G | No |
| 418 | A04 | 1969979 | T | C | No |
| 419 | A04 | 22382054 | C | G | No |
| 420 | A04 | 36328459 | G | A | No |
| 421 | A04 | 37588019 | A | G | No |
| 422 | A04 | 55428635 | G | A | No |
| 423 | A04 | 61481730 | C | T | No |
| 424 | A04 | 69596220 | G | A | No |
| 425 | A04 | 7163673 | C | G | No |
| 426 | A04 | 7164063 | C | T | No |
| 427 | A04 | 81630879 | T | C | No |
| 428 | A04 | 83437396 | A | G | No |
| 429 | A04 | 84817926 | T | A | No |
| 430 | A05 | 101965827 | A | G | No |
| 431 | A05 | 102937436 | T | C | No |
| 432 | A05 | 106162489 | C | T | No |
| 433 | A05 | 1273243 | T | G | No |
| 434 | A05 | 24223452 | C | T | No |
| 435 | A05 | 28843012 | G | A | No |
| 436 | A05 | 36231152 | A | G | No |
| 437 | A05 | 36585565 | T | G | No |
| 438 | A05 | 39529362 | C | T | No |
| 439 | A05 | 40529916 | T | C | No |
| 440 | A05 | 54824863 | C | T | No |
| 441 | A05 | 59499071 | G | A | No |
| 442 | A05 | 75568141 | A | G | No |
| 443 | A05 | 75568470 | A | G | No |
| 444 | A05 | 78899507 | G | A | No |
| 445 | A05 | 94441223 | C | G | No |
| 446 | A05 | 94467545 | G | T | No |
| 447 | A05 | 96112268 | T | C | No |
| 448 | A05 | 97278925 | G | T | No |
| 449 | A05 | 98875724 | G | T | No |
| 450 | A06 | 100673641 | T | C | No |
| 451 | A06 | 119009915 | A | G | No |
| 452 | A06 | 120558212 | G | A | No |
| 453 | A06 | 12521911 | A | G | No |
| 454 | A06 | 1289926 | T | C | No |
| 455 | A06 | 14409659 | T | C | No |
| 456 | A06 | 19263878 | T | C | No |
| 457 | A06 | 19510906 | A | G | No |
| 458 | A06 | 24921227 | T | G | No |
| 459 | A06 | 25685023 | C | T | No |
| 460 | A06 | 30796846 | T | C | No |
| 461 | A06 | 32683074 | T | C | No |
| 462 | A06 | 32798852 | G | A | No |
| 463 | A06 | 34369034 | T | C | No |
| 464 | A06 | 36798412 | T | C | No |
| 465 | A06 | 46083287 | G | A | No |
| 466 | A06 | 46958830 | A | C | No |
| 467 | A06 | 47635932 | A | G | No |
| 468 | A06 | 47877963 | A | G | No |
| 469 | A06 | 5322494 | A | C | No |
| 470 | A06 | 72157456 | T | C | No |
| 471 | A06 | 73439358 | G | A | No |
| 472 | A06 | 75814615 | C | T | No |
| 473 | A06 | 78918757 | A | G | No |
| 474 | A06 | 80502017 | G | C | No |
| 475 | A06 | 80669852 | T | C | No |
| 476 | A06 | 80914576 | T | C | No |
| 477 | A06 | 83069476 | A | G | No |

TABLE 1-continued

Information of 894 core SNP loci

| SNP number | Chromosome | Genome position | Ref | Alt | Whether it is a functional locus |
|---|---|---|---|---|---|
| 478 | A06 | 83420195 | A | G | No |
| 479 | A06 | 83713547 | A | G | No |
| 480 | A06 | 89002323 | T | C | No |
| 481 | A06 | 89566493 | T | C | No |
| 482 | A06 | 90969355 | A | G | No |
| 483 | A06 | 93187658 | T | C | No |
| 484 | A06 | 95478943 | T | C | No |
| 485 | A06 | 973530 | C | T | No |
| 486 | A07 | 11906060 | T | C | No |
| 487 | A07 | 11915754 | C | T | No |
| 488 | A07 | 12320575 | T | C | No |
| 489 | A07 | 18648297 | G | A | No |
| 490 | A07 | 21310224 | T | C | No |
| 491 | A07 | 21785923 | A | G | No |
| 492 | A07 | 25884125 | G | A | No |
| 493 | A07 | 29041927 | C | T | No |
| 494 | A07 | 36875269 | C | G | No |
| 495 | A07 | 38342570 | T | C | No |
| 496 | A07 | 40698615 | G | A | No |
| 497 | A07 | 42581937 | T | C | No |
| 498 | A07 | 43180984 | A | G | No |
| 499 | A07 | 43810960 | A | G | No |
| 500 | A07 | 43986311 | T | C | No |
| 501 | A07 | 47819857 | A | G | No |
| 502 | A07 | 54517045 | G | A | No |
| 503 | A07 | 64238084 | C | T | No |
| 504 | A07 | 80217572 | C | T | No |
| 505 | A07 | 80388490 | A | T | No |
| 506 | A07 | 82916184 | T | C | No |
| 507 | A07 | 83105438 | G | A | No |
| 508 | A07 | 8422752 | G | C | No |
| 509 | A07 | 89161736 | A | G | No |
| 510 | A07 | 9478030 | A | C | No |
| 511 | A08 | 10429943 | C | G | No |
| 512 | A08 | 106893339 | C | T | No |
| 513 | A08 | 109696323 | G | A | No |
| 514 | A08 | 112025642 | C | T | No |
| 515 | A08 | 113464785 | A | G | No |
| 516 | A08 | 116730869 | A | G | No |
| 517 | A08 | 1713011 | T | C | No |
| 518 | A08 | 19121855 | C | A | No |
| 519 | A08 | 20388949 | G | A | No |
| 520 | A08 | 25642734 | C | T | No |
| 521 | A08 | 29214900 | C | T | No |
| 522 | A08 | 29234582 | A | C | No |
| 523 | A08 | 29239926 | T | C | No |
| 524 | A08 | 29243822 | A | G | No |
| 525 | A08 | 4039263 | C | T | No |
| 526 | A08 | 48463216 | T | C | No |
| 527 | A08 | 55388879 | C | T | No |
| 528 | A08 | 56754026 | A | G | No |
| 529 | A08 | 63452446 | G | A | No |
| 530 | A08 | 64485512 | G | A | No |
| 531 | A08 | 78341697 | C | T | No |
| 532 | A08 | 89152238 | A | G | No |
| 533 | A08 | 89152667 | T | C | No |
| 534 | A08 | 93471156 | A | T | No |
| 535 | A08 | 99343910 | A | G | No |
| 536 | A09 | 12673218 | T | C | No |
| 537 | A09 | 12998204 | C | T | No |
| 538 | A09 | 14103382 | C | T | No |
| 539 | A09 | 20823587 | T | A | No |
| 540 | A09 | 20844042 | G | A | No |
| 541 | A09 | 23502455 | A | C | No |
| 542 | A09 | 25275518 | T | G | No |
| 543 | A09 | 31554465 | C | T | No |
| 544 | A09 | 40968413 | A | G | No |
| 545 | A09 | 42870985 | A | G | No |
| 546 | A09 | 45777 | C | A | No |
| 547 | A09 | 47518943 | G | A | No |
| 548 | A09 | 51396443 | G | A | No |
| 549 | A09 | 55493894 | C | G | No |
| 550 | A09 | 61184216 | A | G | No |

TABLE 1-continued

Information of 894 core SNP loci

| SNP number | Chromosome | Genome position | Ref | Alt | Whether it is a functional locus |
|---|---|---|---|---|---|
| 551 | A09 | 61363297 | G | T | No |
| 552 | A09 | 65591384 | T | C | No |
| 553 | A09 | 67674689 | G | T | No |
| 554 | A09 | 76025039 | G | A | No |
| 555 | A10 | 10543466 | A | G | No |
| 556 | A10 | 106581756 | T | C | No |
| 557 | A10 | 107143359 | T | G | No |
| 558 | A10 | 107787459 | G | A | No |
| 559 | A10 | 10945265 | A | C | No |
| 560 | A10 | 112338443 | T | A | No |
| 561 | A10 | 15068940 | G | A | No |
| 562 | A10 | 18866303 | A | C | No |
| 563 | A10 | 27447943 | A | G | No |
| 564 | A10 | 3130405 | C | T | No |
| 565 | A10 | 3310056 | T | C | No |
| 566 | A10 | 45696050 | C | A | No |
| 567 | A10 | 48324687 | G | A | No |
| 568 | A10 | 48366731 | A | G | No |
| 569 | A10 | 56444175 | C | T | No |
| 570 | A10 | 6404617 | T | C | No |
| 571 | A10 | 6555180 | A | G | No |
| 572 | A10 | 6738311 | A | C | No |
| 573 | A10 | 68078336 | A | G | No |
| 574 | A10 | 76202810 | T | C | No |
| 575 | A10 | 85468645 | A | G | No |
| 576 | A11 | 11016688 | T | C | No |
| 577 | A11 | 11441789 | A | G | No |
| 578 | A11 | 1394259 | C | G | No |
| 579 | A11 | 16077265 | G | A | No |
| 580 | A11 | 18005388 | A | G | No |
| 581 | A11 | 23540980 | C | T | No |
| 582 | A11 | 25232174 | C | A | No |
| 583 | A11 | 25233949 | T | C | No |
| 584 | A11 | 30735652 | A | G | No |
| 585 | A11 | 31753695 | A | G | No |
| 586 | A11 | 35871174 | A | C | No |
| 587 | A11 | 37921426 | C | A | No |
| 588 | A11 | 52514719 | T | C | No |
| 589 | A11 | 55123151 | A | G | No |
| 590 | A11 | 56784796 | T | C | No |
| 591 | A11 | 62701332 | T | C | No |
| 592 | A11 | 63434388 | A | G | No |
| 593 | A11 | 66244941 | A | G | No |
| 594 | A11 | 67626090 | T | C | No |
| 595 | A11 | 67630369 | G | C | No |
| 596 | A11 | 68182818 | A | G | No |
| 597 | A11 | 68183232 | C | T | No |
| 598 | A11 | 70719189 | A | G | No |
| 599 | A11 | 77534048 | C | T | No |
| 600 | A11 | 82139694 | G | A | No |
| 601 | A11 | 85424243 | T | C | No |
| 602 | A11 | 89746643 | A | T | No |
| 603 | A11 | 90149203 | C | T | No |
| 604 | A11 | 92066056 | T | C | No |
| 605 | A11 | 92429725 | C | T | No |
| 606 | A11 | 95752317 | A | T | No |
| 607 | A11 | 98573925 | A | G | No |
| 608 | A12 | 10226218 | G | A | No |
| 609 | A12 | 11396410 | G | A | No |
| 610 | A12 | 11429480 | G | A | No |
| 611 | A12 | 12115755 | C | T | No |
| 612 | A12 | 16073340 | A | G | No |
| 613 | A12 | 17820382 | G | T | No |
| 614 | A12 | 22544556 | T | G | No |
| 615 | A12 | 24422845 | T | C | No |
| 616 | A12 | 3233765 | A | G | No |
| 617 | A12 | 36619695 | G | A | No |
| 618 | A12 | 40703533 | G | A | No |
| 619 | A12 | 4152128 | A | G | No |
| 620 | A12 | 44104522 | G | T | No |
| 621 | A12 | 44388198 | A | G | No |
| 622 | A12 | 44629878 | T | A | No |
| 623 | A12 | 5091648 | T | A | No |

TABLE 1-continued

Information of 894 core SNP loci

| SNP number | Chromosome | Genome position | Ref | Alt | Whether it is a functional locus |
|---|---|---|---|---|---|
| 624 | A12 | 52831490 | G | C | No |
| 625 | A12 | 60989615 | A | C | No |
| 626 | A12 | 6396346 | A | G | No |
| 627 | A12 | 68296841 | G | A | No |
| 628 | A12 | 7194840 | G | A | No |
| 629 | A12 | 77899237 | C | T | No |
| 630 | A12 | 7810671 | C | G | No |
| 631 | A12 | 7969574 | A | G | No |
| 632 | A12 | 80173437 | G | A | No |
| 633 | A13 | 100127785 | G | A | No |
| 634 | A13 | 101918312 | G | A | No |
| 635 | A13 | 17036027 | A | C | No |
| 636 | A13 | 17036590 | C | T | No |
| 637 | A13 | 21731709 | A | G | No |
| 638 | A13 | 23198397 | T | C | No |
| 639 | A13 | 27322121 | A | G | No |
| 640 | A13 | 278763 | T | G | No |
| 641 | A13 | 35844566 | G | A | No |
| 642 | A13 | 45195746 | A | G | No |
| 643 | A13 | 45220863 | T | C | No |
| 644 | A13 | 45223069 | A | G | No |
| 645 | A13 | 45229632 | C | G | No |
| 646 | A13 | 45230181 | G | A | No |
| 647 | A13 | 45238518 | T | A | No |
| 648 | A13 | 45240195 | A | G | No |
| 649 | A13 | 50036635 | C | G | No |
| 650 | A13 | 59746791 | T | C | No |
| 651 | A13 | 7768028 | C | T | No |
| 652 | A13 | 77893733 | G | A | No |
| 653 | A13 | 78230319 | G | A | No |
| 654 | A13 | 79597429 | A | G | No |
| 655 | A13 | 80392586 | T | C | No |
| 656 | A13 | 80452058 | A | G | No |
| 657 | A13 | 80730886 | C | A | No |
| 658 | A13 | 81306936 | C | T | No |
| 659 | A13 | 83761879 | T | C | No |
| 660 | A13 | 89445949 | A | G | No |
| 661 | A13 | 9366668 | A | T | No |
| 662 | A13 | 94821021 | C | T | No |
| 663 | A13 | 94837745 | C | T | No |
| 664 | A13 | 94898464 | G | T | No |
| 665 | A13 | 96661617 | A | G | No |
| 666 | A13 | 97785453 | C | T | No |
| 667 | D01 | 24764505 | A | T | No |
| 668 | D01 | 24767839 | T | C | No |
| 669 | D01 | 31464245 | G | T | No |
| 670 | D01 | 32265626 | A | G | No |
| 671 | D01 | 32543583 | T | C | No |
| 672 | D01 | 33576723 | A | G | No |
| 673 | D01 | 37246475 | G | A | No |
| 674 | D01 | 38589185 | C | A | No |
| 675 | D01 | 40297859 | T | C | No |
| 676 | D01 | 42570072 | C | A | No |
| 677 | D01 | 46056348 | C | A | No |
| 678 | D01 | 54437017 | G | T | No |
| 679 | D01 | 54531974 | A | G | No |
| 680 | D01 | 54532596 | A | C | No |
| 681 | D01 | 54841313 | C | T | No |
| 682 | D01 | 56204975 | T | C | No |
| 683 | D01 | 56387888 | T | A | No |
| 684 | D01 | 59941820 | C | T | No |
| 685 | D01 | 63516128 | A | G | No |
| 686 | D01 | 9090589 | A | T | No |
| 687 | D02 | 17045564 | T | A | No |
| 688 | D02 | 18307420 | C | A | No |
| 689 | D02 | 18765233 | A | G | No |
| 690 | D02 | 19924810 | G | A | No |
| 691 | D02 | 23266296 | G | A | No |
| 692 | D02 | 29523923 | T | A | No |
| 693 | D02 | 30504620 | G | T | No |
| 694 | D02 | 38335405 | A | G | No |
| 695 | D02 | 45180077 | T | A | No |
| 696 | D02 | 4665984 | G | A | No |

TABLE 1-continued

Information of 894 core SNP loci

| SNP number | Chromosome | Genome position | Ref | Alt | Whether it is a functional locus |
|---|---|---|---|---|---|
| 697 | D02 | 50316439 | A | C | No |
| 698 | D02 | 50316584 | A | G | No |
| 699 | D02 | 54044417 | A | G | No |
| 700 | D02 | 57420904 | G | A | No |
| 701 | D02 | 57735413 | T | C | No |
| 702 | D02 | 59149744 | A | C | No |
| 703 | D02 | 60903663 | A | G | No |
| 704 | D02 | 64071331 | A | G | No |
| 705 | D02 | 64105609 | T | C | No |
| 706 | D02 | 652122 | G | A | No |
| 707 | D02 | 69573139 | T | C | No |
| 708 | D03 | 10851700 | G | C | No |
| 709 | D03 | 12601043 | T | C | No |
| 710 | D03 | 19246208 | T | C | No |
| 711 | D03 | 25627391 | C | T | No |
| 712 | D03 | 25646216 | C | T | No |
| 713 | D03 | 27701555 | C | T | No |
| 714 | D03 | 31735979 | T | C | No |
| 715 | D03 | 34571433 | G | T | No |
| 716 | D03 | 36559975 | C | T | No |
| 717 | D03 | 4447807 | G | A | No |
| 718 | D03 | 46722299 | T | C | No |
| 719 | D03 | 47897510 | G | A | No |
| 720 | D03 | 48891235 | A | G | No |
| 721 | D03 | 50598904 | G | T | No |
| 722 | D03 | 5253112 | T | G | No |
| 723 | D03 | 5254940 | A | C | No |
| 724 | D03 | 6554186 | A | G | No |
| 725 | D03 | 6884462 | G | T | No |
| 726 | D03 | 7213302 | T | C | No |
| 727 | D03 | 8405927 | A | G | No |
| 728 | D04 | 19963729 | C | G | No |
| 729 | D04 | 25993830 | C | T | No |
| 730 | D04 | 28820458 | C | T | No |
| 731 | D04 | 34164246 | A | G | No |
| 732 | D04 | 34164765 | T | C | No |
| 733 | D04 | 34168061 | T | C | No |
| 734 | D04 | 34170181 | T | G | No |
| 735 | D04 | 34186357 | A | G | No |
| 736 | D04 | 34188285 | T | C | No |
| 737 | D04 | 34209861 | G | T | No |
| 738 | D04 | 34212452 | T | C | No |
| 739 | D04 | 4477447 | G | A | No |
| 740 | D04 | 50668212 | C | T | No |
| 741 | D04 | 54749560 | G | T | No |
| 742 | D04 | 55088982 | T | G | No |
| 743 | D04 | 6405687 | C | T | No |
| 744 | D04 | 9885360 | G | C | No |
| 745 | D05 | 10111963 | A | G | No |
| 746 | D05 | 22301632 | T | C | No |
| 747 | D05 | 22581979 | C | A | No |
| 748 | D05 | 44163822 | C | G | No |
| 749 | D05 | 4754359 | G | A | No |
| 750 | D05 | 50425541 | G | A | No |
| 751 | D05 | 54319989 | C | T | No |
| 752 | D05 | 54328389 | G | A | No |
| 753 | D05 | 60809038 | C | G | No |
| 754 | D05 | 63575099 | G | A | No |
| 755 | D06 | 120461 | T | C | No |
| 756 | D06 | 15573192 | C | A | No |
| 757 | D06 | 24091586 | T | G | No |
| 758 | D06 | 32611737 | T | C | No |
| 759 | D06 | 37123528 | A | G | No |
| 760 | D06 | 39543027 | T | C | No |
| 761 | D06 | 40371530 | A | C | No |
| 762 | D06 | 40976675 | T | G | No |
| 763 | D06 | 4587872 | A | G | No |
| 764 | D06 | 459987 | A | G | No |
| 765 | D06 | 46781842 | A | G | No |
| 766 | D06 | 51896336 | G | A | No |
| 767 | D06 | 52879640 | A | G | No |
| 768 | D06 | 8300282 | C | A | No |
| 769 | D06 | 8301102 | A | G | No |

TABLE 1-continued

Information of 894 core SNP loci

| SNP number | Chromosome | Genome position | Ref | Alt | Whether it is a functional locus |
|---|---|---|---|---|---|
| 770 | D06 | 8302085 | A | T | No |
| 771 | D06 | 8316146 | C | G | No |
| 772 | D06 | 8316953 | A | G | No |
| 773 | D06 | 8317874 | T | G | No |
| 774 | D06 | 9134552 | G | A | No |
| 775 | D06 | 984077 | G | C | No |
| 776 | D07 | 12186527 | T | A | No |
| 777 | D07 | 18817779 | C | T | No |
| 778 | D07 | 19736648 | A | T | No |
| 779 | D07 | 21947521 | T | C | No |
| 780 | D07 | 23120977 | A | G | No |
| 781 | D07 | 28055711 | G | A | No |
| 782 | D07 | 29109329 | C | A | No |
| 783 | D07 | 29307287 | C | A | No |
| 784 | D07 | 31304191 | T | A | No |
| 785 | D07 | 33903373 | A | G | No |
| 786 | D07 | 35288441 | A | C | No |
| 787 | D07 | 35472043 | G | A | No |
| 788 | D07 | 42317367 | A | G | No |
| 789 | D07 | 48374078 | C | T | No |
| 790 | D07 | 4924881 | T | A | No |
| 791 | D07 | 53499692 | T | C | No |
| 792 | D08 | 10680089 | C | G | No |
| 793 | D08 | 13077583 | T | C | No |
| 794 | D08 | 149324 | C | T | No |
| 795 | D08 | 16413758 | T | A | No |
| 796 | D08 | 1767573 | C | T | No |
| 797 | D08 | 18913124 | T | C | No |
| 798 | D08 | 21560032 | C | T | No |
| 799 | D08 | 22149204 | C | A | No |
| 800 | D08 | 23067189 | T | C | No |
| 801 | D08 | 23093384 | C | A | No |
| 802 | D08 | 31945553 | A | G | No |
| 803 | D08 | 4830232 | G | T | No |
| 804 | D08 | 53958299 | A | G | No |
| 805 | D08 | 54171228 | C | T | No |
| 806 | D08 | 60184589 | T | A | No |
| 807 | D08 | 60980269 | T | G | No |
| 808 | D08 | 64419820 | T | C | No |
| 809 | D08 | 69065625 | C | T | No |
| 810 | D09 | 11775224 | T | C | No |
| 811 | D09 | 13077530 | G | A | No |
| 812 | D09 | 13092466 | G | A | No |
| 813 | D09 | 14556836 | A | G | No |
| 814 | D09 | 14980165 | T | C | No |
| 815 | D09 | 16586783 | G | A | No |
| 816 | D09 | 16915286 | T | G | No |
| 817 | D09 | 29378213 | T | C | No |
| 818 | D09 | 30116231 | T | C | No |
| 819 | D09 | 32511822 | A | G | No |
| 820 | D09 | 35843751 | T | A | No |
| 821 | D09 | 39952298 | A | G | No |
| 822 | D09 | 40931477 | T | G | No |
| 823 | D09 | 5153702 | A | G | No |
| 824 | D09 | 5327090 | A | T | No |
| 825 | D09 | 7625892 | A | G | No |
| 826 | D09 | 8984707 | T | C | No |
| 827 | D10 | 11881833 | G | A | No |
| 828 | D10 | 12641518 | T | C | No |
| 829 | D10 | 13203079 | T | C | No |
| 830 | D10 | 13218360 | A | G | No |
| 831 | D10 | 17236139 | A | C | No |
| 832 | D10 | 21015217 | A | T | No |
| 833 | D10 | 22279984 | T | C | No |
| 834 | D10 | 23857566 | T | C | No |
| 835 | D10 | 27931417 | A | C | No |
| 836 | D10 | 29136434 | A | G | No |
| 837 | D10 | 36608001 | A | G | No |
| 838 | D10 | 5768028 | T | A | No |
| 839 | D10 | 58648569 | T | C | No |
| 840 | D10 | 59110528 | C | T | No |
| 841 | D10 | 59338863 | A | G | No |
| 842 | D10 | 63020858 | A | G | No |

TABLE 1-continued

Information of 894 core SNP loci

| SNP number | Chromosome | Genome position | Ref | Alt | Whether it is a functional locus |
|---|---|---|---|---|---|
| 843 | D10 | 65084524 | C | T | No |
| 844 | D10 | 7921537 | G | C | No |
| 845 | D10 | 9584269 | C | T | No |
| 846 | D11 | 18266384 | A | G | No |
| 847 | D11 | 19526253 | A | G | No |
| 848 | D11 | 21313603 | T | C | No |
| 849 | D11 | 22813334 | G | C | No |
| 850 | D11 | 22866559 | G | A | No |
| 851 | D11 | 22965595 | T | C | No |
| 852 | D11 | 25045105 | A | G | No |
| 853 | D11 | 26242153 | A | G | No |
| 854 | D11 | 29069201 | A | G | No |
| 855 | D11 | 30858636 | A | G | No |
| 856 | D11 | 31530446 | T | C | No |
| 857 | D11 | 33562213 | G | T | No |
| 858 | D11 | 36259888 | G | C | No |
| 859 | D11 | 4001453 | C | A | No |
| 860 | D11 | 42064410 | C | G | No |
| 861 | D11 | 46502666 | T | C | No |
| 862 | D11 | 49025870 | T | G | No |
| 863 | D11 | 53984557 | A | G | No |
| 864 | D11 | 62552126 | C | T | No |
| 865 | D11 | 63105221 | T | A | No |
| 866 | D12 | 13234020 | C | A | No |
| 867 | D12 | 20303021 | T | G | No |
| 868 | D12 | 20676817 | C | T | No |
| 869 | D12 | 20679556 | G | C | No |
| 870 | D12 | 24086625 | G | A | No |
| 871 | D12 | 31095105 | A | G | No |
| 872 | D12 | 31344122 | G | A | No |
| 873 | D12 | 34101393 | A | G | No |
| 874 | D12 | 36771208 | C | T | No |
| 875 | D12 | 39681819 | T | G | No |
| 876 | D12 | 39682436 | C | T | No |
| 877 | D12 | 40027143 | A | G | No |
| 878 | D12 | 41909287 | A | G | No |
| 879 | D12 | 4257295 | A | G | No |
| 880 | D12 | 4544167 | A | C | No |
| 881 | D12 | 50612739 | T | C | No |
| 882 | D13 | 19377974 | A | G | No |
| 883 | D13 | 2694968 | A | C | No |
| 884 | D13 | 3134551 | A | T | No |
| 885 | D13 | 39085839 | G | A | No |
| 886 | D13 | 42257012 | A | G | No |
| 887 | D13 | 49441679 | A | G | No |
| 888 | D13 | 49745988 | A | G | No |
| 889 | D13 | 55874078 | A | G | No |
| 890 | D13 | 57525048 | T | G | No |
| 891 | D13 | 58479149 | A | G | No |
| 892 | D13 | 63605335 | A | G | No |
| 893 | D13 | 64125386 | T | C | No |
| 894 | D13 | 9724970 | T | A | No |

Where, Ref represents the base type of a SNP locus in the reference genome, and Alt represents the base type of SNP locus in a population.

Example 2: Use of Low-Density Liquid-Phase Chip for *Gossypium hirsutum* L. Based on Targeted Capture Sequencing in Genotyping and Detection of Transgenic Components of *Gossypium hirsutum* L.

200 *Gossypium hirsutum* L. varieties were used to test the chip. The test results showed that the average locus detection rate of cotton functional marker chip was 94.17%, which met the genotyping test of *Gossypium hirsutum* L.

The whole experimental process was based on the GenoBaits technical system. The specific experimental process is as follows:

1. The genomic DNAs of samples to be tested were extracted, and a sample library was constructed;

1.1 DNA Extraction of the Samples

The DNA of the sample was extracted by a CTAB method.

1.2 DNA Quality Inspection of the Samples

The DNA concentration of the test sample was measured by Qubit Fluorometric Quantitation (Thermofisher), and the integrity of the DNA was detected by 1 wt % agarose gel electrophoresis (AGE). The qualified samples were put into a refrigerator at 4° C. for storage and standby.

1.3 DNA Fragmentation of the Sample

12 µL of the qualified DNA was placed in a 0.2 µL PCR tube, the tube was placed in an ultrasonic crusher to randomly physically crush the DNA, with the fragment being crushed to 200-400 bp.

1.4 End Repair of the Samples

4 µL of GenoBaits End Repair Buffer (genobaits, Shijiazhuang MOLBREEDING Biotechnology Co., Ltd.) and 2.7 µL of GenoBaits End Repair Enzyme were added into the tube, and water was replenished to 20 µL; the tube was put into an ABI 9700 PCR instrument for incubation for 20 minutes at 37° C. to complete the end repair and A addition process of the crushed fragments.

1.5 Sequencing Adapter Ligation of the Samples

The small tube was taken from the PCR instrument, 2 µL of GenoBaits Ultra DNA ligase, 8 µL of gGenoBaits Ultra DNA Ligase Buffer and 2 µL of GenoBaits Adapter were added into the tube, and water was replenished to 40 µL; then the tube was put on the ABI9700 PCR instrument for reaction for 30 minutes at 22° C. to complete the ligation of sequencing adapters.

1.6 DNA Purification of the Samples

48 µL of Beackman AMPure XP Beads (Beackman Company) was added to the ligation products for purification. After purification, magnetic beads were used for fragment screening, and the ligation products with inserted fragments of 200-300 bp were retained.

1.7 Library Amplification of the Samples

5 µL of a sequencing adapter with a Barcode sequence, 1 µL of a P5 adapter and 10 µL of GenoBaits PCR Master Mix were added into the PCR tube in the previous step, and pure water was replenished to 20 µL; amplification was carried out by ABI 9700 PCR instrument; the amplification procedures were: pre-denaturation at 95° C. for 5 minutes, denaturation at 95° C. for 30 seconds, annealing at 60° C. for 30 seconds, and extension at 72° C. for 30 seconds; denaturation, annealing and extension were repeated for a total of 8 cycles; extension at 72° C. for 5 min. Different Barcodes were used to distinguish different samples.

1.8 Library Purification of the Samples

24 µL of Beckmen AMPure XP Beads (Beackman Company) was added to the second round of the PCR product, which was then sucked up and down with a pipette for evenness; 0.2 µL of the PCR tube was placed on a magnetic rack until the solution was clear, the supernatant was discarded and the magnetic beads were washed once with 75 vol % ethanol; and the library DNA was eluted with Tris-HCl with pH value of 8.0.

2. The genotypes of the 894 SNP loci and 14 genes of the target samples were determined by the Low-density liquid-phase chip for *Gossypium hirsutum* L. based on targeted capture sequencing.

2.1 DNA Hybridization 500 ng of the constructed genomic DNA sequencing library was taken, into which 5 µL of GenoBaits Block I and 2 µL of GenoBaits Block II were added; it was then put on an Eppendorf Concentrator plus (Eppendorf Company) vacuum concentrator, and evaporated to dry powder at ≤70° C.; 8.5 µL of GenoBaits 2×Hyb Buffer, 2.7 µL of GenoBaits Hyb Buffer Enhancer and 2.8 µL of Nuclease-Free Water were added into the dry powder tube; the mixture was sucked and mixed evenly with a pipette, and then put on an ABI 9700 PCR instrument for incubation at 95° C. for 10 minutes; subsequently the PCR tube was taken out, and 3 µL of the synthesized probe (the concentration of the probe was 60 ng/µL) was added into the PCR tube; the mixture was subjected to vortex shaking to be mixed evenly; and then the PCR tube was put on ABI 9700 PCR instrument for incubation at 65° C. for 2 hours to complete the probe hybridization reaction.

2.2 DNA Capture

100 µL of GenoBaits DNA Probe Beads was added to the reaction system completed in the previous step, followed by sucking up and down for 10 times; the reaction system was then put in ABI 9700 PCR instrument for incubation at 65° C. for 45 minutes to bind the magnetic beads to the probe. 100 µL of GenoBaits Wash Buffer I and 150 µL of GenoBaits Wash BufferII were respectively used to hot-wash the magnetic beads bound with the probe at 65° C., and then 100 µL of GenoBaits Wash Buffer I, 150 µL of GenoBaits Wash Buffer II (and 150 µL of GenoBaits Wash Buffer III) were respectively used to wash the magnetic beads at room temperature. The washed magnetic beads were resuspended with 20 µL of Nuclease-Free Water.

13 µL of resuspended DNA (with magnetic beads) was added into a new 0.2 mL PCR tube, then 15 µL of GenoBaits PCR Master Mix and 2 µL of GenoBaits Primer Mix to configure a post-PCR system; the library was amplified with ABI 9700 PCR instrument. The amplification procedures were: pre-denaturation at 95° C. for 5 minutes, denaturation at 95° C. for 30 seconds, annealing at 60° C. for 30 seconds, and extension at 72° C. for 30 seconds; denaturation, annealing and extension were repeated for a total of 15 cycles; extension at 72° C. for 5 min.

45 µL of Beck Menam Pure XP Beads (Beackman Company) was added to the post-PCR product, followed by sucking up and down for evenness with a pipette; then the 0.2 mL PCR tube was placed on a magnetic rack until the solution was clear; the supernatant was discarded and the magnetic beads were washed twice with 75 vol % ethanol, and the library DNA were eluted with Tris-HCl with pH of 8.0. The hybridization capture of the probe was completed.

2.3 DNA Hybridization Capture Library Quality Inspection

The DNA concentration of the library was measured by Qubit Fluorometric Quantitation (Thermo Fisher), and then the fragment size of the library DNA was detected by agarose gel electrophoresis to determine whether it was between 300 to 400 bp.

2.4 DNA Hybridization Capture Library Sequencing

The constructed DNA library was sequenced by a Huada MGISEQ2000 sequencer.

2.5 Genotype Data Analysis

After quality data control of sequencing by FastQC (www.bioinformatics.babraham.ac.uk/project), the default parameters of BWA (bio-bwa.sourceforge.net) were used to compare the sequencing data to the reference genome. SNP identification for sequencing data were carried out by GATK (software.broadinstitute.org/gatk) software, and genotyping information of probe capture sequencing was extracted by self-compiled Perl script to form the final genotyping results, as shown in Table 2 and Table 3.

TABLE 2

Detection rate of low-density liquid-phase gene chip in 200 cotton varieties

| No. | Locus type | Number of missing loci | Number of detected loci | Detection rate of loci | Total number of loci | Number of sequences | Sample name |
|---|---|---|---|---|---|---|---|
| W4_23 | SNP | 31 | 863 | 0.965324 | 894 | 100249200 | Yu cotton 20 |
| W5_53 | SNP | 31 | 863 | 0.965324 | 894 | 99342600 | Y13 |
| W6_12 | SNP | 33 | 861 | 0.963087 | 894 | 99011100 | Shixuan 87*SGK321 |
| W6_20 | SNP | 33 | 861 | 0.963087 | 894 | 99988800 | 53--12 |
| W4_12 | SNP | 34 | 860 | 0.961969 | 894 | 99629100 | Xinluzao No. 25 |
| W6_2 | SNP | 35 | 859 | 0.96085 | 894 | 100976700 | Ken 62*HT23 |
| W7_41 | SNP | 35 | 859 | 0.96085 | 894 | 99422400 | 12-12-29 |
| W4_24 | SNP | 38 | 856 | 0.957494 | 894 | 100787400 | Xu cotton 18 |
| W7_51 | SNP | 38 | 856 | 0.957494 | 894 | 100119900 | 12-5-66 |
| W8_55 | SNP | 39 | 855 | 0.956376 | 894 | 99564300 | DP201 |
| W7_22 | SNP | 40 | 854 | 0.955257 | 894 | 100554900 | 25-27 |
| W4_26 | SNP | 41 | 853 | 0.954139 | 894 | 100237200 | Xinluzao No. 18 |
| W7_34 | SNP | 41 | 853 | 0.954139 | 894 | 100266000 | Dun cotton No. 1 |
| W7_52 | SNP | 41 | 853 | 0.954139 | 894 | 99038400 | 12-5-62 |
| W5_50 | SNP | 42 | 852 | 0.95302 | 894 | 100182300 | 111-43-50 |
| W5_56 | SNP | 42 | 852 | 0.95302 | 894 | 99903900 | Shi K14 |
| W6_45 | SNP | 42 | 852 | 0.95302 | 894 | 99362700 | Fuquan No. 10 |
| W6_57 | SNP | 42 | 852 | 0.95302 | 894 | 100907100 | Shikang 126 |
| W7_32 | SNP | 42 | 852 | 0.95302 | 894 | 100285200 | Jin 3 |
| W4_19 | SNP | 43 | 851 | 0.951902 | 894 | 100998300 | Yu cotton 112 |
| W6_47 | SNP | 43 | 851 | 0.951902 | 894 | 100189200 | Henan kanghuang |
| W7_43 | SNP | 43 | 851 | 0.951902 | 894 | 100931100 | 12-10-91 |
| W5_41 | SNP | 44 | 850 | 0.950783 | 894 | 99323400 | Nantong No. 5 |
| W6_14 | SNP | 44 | 850 | 0.950783 | 894 | 100806000 | 26-5*603 |
| W6_29 | SNP | 44 | 850 | 0.950783 | 894 | 99386400 | N78 |
| W6_38 | SNP | 44 | 850 | 0.950783 | 894 | 100534200 | ND012 |
| W7_55 | SNP | 44 | 850 | 0.950783 | 894 | 100782300 | 12-5-47 |
| W8_40 | SNP | 44 | 850 | 0.950783 | 894 | 99412800 | 15-23-52 |
| W8_53 | SNP | 44 | 850 | 0.950783 | 894 | 99927600 | 602 |
| W6_31 | SNP | 45 | 849 | 0.949664 | 894 | 99343500 | SW1 |
| W6_46 | SNP | 45 | 849 | 0.949664 | 894 | 100151700 | Haigan cotton |
| W8_21 | SNP | 45 | 849 | 0.949664 | 894 | 100318500 | 15-32-66 |
| W4_21 | SNP | 46 | 848 | 0.948546 | 894 | 100013100 | Xinluzao No. 35 |
| W5_57 | SNP | 46 | 848 | 0.948546 | 894 | 99984300 | 148-39 |
| W6_32 | SNP | 46 | 848 | 0.948546 | 894 | 100779900 | TH25 |
| W7_26 | SNP | 46 | 848 | 0.948546 | 894 | 100933800 | Han cotton 885 |
| W7_54 | SNP | 46 | 848 | 0.948546 | 894 | 99124200 | 12-5-50 |
| W8_29 | SNP | 46 | 848 | 0.948546 | 894 | 99807000 | 15-30-87 |
| W8_41 | SNP | 46 | 848 | 0.948546 | 894 | 100498500 | 15-23-2 |
| W4_10 | SNP | 47 | 847 | 0.947427 | 894 | 100618800 | Yu 79-10 |
| W4_11 | SNP | 47 | 847 | 0.947427 | 894 | 99957600 | Xinluzao No. 38 |
| W6_1 | SNP | 47 | 847 | 0.947427 | 894 | 99529800 | 19-34 |
| W6_33 | SNP | 47 | 847 | 0.947427 | 894 | 100663500 | Y17 |
| W6_52 | SNP | 47 | 847 | 0.947427 | 894 | 99811200 | Ji cotton 169 |
| W6_9 | SNP | 47 | 847 | 0.947427 | 894 | 99948900 | GK26* Xi 9 |
| W8_14 | SNP | 47 | 847 | 0.947427 | 894 | 99806400 | 15-49-128 |
| W8_3 | SNP | 47 | 847 | 0.947427 | 894 | 99324300 | 12-3-91 |
| W8_4 | SNP | 47 | 847 | 0.947427 | 894 | 100275300 | 12-3-79 |
| W4_15 | SNP | 48 | 846 | 0.946309 | 894 | 100711200 | Yan cotton No. 1 |
| W7_12 | SNP | 48 | 846 | 0.946309 | 894 | 99058800 | Huiyuan 14 |
| W7_35 | SNP | 48 | 846 | 0.946309 | 894 | 100970100 | Dezi cotton 531 |
| W7_49 | SNP | 48 | 846 | 0.946309 | 894 | 99326700 | 12-7-60 |
| W7_50 | SNP | 48 | 846 | 0.946309 | 894 | 99306900 | 12-7-59 |
| W7_7 | SNP | 48 | 846 | 0.946309 | 894 | 99368400 | Xinluzao No. 62 |
| W8_46 | SNP | 48 | 846 | 0.946309 | 894 | 100236300 | 15-22-119 |
| W4_20 | SNP | 49 | 845 | 0.94519 | 894 | 100209900 | Xuzhou 514 |
| W4_22 | SNP | 49 | 845 | 0.94519 | 894 | 100844100 | Qiannong 465 |
| W4_27 | SNP | 49 | 845 | 0.94519 | 894 | 100599600 | Xuzhou 58 |
| W5_49 | SNP | 49 | 845 | 0.94519 | 894 | 100093800 | 562*GK15 |
| W6_26 | SNP | 49 | 845 | 0.94519 | 894 | 100599900 | H65 |
| W6_56 | SNP | 49 | 845 | 0.94519 | 894 | 99428400 | Shi K10 |
| W7_17 | SNP | 49 | 845 | 0.94519 | 894 | 100983000 | K2725 |
| W7_18 | SNP | 49 | 845 | 0.94519 | 894 | 99957300 | Han 2301 |
| W7_25 | SNP | 49 | 845 | 0.94519 | 894 | 99270000 | Keke 1543 |
| W7_27 | SNP | 49 | 845 | 0.94519 | 894 | 99344400 | Kezi cotton 100 |
| W8_1 | SNP | 49 | 845 | 0.94519 | 894 | 99020100 | 12-4-4 |
| W8_9 | SNP | 49 | 845 | 0.94519 | 894 | 99031500 | 12-2-1 |
| W4_13 | SNP | 50 | 844 | 0.944072 | 894 | 99059400 | Lumianyan 32 |
| W4_18 | SNP | 50 | 844 | 0.944072 | 894 | 100920900 | Shu cotton No. 1 |
| W5_40 | SNP | 50 | 844 | 0.944072 | 894 | 99094200 | Zhongmiansuo 2 |
| W5_43 | SNP | 50 | 844 | 0.944072 | 894 | 99566100 | Su cotton No. 9 |
| W6_19 | SNP | 50 | 844 | 0.944072 | 894 | 99018000 | 9456D |
| W6_25 | SNP | 50 | 844 | 0.944072 | 894 | 99556800 | GK19 |

TABLE 2-continued

Detection rate of low-density liquid-phase gene chip in 200 cotton varieties

| No. | Locus type | Number of missing loci | Number of detected loci | Detection rate of loci | Total number of loci | Number of sequences | Sample name |
|---|---|---|---|---|---|---|---|
| W6_4 | SNP | 50 | 844 | 0.944072 | 894 | 99815400 | 9-8*41-79 |
| W6_5 | SNP | 50 | 844 | 0.944072 | 894 | 100613700 | 29-24 |
| W6_8 | SNP | 50 | 844 | 0.944072 | 894 | 99734700 | 2040048 |
| W7_13 | SNP | 50 | 844 | 0.944072 | 894 | 99374700 | Xinluzhong No. 42 |
| W7_2 | SNP | 50 | 844 | 0.944072 | 894 | 99099900 | Xinshixuan 12-2 |
| W7_31 | SNP | 50 | 844 | 0.944072 | 894 | 100951200 | Gan cotton 47 |
| W7_44 | SNP | 50 | 844 | 0.944072 | 894 | 100114500 | 12-10-55 |
| W8_28 | SNP | 50 | 844 | 0.944072 | 894 | 100653600 | 15-30-114 |
| W8_45 | SNP | 50 | 844 | 0.944072 | 894 | 100893600 | 15-22-122 |
| W5_51 | SNP | 51 | 843 | 0.942953 | 894 | 100363500 | Yahuang |
| W6_16 | SNP | 51 | 843 | 0.942953 | 894 | 99083400 | 86-27 |
| W6_23 | SNP | 51 | 843 | 0.942953 | 894 | 100297200 | FY408 |
| W7_59 | SNP | 51 | 843 | 0.942953 | 894 | 99893700 | 12-4-17 |
| W7_8 | SNP | 51 | 843 | 0.942953 | 894 | 100942800 | Hongye cotton |
| W8_15 | SNP | 51 | 843 | 0.942953 | 894 | 100924800 | 15-49-81 |
| W5_42 | SNP | 52 | 842 | 0.941834 | 894 | 100995300 | Jing 1246 |
| W6_21 | SNP | 52 | 842 | 0.941834 | 894 | 100983000 | Huiyuan 706 |
| W6_34 | SNP | 52 | 842 | 0.941834 | 894 | 99177600 | Xinshi H8 |
| W6_53 | SNP | 52 | 842 | 0.941834 | 894 | 99472200 | Jinhui No. 2 |
| W6_59 | SNP | 52 | 842 | 0.941834 | 894 | 99576000 | Xi 9 |
| W7_19 | SNP | 52 | 842 | 0.941834 | 894 | 99485100 | Zhongchuang 83 |
| W7_28 | SNP | 52 | 842 | 0.941834 | 894 | 99802500 | Guangyedaizi cotton |
| W7_29 | SNP | 52 | 842 | 0.941834 | 894 | 100461300 | Guannong No. 1 |
| W7_33 | SNP | 52 | 842 | 0.941834 | 894 | 100824600 | Ji cotton 25 |
| W7_37 | SNP | 52 | 842 | 0.941834 | 894 | 100739700 | Liao cotton No. 6 |
| W7_5 | SNP | 52 | 842 | 0.941834 | 894 | 100159500 | FY11 |
| W8_20 | SNP | 52 | 842 | 0.941834 | 894 | 100125300 | 15-34-37 |
| W8_27 | SNP | 52 | 842 | 0.941834 | 894 | 100520100 | 15-31-37 |
| W4_16 | SNP | 53 | 841 | 0.940716 | 894 | 99840300 | Xinluzao No. 37 |
| W4_25 | SNP | 53 | 841 | 0.940716 | 894 | 99889800 | Xinluzao No.34 |
| W5_46 | SNP | 53 | 841 | 0.940716 | 894 | 99389100 | 10-75(GK26) |
| W6_17 | SNP | 53 | 841 | 0.940716 | 894 | 99564000 | 44-32*0317 |
| W6_18 | SNP | 53 | 841 | 0.940716 | 894 | 100725000 | 907 |
| W6_30 | SNP | 53 | 841 | 0.940716 | 894 | 99855300 | Sic74 |
| W6_37 | SNP | 53 | 841 | 0.940716 | 894 | 99430800 | TH1246 |
| W7_16 | SNP | 53 | 841 | 0.940716 | 894 | 99008700 | Xinshi K25 |
| W7_21 | SNP | 53 | 841 | 0.940716 | 894 | 100089600 | Kelin 113 |
| W7_38 | SNP | 53 | 841 | 0.940716 | 894 | 99726900 | 9D208 |
| W8_23 | SNP | 53 | 841 | 0.940716 | 894 | 100993800 | 15-32-56 |
| W8_44 | SNP | 53 | 841 | 0.940716 | 894 | 100825200 | 15-22-123 |
| W5_44 | SNP | 54 | 840 | 0.939597 | 894 | 100837200 | 604 |
| W5_45 | SNP | 54 | 840 | 0.939597 | 894 | 100416000 | Shi K9*69-2 |
| W6_15 | SNP | 54 | 840 | 0.939597 | 894 | 100869000 | 78-12*27-67 |
| W7_58 | SNP | 54 | 840 | 0.939597 | 894 | 99997500 | 12-4-18 |
| W4_14 | SNP | 55 | 839 | 0.938479 | 894 | 100904400 | Yuwu 19 |
| W6_36 | SNP | 55 | 839 | 0.938479 | 894 | 100311900 | Z1112 |
| W7_20 | SNP | 55 | 839 | 0.938479 | 894 | 99243300 | Hexin 3-15 |
| W7_3 | SNP | 55 | 839 | 0.938479 | 894 | 100638300 | Yizao cotton No. 1 |
| W7_46 | SNP | 55 | 839 | 0.938479 | 894 | 99991800 | 12-7-63 |
| W8_16 | SNP | 55 | 839 | 0.938479 | 894 | 99406200 | 15-49-52 |
| W8_22 | SNP | 55 | 839 | 0.938479 | 894 | 99472200 | 15-32-58 |
| W8_35 | SNP | 55 | 839 | 0.938479 | 894 | 100480200 | 15-24-43 |
| W8_43 | SNP | 55 | 839 | 0.938479 | 894 | 99589500 | 15-22-138 |
| W8_51 | SNP | 55 | 839 | 0.938479 | 894 | 100058700 | 15-20-77 |
| W4_28 | SNP | 56 | 838 | 0.93736 | 894 | 99112500 | Xinqiu No. 4 |
| W6_11 | SNP | 56 | 838 | 0.93736 | 894 | 100515300 | 69--2 |
| W6_54 | SNP | 56 | 838 | 0.93736 | 894 | 100317000 | Liao cotton 18 |
| W7_14 | SNP | 56 | 838 | 0.93736 | 894 | 99093900 | B4-23 |
| W7_48 | SNP | 56 | 838 | 0.93736 | 894 | 99941700 | 12-7-61 |
| W8_8 | SNP | 56 | 838 | 0.93736 | 894 | 99772200 | 12-2-3 |
| W5_52 | SNP | 57 | 837 | 0.936242 | 894 | 100220400 | 116-39 Li |
| W5_55 | SNP | 57 | 837 | 0.936242 | 894 | 100485300 | Fengkai 2002 |
| W6_13 | SNP | 57 | 837 | 0.936242 | 894 | 99657600 | 69-2*68-38*44-5 |
| W6_55 | SNP | 57 | 837 | 0.936242 | 894 | 100733100 | Nongda 06-2 |
| W6_60 | SNP | 57 | 837 | 0.936242 | 894 | 99150900 | Xinken 09 |
| W8_12 | SNP | 57 | 837 | 0.936242 | 894 | 99462000 | 15-50-26 |
| W6_42 | SNP | 58 | 836 | 0.935123 | 894 | 100928700 | ZJ6 |
| W8_11 | SNP | 58 | 836 | 0.935123 | 894 | 100039800 | 12-1-41 |
| W8_32 | SNP | 58 | 836 | 0.935123 | 894 | 99022500 | 15-26-117 |
| W8_33 | SNP | 58 | 836 | 0.935123 | 894 | 99439800 | 15-26-115 |
| W5_47 | SNP | 59 | 835 | 0.934004 | 894 | 100508700 | Ken 4432*42-53 |
| W7_15 | SNP | 59 | 835 | 0.934004 | 894 | 99036900 | Dexia cotton No. 1 |
| W7_6 | SNP | 59 | 835 | 0.934004 | 894 | 100377900 | ZB0848 |

TABLE 2-continued

Detection rate of low-density liquid-phase gene chip in 200 cotton varieties

| No. | Locus type | Number of missing loci | Number of detected loci | Detection rate of loci | Total number of loci | Number of sequences | Sample name |
|---|---|---|---|---|---|---|---|
| W8_13 | SNP | 59 | 835 | 0.934004 | 894 | 100167300 | 15-50-24 |
| W8_6 | SNP | 59 | 835 | 0.934004 | 894 | 100583400 | 12-2-62 |
| W8_7 | SNP | 59 | 835 | 0.934004 | 894 | 99838800 | 12-2-43 |
| W5_54 | SNP | 60 | 834 | 0.932886 | 894 | 100389900 | 148-39*06X2 |
| W6_24 | SNP | 60 | 834 | 0.932886 | 894 | 100596600 | G2-2-5 |
| W6_3 | SNP | 60 | 834 | 0.932886 | 894 | 100425600 | (ZJ6*112-17)BC3 |
| W6_48 | SNP | 60 | 834 | 0.932886 | 894 | 99048000 | Huihe No. 28 ? |
| W6_7 | SNP | 60 | 834 | 0.932886 | 894 | 99922800 | 52-64*42-53K |
| W7_36 | SNP | 60 | 834 | 0.932886 | 894 | 100682400 | Ji cotton No. 1 |
| W7_42 | SNP | 60 | 834 | 0.932886 | 894 | 100202400 | 12-12-25 |
| W8_19 | SNP | 60 | 834 | 0.932886 | 894 | 100493400 | 15-34-38 |
| W6_28 | SNP | 61 | 833 | 0.931767 | 894 | 99491100 | JF-2 |
| W7_53 | SNP | 61 | 833 | 0.931767 | 894 | 99729900 | 12-5-61 |
| W5_58 | SNP | 62 | 832 | 0.930649 | 894 | 100466100 | 15-10 |
| W7_11 | SNP | 62 | 832 | 0.930649 | 894 | 100858500 | Huiyuan 12 |
| W7_47 | SNP | 62 | 832 | 0.930649 | 894 | 99605700 | 12-7-62 |
| W8_2 | SNP | 62 | 832 | 0.930649 | 894 | 99890100 | 12-3-100 |
| W8_34 | SNP | 62 | 832 | 0.930649 | 894 | 100190700 | 15-24-74 |
| W5_48 | SNP | 63 | 831 | 0.92953 | 894 | 99879600 | 41-79*Kang 10 |
| W6_40 | SNP | 63 | 831 | 0.92953 | 894 | 100251300 | C6-5-3-3 |
| W6_44 | SNP | 63 | 831 | 0.92953 | 894 | 100044000 | Bo 6 |
| W7_57 | SNP | 63 | 831 | 0.92953 | 894 | 100730100 | 12-4-65 |
| W8_10 | SNP | 63 | 831 | 0.92953 | 894 | 99693300 | 12-1-99 |
| W8_25 | SNP | 63 | 831 | 0.92953 | 894 | 99323700 | 15-31-127 |
| W8_5 | SNP | 63 | 831 | 0.92953 | 894 | 99361500 | 12-3-6 |
| W6_6 | SNP | 64 | 830 | 0.928412 | 894 | 99247500 | HY3(Yan) |
| W8_17 | SNP | 64 | 830 | 0.928412 | 894 | 99436200 | 15-48-27 |
| W8_26 | SNP | 64 | 830 | 0.928412 | 894 | 100524900 | 15-31-60 |
| W6_51 | SNP | 65 | 829 | 0.927293 | 894 | 100836000 | Huiyuan 720 |
| W7_10 | SNP | 65 | 829 | 0.927293 | 894 | 99849300 | Nongda cotton No. 8 |
| W7_60 | SNP | 65 | 829 | 0.927293 | 894 | 99119100 | 12-4-13 |
| W6_49 | SNP | 66 | 828 | 0.926174 | 894 | 100147800 | Xinluzao No. 61 |
| W8_24 | SNP | 66 | 828 | 0.926174 | 894 | 99160800 | 15-31-131 |
| W8_38 | SNP | 66 | 828 | 0.926174 | 894 | 99833100 | 15-23-71 |
| W8_54 | SNP | 66 | 828 | 0.926174 | 894 | 100014300 | 217 |
| W5_59 | SNP | 67 | 827 | 0.925056 | 894 | 100699200 | Huai cotton No. 2 |
| W6_10 | SNP | 67 | 827 | 0.925056 | 894 | 100195500 | C2 |
| W6_27 | SNP | 67 | 827 | 0.925056 | 894 | 99646800 | IF1-1K |
| W7_30 | SNP | 67 | 827 | 0.925056 | 894 | 99294000 | Jin cotton 29 |
| W6_22 | SNP | 68 | 826 | 0.923937 | 894 | 99210600 | Yan cotton 216 |
| W7_56 | SNP | 68 | 826 | 0.923937 | 894 | 99101400 | 12-4-94 |
| W8_52 | SNP | 68 | 826 | 0.923937 | 894 | 100813800 | Xinshi H 12 |
| W6_35 | SNP | 69 | 825 | 0.922819 | 894 | 100593900 | Tianyun 07195 |
| W6_43 | SNP | 69 | 825 | 0.922819 | 894 | 99564000 | Biaoda A parent |
| W8_30 | SNP | 70 | 824 | 0.9217 | 894 | 99070500 | 15-30-10 |
| W8_36 | SNP | 70 | 824 | 0.9217 | 894 | 99015300 | 15-24-42 |
| W7_4 | SNP | 71 | 823 | 0.920582 | 894 | 100414200 | Zhong 705 |
| W8_42 | SNP | 74 | 820 | 0.917226 | 894 | 99028800 | 15-23-1 |
| W7_9 | SNP | 75 | 819 | 0.916107 | 894 | 100838100 | 112-27 |
| W6_39 | SNP | 76 | 818 | 0.914989 | 894 | 99708300 | Jin ken 1242 |
| W8_37 | SNP | 78 | 816 | 0.912752 | 894 | 99621900 | 15-24-19 |
| W8_18 | SNP | 79 | 815 | 0.911633 | 894 | 99877200 | 15-37-106 |
| W8_50 | SNP | 80 | 814 | 0.910515 | 894 | 99403800 | 15-21-16 |
| W8_39 | SNP | 83 | 811 | 0.907159 | 894 | 99165900 | 15-23-68 |

TABLE 3

Detection of transgenic components in 200 cotton varieties by low-density liquid-phase gene chip

| Gene name | A1Bt | A2CPTI | A3CP4-epsps | A4CP4-epsps | A5bar | A6pat | A7CdP450 | A8cp4-epsps | B.1CaMV35S | B.2FMV35S | B.3NOS | B.4NOS | B.5CaMV35S | NPTII |
|---|---|---|---|---|---|---|---|---|---|---|---|---|---|---|
| Number of individuals detected | 64 | 0 | 0 | 3 | 0 | 0 | 0 | 0 | 68 | 3 | 0 | 54 | 0 | 64 |
| W4_10 | 0 | 0 | 0 | 0 | 0 | 0 | 0 | 0 | 0 | 0 | 0 | 0 | 0 | 0 |
| W4_11 | 0 | 0 | 0 | 0 | 0 | 0 | 0 | 0 | 0 | 0 | 0 | 0 | 0 | 0 |

TABLE 3-continued

Detection of transgenic components in 200 cotton varieties by low-density
liquid-phase gene chip

| Gene name | A1Bt | A2CPTI | A3CP4-epsps | A4CP4-epsps | A5bar | A6pat | A7CdP450 | A8cp4-epsps | B.1CaMV35S | B.2FMV35S | B.3NOS | B.4NOS | B.5CaMV35S | NPTII |
|---|---|---|---|---|---|---|---|---|---|---|---|---|---|---|
| W4_12 | 0 | 0 | 0 | 0 | 0 | 0 | 0 | 0 | 0 | 0 | 0 | 0 | 0 | 0 |
| W4_13 | 0 | 0 | 0 | 0 | 0 | 0 | 0 | 0 | 0 | 0 | 0 | 0 | 0 | 0 |
| W4_14 | 0 | 0 | 0 | 0 | 0 | 0 | 0 | 0 | 0 | 0 | 0 | 0 | 0 | 0 |
| W4_15 | 96.03% | 0 | 0 | 0 | 0 | 0 | 0 | 0 | 100.00% | 0 | 0 | 99.08% | 0 | 100.00% |
| W4_16 | 96.03% | 0 | 0 | 0 | 0 | 0 | 0 | 0 | 100.00% | 0 | 0 | 99.54% | 0 | 100.00% |
| W4_18 | 96.03% | 0 | 0 | 0 | 0 | 0 | 0 | 0 | 100.00% | 0 | 0 | 98.16% | 0 | 100.00% |
| W4_19 | 96.36% | 0 | 0 | 0 | 0 | 0 | 0 | 0 | 100.00% | 0 | 0 | 99.08% | 0 | 100.00% |
| W4_20 | 96.03% | 0 | 0 | 0 | 0 | 0 | 0 | 0 | 100.00% | 0 | 0 | 92.17% | 0 | 100.00% |
| W4_21 | 96.03% | 0 | 0 | 0 | 0 | 0 | 0 | 0 | 100.00% | 0 | 0 | 99.08% | 0 | 100.00% |
| W4_22 | 96.03% | 0 | 0 | 0 | 0 | 0 | 0 | 0 | 100.00% | 0 | 0 | 99.08% | 0 | 100.00% |
| W4_23 | 96.03% | 0 | 0 | 0 | 0 | 0 | 0 | 0 | 100.00% | 0 | 0 | 99.08% | 0 | 100.00% |
| W4_24 | 96.03% | 0 | 0 | 0 | 0 | 0 | 0 | 0 | 100.00% | 0 | 0 | 99.08% | 0 | 100.00% |
| W4_25 | 0 | 0 | 0 | 0 | 0 | 0 | 0 | 0 | 0 | 0 | 0 | 0 | 0 | 0 |
| W4_26 | 0 | 0 | 0 | 0 | 0 | 0 | 0 | 0 | 0 | 0 | 0 | 0 | 0 | 0 |
| W4_27 | 0 | 0 | 0 | 0 | 0 | 0 | 0 | 0 | 0 | 0 | 0 | 0 | 0 | 0 |
| W4_28 | 0 | 0 | 0 | 0 | 0 | 0 | 0 | 0 | 0 | 0 | 0 | 0 | 0 | 0 |
| W5_40 | 0 | 0 | 0 | 0 | 0 | 0 | 0 | 0 | 0 | 0 | 0 | 0 | 0 | 0 |
| W5_41 | 0 | 0 | 0 | 0 | 0 | 0 | 0 | 0 | 0 | 0 | 0 | 0 | 0 | 0 |
| W5_42 | 0 | 0 | 0 | 0 | 0 | 0 | 0 | 0 | 0 | 0 | 0 | 0 | 0 | 0 |
| W5_43 | 0 | 0 | 0 | 0 | 0 | 0 | 0 | 0 | 0 | 0 | 0 | 0 | 0 | 0 |
| W5_44 | 0 | 0 | 0 | 0 | 0 | 0 | 0 | 0 | 0 | 0 | 0 | 0 | 0 | 0 |
| W5_45 | 96.03% | 0 | 0 | 0 | 0 | 0 | 0 | 0 | 100.00% | 0 | 0 | 99.08% | 0 | 100.00% |
| W5_46 | 96.03% | 0 | 0 | 0 | 0 | 0 | 0 | 0 | 100.00% | 0 | 0 | 99.08% | 0 | 100.00% |
| W5_47 | 0 | 0 | 0 | 0 | 0 | 0 | 0 | 0 | 0 | 0 | 0 | 0 | 0 | 0 |
| W5_48 | 0 | 0 | 0 | 0 | 0 | 0 | 0 | 0 | 0 | 0 | 0 | 0 | 0 | 0 |
| W5_49 | 0 | 0 | 0 | 0 | 0 | 0 | 0 | 0 | 0 | 0 | 0 | 0 | 0 | 0 |
| W5_50 | 0 | 0 | 0 | 0 | 0 | 0 | 0 | 0 | 0 | 0 | 0 | 0 | 0 | 0 |
| W5_51 | 96.03% | 0 | 0 | 100.00% | 0 | 0 | 0 | 0 | 100.00% | 100.00% | 0 | 99.08% | 0 | 100.00% |
| W5_52 | 0 | 0 | 0 | 0 | 0 | 0 | 0 | 0 | 0 | 0 | 0 | 0 | 0 | 0 |
| W5_53 | 0 | 0 | 0 | 0 | 0 | 0 | 0 | 0 | 0 | 0 | 0 | 0 | 0 | 0 |
| W5_54 | 96.03% | 0 | 0 | 0 | 0 | 0 | 0 | 0 | 100.00% | 0 | 0 | 99.08% | 0 | 100.00% |
| W5_55 | 96.03% | 0 | 0 | 0 | 0 | 0 | 0 | 0 | 100.00% | 0 | 0 | 62.21% | 0 | 95.47% |
| W5_56 | 0 | 0 | 0 | 0 | 0 | 0 | 0 | 0 | 0 | 0 | 0 | 0 | 0 | 0 |
| W5_57 | 0 | 0 | 0 | 0 | 0 | 0 | 0 | 0 | 0 | 0 | 0 | 0 | 0 | 0 |
| W5_58 | 0 | 0 | 0 | 0 | 0 | 0 | 0 | 0 | 0 | 0 | 0 | 0 | 0 | 0 |
| W5_59 | 96.03% | 0 | 0 | 0 | 0 | 0 | 0 | 0 | 100.00% | 0 | 0 | 99.08% | 0 | 100.00% |
| W6_10 | 41.06% | 0 | 0 | 0 | 0 | 0 | 0 | 0 | 34.36% | 0 | 0 | 0 | 0 | 34.59% |
| W6_11 | 96.03% | 0 | 0 | 0 | 0 | 0 | 0 | 0 | 100.00% | 0 | 0 | 76.96% | 0 | 100.00% |
| W6_12 | 0 | 0 | 0 | 0 | 0 | 0 | 0 | 0 | 32.31% | 0 | 0 | 0 | 0 | 0 |
| W6_13 | 96.03% | 0 | 0 | 0 | 0 | 0 | 0 | 0 | 100.00% | 0 | 0 | 99.08% | 0 | 100.00% |
| W6_14 | 0 | 0 | 0 | 0 | 0 | 0 | 0 | 0 | 0 | 0 | 0 | 0 | 0 | 0 |
| W6_15 | 96.03% | 0 | 0 | 0 | 0 | 0 | 0 | 0 | 100.00% | 0 | 0 | 99.08% | 0 | 100.00% |
| W6_16 | 0 | 0 | 0 | 0 | 0 | 0 | 0 | 0 | 0 | 0 | 0 | 0 | 0 | 0 |
| W6_17 | 96.03% | 0 | 0 | 0 | 0 | 0 | 0 | 0 | 100.00% | 0 | 0 | 99.08% | 0 | 100.00% |
| W6_18 | 96.03% | 0 | 0 | 0 | 0 | 0 | 0 | 0 | 100.00% | 0 | 0 | 99.08% | 0 | 100.00% |
| W6_19 | 96.03% | 0 | 0 | 0 | 0 | 0 | 0 | 0 | 100.00% | 0 | 0 | 99.08% | 0 | 100.00% |
| W6_1 | 96.03% | 0 | 0 | 0 | 0 | 0 | 0 | 0 | 100.00% | 0 | 0 | 0 | 0 | 94.97% |
| W6_20 | 0 | 0 | 0 | 0 | 0 | 0 | 0 | 0 | 0 | 0 | 0 | 0 | 0 | 0 |
| W6_21 | 96.03% | 0 | 0 | 0 | 0 | 0 | 0 | 0 | 100.00% | 0 | 0 | 89.40% | 0 | 100.00% |
| W6_22 | 96.36% | 0 | 0 | 0 | 0 | 0 | 0 | 0 | 100.00% | 0 | 0 | 79.26% | 0 | 100.00% |
| W6_23 | 96.03% | 0 | 0 | 0 | 0 | 0 | 0 | 0 | 100.00% | 0 | 0 | 99.08% | 0 | 100.00% |
| W6_24 | 96.03% | 0 | 0 | 0 | 0 | 0 | 0 | 0 | 100.00% | 0 | 0 | 99.08% | 0 | 100.00% |
| W6_25 | 0 | 0 | 0 | 0 | 0 | 0 | 0 | 0 | 0 | 0 | 0 | 0 | 0 | 0 |
| W6_26 | 0 | 0 | 0 | 0 | 0 | 0 | 0 | 0 | 0 | 0 | 0 | 0 | 0 | 0 |
| W6_27 | 0 | 0 | 0 | 0 | 0 | 0 | 0 | 0 | 0 | 0 | 0 | 0 | 0 | 0 |
| W6_28 | 0 | 0 | 0 | 0 | 0 | 0 | 0 | 0 | 0 | 0 | 0 | 0 | 0 | 0 |
| W6_29 | 96.03% | 0 | 0 | 0 | 0 | 0 | 0 | 0 | 100.00% | 0 | 0 | 99.08% | 0 | 100.00% |
| W6_2 | 0 | 0 | 0 | 0 | 0 | 0 | 0 | 0 | 0 | 0 | 0 | 0 | 0 | 0 |
| W6_30 | 96.03% | 0 | 0 | 100.00% | 0 | 0 | 0 | 0 | 100.00% | 100.00% | 0 | 100.00% | 0 | 100.00% |
| W6_31 | 0 | 0 | 0 | 0 | 0 | 0 | 0 | 0 | 0 | 0 | 0 | 0 | 0 | 0 |
| W6_32 | 0 | 0 | 0 | 0 | 0 | 0 | 0 | 0 | 0 | 0 | 0 | 0 | 0 | 0 |
| W6_33 | 0 | 0 | 0 | 0 | 0 | 0 | 0 | 0 | 0 | 0 | 0 | 0 | 0 | 0 |
| W6_34 | 0 | 0 | 0 | 0 | 0 | 0 | 0 | 0 | 0 | 0 | 0 | 0 | 0 | 0 |
| W6_35 | 0 | 0 | 0 | 0 | 0 | 0 | 0 | 0 | 0 | 0 | 0 | 0 | 0 | 0 |
| W6_36 | 0 | 0 | 0 | 0 | 0 | 0 | 0 | 0 | 0 | 0 | 0 | 0 | 0 | 0 |
| W6_37 | 0 | 0 | 0 | 0 | 0 | 0 | 0 | 0 | 0 | 0 | 0 | 0 | 0 | 0 |
| W6_38 | 0 | 0 | 0 | 0 | 0 | 0 | 0 | 0 | 0 | 0 | 0 | 0 | 0 | 0 |
| W6_39 | 0 | 0 | 0 | 0 | 0 | 0 | 0 | 0 | 0 | 0 | 0 | 0 | 0 | 0 |
| W6_3 | 0 | 0 | 0 | 0 | 0 | 0 | 0 | 0 | 1.03% | 0 | 0 | 0 | 0 | 0 |
| W6_40 | 0 | 0 | 0 | 0 | 0 | 0 | 0 | 0 | 0 | 0 | 0 | 0 | 0 | 0 |
| W6_42 | 96.03% | 0 | 0 | 0 | 0 | 0 | 0 | 0 | 100.00% | 0 | 0 | 99.08% | 0 | 100.00% |
| W6_43 | 0 | 0 | 0 | 0 | 0 | 0 | 0 | 0 | 0 | 0 | 0 | 0 | 0 | 0 |
| W6_44 | 0 | 0 | 0 | 0 | 0 | 0 | 0 | 0 | 0 | 0 | 0 | 0 | 0 | 0 |
| W6_45 | 0 | 0 | 0 | 0 | 0 | 0 | 0 | 0 | 0 | 0 | 0 | 0 | 0 | 0 |

TABLE 3-continued

Detection of transgenic components in 200 cotton varieties by low-density
liquid-phase gene chip

| Gene name | A1Bt | A2CPTI | A3CP4-epsps | A4CP4-epsps | A5bar | A6pat | A7CdP450 | A8cp4-epsps | B.1CaMV35S | B.2FMV35S | B.3NOS | B.4NOS | B.5CaMV35S | NPTII |
|---|---|---|---|---|---|---|---|---|---|---|---|---|---|---|
| W6_46 | 96.03% | 0 | 0 | 100.00% | 0 | 0 | 0 | 0 | 100.00% | 100.00% | 0 | 99.54% | 0 | 100.00% |
| W6_47 | 0 | 0 | 0 | 0 | 0 | 0 | 0 | 0 | 0 | 0 | 0 | 0 | 0 | 0 |
| W6_48 | 0 | 0 | 0 | 0 | 0 | 0 | 0 | 0 | 0 | 0 | 0 | 0 | 0 | 0 |
| W6_49 | 0 | 0 | 0 | 0 | 0 | 0 | 0 | 0 | 0 | 0 | 0 | 0 | 0 | 0 |
| W6_4 | 96.03% | 0 | 0 | 0 | 0 | 0 | 0 | 0 | 100.00% | 0 | 0 | 96.31% | 0 | 100.00% |
| W6_51 | 96.03% | 0 | 0 | 0 | 0 | 0 | 0 | 0 | 100.00% | 0 | 0 | 70.97% | 0 | 100.00% |
| W6_52 | 0 | 0 | 0 | 0 | 0 | 0 | 0 | 0 | 0 | 0 | 0 | 0 | 0 | 0 |
| W6_53 | 0 | 0 | 0 | 0 | 0 | 0 | 0 | 0 | 0 | 0 | 0 | 0 | 0 | 0 |
| W6_54 | 96.03% | 0 | 0 | 0 | 0 | 0 | 0 | 0 | 100.00% | 0 | 0 | 99.08% | 0 | 100.00% |
| W6_55 | 0 | 0 | 0 | 0 | 0 | 0 | 0 | 0 | 0 | 0 | 0 | 0 | 0 | 0 |
| W6_56 | 0 | 0 | 0 | 0 | 0 | 0 | 0 | 0 | 44.10% | 0 | 0 | 0 | 0 | 0 |
| W6_57 | 96.03% | 0 | 0 | 0 | 0 | 0 | 0 | 0 | 100.00% | 0 | 0 | 99.08% | 0 | 100.00% |
| W6_59 | 0 | 0 | 0 | 0 | 0 | 0 | 0 | 0 | 0 | 0 | 0 | 0 | 0 | 0 |
| W6_5 | 0 | 0 | 0 | 0 | 0 | 0 | 0 | 0 | 0 | 0 | 0 | 0 | 0 | 0 |
| W6_60 | 96.03% | 0 | 0 | 0 | 0 | 0 | 0 | 0 | 100.00% | 0 | 0 | 99.08% | 0 | 100.00% |
| W6_6 | 0 | 0 | 0 | 0 | 0 | 0 | 0 | 0 | 15.90% | 0 | 0 | 0 | 0 | 0 |
| W6_7 | 96.03% | 0 | 0 | 0 | 0 | 0 | 0 | 0 | 100.00% | 0 | 0 | 44.24% | 0 | 88.30% |
| W6_8 | 5.63% | 0 | 0 | 0 | 0 | 0 | 0 | 0 | 62.56% | 0 | 0 | 0 | 0 | 8.05% |
| W6_9 | 96.03% | 0 | 0 | 0 | 0 | 0 | 0 | 0 | 100.00% | 0 | 0 | 99.08% | 0 | 100.00% |
| W7_10 | 96.03% | 0 | 0 | 0 | 0 | 0 | 0 | 0 | 100.00% | 0 | 0 | 99.08% | 0 | 100.00% |
| W7_11 | 96.03% | 0 | 0 | 0 | 0 | 0 | 0 | 0 | 100.00% | 0 | 0 | 55.30% | 0 | 99.25% |
| W7_12 | 11.26% | 0 | 0 | 0 | 0 | 0 | 0 | 0 | 0 | 0 | 0 | 0 | 0 | 0 |
| W7_13 | 31.13% | 0 | 0 | 0 | 0 | 0 | 0 | 0 | 63.59% | 0 | 0 | 0 | 0 | 0 |
| W7_14 | 0 | 0 | 0 | 0 | 0 | 0 | 0 | 0 | 0 | 0 | 0 | 0 | 0 | 0 |
| W7_15 | 0 | 0 | 0 | 0 | 0 | 0 | 0 | 0 | 0 | 0 | 0 | 0 | 0 | 0 |
| W7_16 | 96.03% | 0 | 0 | 0 | 0 | 0 | 0 | 0 | 100.00% | 0 | 0 | 99.08% | 0 | 100.00% |
| W7_17 | 86.75% | 0 | 0 | 0 | 0 | 0 | 0 | 0 | 75.38% | 0 | 0 | 0 | 0 | 27.42% |
| W7_18 | 96.03% | 0 | 0 | 0 | 0 | 0 | 0 | 0 | 100.00% | 0 | 0 | 99.08% | 0 | 100.00% |
| W7_19 | 0 | 0 | 0 | 0 | 0 | 0 | 0 | 0 | 0 | 0 | 0 | 0 | 0 | 0 |
| W7_20 | 71.19% | 0 | 0 | 0 | 0 | 0 | 0 | 0 | 99.49% | 0 | 0 | 34.10% | 0 | 45.53% |
| W7_21 | 96.03% | 0 | 0 | 0 | 0 | 0 | 0 | 0 | 100.00% | 0 | 0 | 82.03% | 0 | 100.00% |
| W7_22 | 0 | 0 | 0 | 0 | 0 | 0 | 0 | 0 | 0 | 0 | 0 | 0 | 0 | 0 |
| W7_25 | 96.03% | 0 | 0 | 0 | 0 | 0 | 0 | 0 | 100.00% | 0 | 0 | 99.08% | 0 | 100.00% |
| W7_26 | 96.03% | 0 | 0 | 0 | 0 | 0 | 0 | 0 | 100.00% | 0 | 0 | 99.08% | 0 | 100.00% |
| W7_27 | 0 | 0 | 0 | 0 | 0 | 0 | 0 | 0 | 0 | 0 | 0 | 0 | 0 | 0 |
| W7_28 | 0 | 0 | 0 | 0 | 0 | 0 | 0 | 0 | 0 | 0 | 0 | 0 | 0 | 0 |
| W7_29 | 0 | 0 | 0 | 0 | 0 | 0 | 0 | 0 | 0 | 0 | 0 | 0 | 0 | 0 |
| W7_2 | 0 | 0 | 0 | 0 | 0 | 0 | 0 | 0 | 0 | 0 | 0 | 0 | 0 | 0 |
| W7_30 | 0 | 0 | 0 | 0 | 0 | 0 | 0 | 0 | 0 | 0 | 0 | 0 | 0 | 0 |
| W7_31 | 0 | 0 | 0 | 0 | 0 | 0 | 0 | 0 | 0 | 0 | 0 | 0 | 0 | 0 |
| W7_32 | 0 | 0 | 0 | 0 | 0 | 0 | 0 | 0 | 0 | 0 | 0 | 0 | 0 | 0 |
| W7_33 | 0 | 0 | 0 | 0 | 0 | 0 | 0 | 0 | 0 | 0 | 0 | 0 | 0 | 0 |
| W7_34 | 0 | 0 | 0 | 0 | 0 | 0 | 0 | 0 | 0 | 0 | 0 | 0 | 0 | 0 |
| W7_35 | 96.03% | 0 | 0 | 0 | 0 | 0 | 0 | 0 | 100.00% | 0 | 0 | 99.08% | 0 | 100.00% |
| W7_36 | 96.03% | 0 | 0 | 0 | 0 | 0 | 0 | 0 | 100.00% | 0 | 0 | 61.29% | 0 | 100.00% |
| W7_37 | 96.03% | 0 | 0 | 0 | 0 | 0 | 0 | 0 | 100.00% | 0 | 0 | 99.08% | 0 | 95.85% |
| W7_38 | 0 | 0 | 0 | 0 | 0 | 0 | 0 | 0 | 0 | 0 | 0 | 0 | 0 | 0 |
| W7_3 | 0 | 0 | 0 | 0 | 0 | 0 | 0 | 0 | 0 | 0 | 0 | 0 | 0 | 0 |
| W7_41 | 94.04% | 0 | 0 | 100.00% | 0 | 0 | 0 | 0 | 70.77% | 0 | 0 | 33.18% | 0 | 28.05% |
| W7_42 | 0 | 0 | 0 | 0 | 0 | 0 | 0 | 0 | 0 | 0 | 0 | 0 | 0 | 0 |
| W7_43 | 0 | 0 | 0 | 0 | 0 | 0 | 0 | 0 | 0 | 0 | 0 | 0 | 0 | 0 |
| W7_44 | 0 | 0 | 0 | 0 | 0 | 0 | 0 | 0 | 0 | 0 | 0 | 0 | 0 | 0 |
| W7_46 | 0 | 0 | 0 | 0 | 0 | 0 | 0 | 0 | 0 | 0 | 0 | 0 | 0 | 0 |
| W7_47 | 0 | 0 | 0 | 0 | 0 | 0 | 0 | 0 | 0 | 0 | 0 | 0 | 0 | 0 |
| W7_48 | 0 | 0 | 0 | 0 | 0 | 0 | 0 | 0 | 0 | 0 | 0 | 0 | 0 | 0 |
| W7_49 | 0 | 0 | 0 | 0 | 0 | 0 | 0 | 0 | 0 | 0 | 0 | 0 | 0 | 0 |
| W7_4 | 96.03% | 0 | 0 | 0 | 0 | 0 | 0 | 0 | 100.00% | 0 | 0 | 83.41% | 0 | 98.87% |
| W7_50 | 0 | 0 | 0 | 0 | 0 | 0 | 0 | 0 | 0 | 0 | 0 | 0 | 0 | 0 |
| W7_51 | 0 | 0 | 0 | 0 | 0 | 0 | 0 | 0 | 0 | 0 | 0 | 0 | 0 | 0 |
| W7_52 | 0 | 0 | 0 | 0 | 0 | 0 | 0 | 0 | 0 | 0 | 0 | 0 | 0 | 0 |
| W7_53 | 0 | 0 | 0 | 0 | 0 | 0 | 0 | 0 | 0 | 0 | 0 | 0 | 0 | 0 |
| W7_54 | 0 | 0 | 0 | 0 | 0 | 0 | 0 | 0 | 0 | 0 | 0 | 0 | 0 | 0 |
| W7_55 | 0 | 0 | 0 | 0 | 0 | 0 | 0 | 0 | 0 | 0 | 0 | 0 | 0 | 0 |
| W7_56 | 0 | 0 | 0 | 0 | 0 | 0 | 0 | 0 | 0 | 0 | 0 | 0 | 0 | 0 |
| W7_57 | 0 | 0 | 0 | 0 | 0 | 0 | 0 | 0 | 0 | 0 | 0 | 0 | 0 | 0 |
| W7_58 | 0 | 0 | 0 | 0 | 0 | 0 | 0 | 0 | 0 | 0 | 0 | 0 | 0 | 0 |

TABLE 3-continued

Detection of transgenic components in 200 cotton varieties by low-density
liquid-phase gene chip

| Gene name | A1Bt | A2CPTI | A3CP4-epsps | A4CP4-epsps | A5bar | A6pat | A7CdP450 | A8cp4-epsps | B.1CaMV35S | B.2FMV35S | B.3NOS | B.4NOS | B.5CaMV35S | NPTII |
|---|---|---|---|---|---|---|---|---|---|---|---|---|---|---|
| W7_59 | 0 | 0 | 0 | 0 | 0 | 0 | 0 | 0 | 0 | 0 | 0 | 0 | 0 | 0 |
| W7_5 | 0 | 0 | 0 | 0 | 0 | 0 | 0 | 0 | 10.26% | 0 | 0 | 0 | 0 | 0 |
| W7_60 | 0 | 0 | 0 | 0 | 0 | 0 | 0 | 0 | 0 | 0 | 0 | 0 | 0 | 0 |
| W7_6 | 96.03% | 0 | 0 | 0 | 0 | 0 | 0 | 0 | 100.00% | 0 | 0 | 99.08% | 0 | 100.00% |
| W7_7 | 96.03% | 0 | 0 | 0 | 0 | 0 | 0 | 0 | 100.00% | 0 | 0 | 99.08% | 0 | 100.00% |
| W7_8 | 0 | 0 | 0 | 0 | 0 | 0 | 0 | 0 | 0 | 0 | 0 | 0 | 0 | 0 |
| W7_9 | 96.03% | 0 | 0 | 0 | 0 | 0 | 0 | 0 | 100.00% | 0 | 0 | 0 | 0 | 83.90% |
| W8_10 | 0 | 0 | 0 | 0 | 0 | 0 | 0 | 0 | 0 | 0 | 0 | 0 | 0 | 0 |
| W8_11 | 0 | 0 | 0 | 0 | 0 | 0 | 0 | 0 | 0 | 0 | 0 | 0 | 0 | 0 |
| W8_12 | 0 | 0 | 0 | 0 | 0 | 0 | 0 | 0 | 0 | 0 | 0 | 0 | 0 | 0 |
| W8_13 | 0 | 0 | 0 | 0 | 0 | 0 | 0 | 0 | 0 | 0 | 0 | 0 | 0 | 0 |
| W8_14 | 0 | 0 | 0 | 0 | 0 | 0 | 0 | 0 | 0 | 0 | 0 | 0 | 0 | 0 |
| W8_15 | 0 | 0 | 0 | 0 | 0 | 0 | 0 | 0 | 0 | 0 | 0 | 0 | 0 | 0 |
| W8_16 | 0 | 0 | 0 | 0 | 0 | 0 | 0 | 0 | 0 | 0 | 0 | 0 | 0 | 0 |
| W8_17 | 0 | 0 | 0 | 0 | 0 | 0 | 0 | 0 | 0 | 0 | 0 | 0 | 0 | 0 |
| W8_18 | 0 | 0 | 0 | 0 | 0 | 0 | 0 | 0 | 0 | 0 | 0 | 0 | 0 | 0 |
| W8_19 | 0 | 0 | 0 | 0 | 0 | 0 | 0 | 0 | 0 | 0 | 0 | 0 | 0 | 0 |
| W8_1 | 0 | 0 | 0 | 0 | 0 | 0 | 0 | 0 | 0 | 0 | 0 | 0 | 0 | 0 |
| W8_20 | 0 | 0 | 0 | 0 | 0 | 0 | 0 | 0 | 0 | 0 | 0 | 0 | 0 | 0 |
| W8_21 | 0 | 0 | 0 | 0 | 0 | 0 | 0 | 0 | 0 | 0 | 0 | 0 | 0 | 0 |
| W8_22 | 0 | 0 | 0 | 0 | 0 | 0 | 0 | 0 | 0 | 0 | 0 | 0 | 0 | 0 |
| W8_23 | 0 | 0 | 0 | 0 | 0 | 0 | 0 | 0 | 0 | 0 | 0 | 0 | 0 | 0 |
| W8_24 | 0 | 0 | 0 | 0 | 0 | 0 | 0 | 0 | 0 | 0 | 0 | 0 | 0 | 0 |
| W8_25 | 0 | 0 | 0 | 0 | 0 | 0 | 0 | 0 | 0 | 0 | 0 | 0 | 0 | 0 |
| W8_26 | 0 | 0 | 0 | 0 | 0 | 0 | 0 | 0 | 0 | 0 | 0 | 0 | 0 | 0 |
| W8_27 | 0 | 0 | 0 | 0 | 0 | 0 | 0 | 0 | 0 | 0 | 0 | 0 | 0 | 0 |
| W8_28 | 0 | 0 | 0 | 0 | 0 | 0 | 0 | 0 | 0 | 0 | 0 | 0 | 0 | 0 |
| W8_29 | 0 | 0 | 0 | 0 | 0 | 0 | 0 | 0 | 0 | 0 | 0 | 0 | 0 | 0 |
| W8_2 | 0 | 0 | 0 | 0 | 0 | 0 | 0 | 0 | 0 | 0 | 0 | 0 | 0 | 0 |
| W8_30 | 28.15% | 0 | 0 | 0 | 0 | 0 | 0 | 0 | 0 | 0 | 0 | 0 | 0 | 4.15% |
| W8_32 | 0 | 0 | 0 | 0 | 0 | 0 | 0 | 0 | 0 | 0 | 0 | 0 | 0 | 0 |
| W8_33 | 0 | 0 | 0 | 0 | 0 | 0 | 0 | 0 | 0 | 0 | 0 | 0 | 0 | 0 |
| W8_34 | 0 | 0 | 0 | 0 | 0 | 0 | 0 | 0 | 49.23% | 0 | 0 | 0 | 0 | 10.57% |
| W8_35 | 0 | 0 | 0 | 0 | 0 | 0 | 0 | 0 | 0 | 0 | 0 | 0 | 0 | 0 |
| W8_36 | 96.03% | 0 | 0 | 0 | 0 | 0 | 0 | 0 | 100.00% | 0 | 0 | 0 | 0 | 89.18% |
| W8_37 | 0 | 0 | 0 | 0 | 0 | 0 | 0 | 0 | 0 | 0 | 0 | 0 | 0 | 0 |
| W8_38 | 96.03% | 0 | 0 | 0 | 0 | 0 | 0 | 0 | 100.00% | 0 | 0 | 99.08% | 0 | 100.00% |
| W8_39 | 96.03% | 0 | 0 | 0 | 0 | 0 | 0 | 0 | 100.00% | 0 | 0 | 79.26% | 0 | 100.00% |
| W8_3 | 0 | 0 | 0 | 0 | 0 | 0 | 0 | 0 | 0 | 0 | 0 | 0 | 0 | 0 |
| W8_40 | 96.36% | 0 | 0 | 0 | 0 | 0 | 0 | 0 | 100.00% | 0 | 0 | 99.08% | 0 | 100.00% |
| W8_41 | 0 | 0 | 0 | 0 | 0 | 0 | 0 | 0 | 0 | 0 | 0 | 0 | 0 | 0 |
| W8_42 | 0 | 0 | 0 | 0 | 0 | 0 | 0 | 0 | 0 | 0 | 0 | 0 | 0 | 0 |
| W8_43 | 96.03% | 0 | 0 | 0 | 0 | 0 | 0 | 0 | 100.00% | 0 | 0 | 0 | 0 | 89.81% |
| W8_44 | 0 | 0 | 0 | 0 | 0 | 0 | 0 | 0 | 0 | 0 | 0 | 0 | 0 | 0 |
| W8_45 | 0 | 0 | 0 | 0 | 0 | 0 | 0 | 0 | 0 | 0 | 0 | 0 | 0 | 0 |
| W8_46 | 0 | 0 | 0 | 0 | 0 | 0 | 0 | 0 | 0 | 0 | 0 | 0 | 0 | 0 |
| W8_4 | 0 | 0 | 0 | 0 | 0 | 0 | 0 | 0 | 0 | 0 | 0 | 0 | 0 | 0 |
| W8_50 | 0 | 0 | 0 | 0 | 0 | 0 | 0 | 0 | 0 | 0 | 0 | 0 | 0 | 7.30% |
| W8_51 | 0 | 0 | 0 | 0 | 0 | 0 | 0 | 0 | 0 | 0 | 0 | 0 | 0 | 0 |
| W8_52 | 0 | 0 | 0 | 0 | 0 | 0 | 0 | 0 | 0 | 0 | 0 | 0 | 0 | 0 |
| W8_53 | 0 | 0 | 0 | 0 | 0 | 0 | 0 | 0 | 0 | 0 | 0 | 0 | 0 | 0 |
| W8_54 | 0 | 0 | 0 | 0 | 0 | 0 | 0 | 0 | 0 | 0 | 0 | 0 | 0 | 0 |
| W8_55 | 0 | 0 | 0 | 0 | 0 | 0 | 0 | 0 | 0 | 0 | 0 | 0 | 0 | 0 |
| W8_5 | 0 | 0 | 0 | 0 | 0 | 0 | 0 | 0 | 0 | 0 | 0 | 0 | 0 | 0 |
| W8_6 | 0 | 0 | 0 | 0 | 0 | 0 | 0 | 0 | 0 | 0 | 0 | 0 | 0 | 0 |
| W8_7 | 0 | 0 | 0 | 0 | 0 | 0 | 0 | 0 | 0 | 0 | 0 | 0 | 0 | 0 |
| W8_8 | 0 | 0 | 0 | 0 | 0 | 0 | 0 | 0 | 0 | 0 | 0 | 0 | 0 | 0 |
| W8_9 | 0 | 0 | 0 | 0 | 0 | 0 | 0 | 0 | 0 | 0 | 0 | 0 | 0 | 0 |

The above results confirmed that the detection rate of low-density SNP liquid-phase chip in 200 *Gossypium hirsutum* L. materials was 90.7%-96.5%, and the average locus detection rate was 94%. It has high polymorphism in *Gossypium hirsutum* L. varieties, which is very suitable for *Gossypium hirsutum* L. germplasm resource evaluation, genetic improvement and transgenic component detection with high detection accuracy. Compared with existing solid-phase chips and developed high-density liquid-phase chips, cotton breeding research can be carried out at lower costs.

Obviously, the above examples are only intended for clear explanation, rather than a limitation on the implementation. For those skilled in the art, other variations or changes in different forms can be made on the basis of the above description. It is not necessary and impossible to exhaust all the embodiments here. Nevertheless, obvious changes or variations derived therefrom still fall within the scope of protection of the present disclosure.

SEQUENCE LISTING

| SEQ ID No. | Sequence length | Sequence information | Gene name |
|---|---|---|---|
| 1 | 302 | GAAGGTTTCTA GCAATCTCTA CCAAATCTAT GCAGAGAGCT TCAGAGAGTGGGGAAGCCGAT CCTACTAACC CAGCTCTCCG CGAGGAAATG CGTATTCAATTCAACGACAT GAACAGCGCC TTGACCACAG CTATCCCATT GTTCGCAGTCCAGAACTACC AAGTTCCTCT CTTGTCCGTG TACGTTCAAG CAGCTAATCTTCACCTCAGC GTGCTTCGAG ACGTTAGCGT GTTTGGGCAA AGGTGGGGATTCGATGCTGC AACCATCAAT AGCCGTTACA ACGACCTTAC TAGGCTGATCG | A1Bt |
| 2 | 243 | GATCTGAACC ACCTCGGAAG TAATCATCAT GATGACTCAA GCGATGAACC TTCTGAGTCT TCAGAACCAT GCTGCGATTC ATGCATCTGC ACTAAATCAA TACCTCCTCA ATGCCATTGT ACAGATATCA GGTTGAATTC GTGTCACTCG GCTTGCAAAT CCTGCATGTG TACACGATCA A TGCCAGGCA AGTGTCGTTG CCTTGACA TT GCTGA TTTCT GTTACAAACC TTGCAAGTCC AGG | A2CPTI |
| 3 | 333 | ACGGTGACCG TCTTCCCGTT ACCITGCGCG GGCCGAAGAC GCCGACGCCG ATCACCTACC GCGTGCCGAT GGCCTCCGCA CAGGTGAAGT CCGCCGTGCT GCTCGCCGGC CTCAACACGC CCGGCATCAC GACGGTCATC GAGCCGATCA TGACGCGCGA TCATACGGAAAAGATGCTGC AGGGCTTTGG CGCCAACCTT ACCGTCGAGA CGGATGCGGA CGGCGTGCGC ACCATCCGCC TGGAAGGCCG CGGCAAGCTC ACCGGCCAAG TCATCGACGT GCCGGGCGAC CCGTCCTCGA CGGCCTTCCC GCTGGTTGCG GCCCTGCTTG TTC | A3CP4-epsps |
| 4 | 333 | ACGGTGATCG TCTTCCAGTT ACCTTGCGTG GACCAAAGAC TCCAACGCCA ATCACCTACA GGGTACCTAT GGCTTCCGCT CAAGTGAAGT CCGCTGTTCT GCTTGCTGGT CTCAACACCC CAGGTATCAC CACTGTTATC GAGCCAATCA TGACTCGTGA CCACACTGAA AAGATGCTTC AAGGTTTTGG TGCTAACCTT ACCGTTGAGA CTGATGCTGA CGGTGTGCGT ACCATCCGTC TTGAAGGTCG TGGTAAGCTC ACCGGTCAAG TGATTGATGT TCCAGGTGAT CCATCCTCTA CTGCTTTCCC ATTGGTTGCT GCCTTGCTTG TTC | A4CP4-epsps |
| 5 | 262 | GAAGGCACGC AACGCCTACG ACTGGACGGC CGAGTCGACC GTGTACGTCT CCCCCCGCCA CCAGCGGACG GGACTGGGCT CCACGCTCTA CACCCACCTG CTGAAGTCCC TGGAGGCACA GGGCTTCAAG AGCGTGGTCG CTGTCATCGG GCTGCCCAAC GACCCGAGCG TGCGCATGCA CGAGGCGCTC GGATATGCCC CCCGCGGCAT GCTGCGGGCG GCCGGCTTCA AGCACGGGAA CTGGCATGAC GTGGGTTTCT GG | A5bar |
| 6 | 263 | GAAGGCTAGG AACGCTTACG ATTCGACAGT TGAGAGTACT GTTTACGTGT CACATAGGCA TCAAAGGTTG GGCCTAGGAT CCACATTGTA CACACATTTG CTTAAGTCTA TGGAGGCGCA AGGTTTTAAG TCTGTGGTTG CTGTTATAGGG CCTTCCAAAC GATCCATCTG TTAGGTTGCA TGAGGCTTTG GGATACACAG CCCGGGGTAC ATTGCGCGCA GCTGGATACA AGCATGGTGG ATGGCATGAT GTTGGTTTTTGG | A6pat |
| 7 | 1551 | ATGGATAAGGCCTACGTGGCCCTCCTCTCCTTCGCCTCCCTCTTCTTGCTCCA CTACCTCGTTTCCCGCCGCAATGGCACCGGGAAGGGCAGCAAGGCCAAGGG CGCGCTGCCGCCAAGCCCTCCATCCGTTCCGTTCCTGGGCCACCTCCACCTTG TCAAGACGCCATTCCACGCTGCGCTGGCACGCCTCGCGGACTGCCACGGCCC GGTCTTCTCCCTGCGGATGGGAGCCCGCCCCGCAGTTGTGGTGTCCTCGCCG GAGCACGCCAAGGAGTGCTTCACGGAGCACGACGTGGCCTTCGCCAACCGG CCGCGCTTTCCCTCGCAGCAGCTCGCCTCCTTCAACGGTGCCGCGCTGGGTTC CGCCAGCTACGGCCCGTACTGGCGCAACCTCCGCCGCGTCGCCACCGTCCAC CTCCTGTCCGCGCACCGCGTCGCGTGCATGACGGGGACTATCGCGGCCGAGG TGCGGGCCATGGTGCGACGGATGAACCGCGCCGCGCAGGTGGCATCAGGCG GCGCGGCGCGCATCGAGCTCAAGCGGAGGCTATTTGAGGTCTCGCTCAGCGT GCTTATGGAGACCATCGCGCGGACCAAGACGTCACGTACGGAGGCGGACGA CGACACGGACATGTCGCCTGAGGCCCGGGAGTTCAAGCAGATCGTGGATGA GCTCCTGCCTCACCTCGGCACGGCTAACTTGTGGGACTACATGCCGGTGTTG CGGTGGTTCGACGTGTTCGGCGTGAGGAAGAAGATCGTGTCCGCGGTGAGG AGAAGGGACGCGTTCCTGCGGCATCTTGTCGACGCAGAGAGGACGAGGCTG GACGACGGCAACGATGCGGGCGAGAAGAAGAGCATCATTGCTATGCTGCTC ACTCTGCAGAAGTCAGAGCCGGACGTCTACTCGGATACCATGATCATGGCTC | A7CdP450 |

-continued

SEQUENCE LISTING

| SEQ ID No. | Sequence length | Sequence information | Gene name |
|---|---|---|---|
| | | TATGTGGGAACTTGTTTGGGGCCGGCACAGAGACCACGTCGACGACCACCG<br>AATGGGCCATGTCTCTCCTCCTCAACCACCCGGAGAAGCTCAGGAAGGCGCA<br>GGCTGAGATCGATGCTGTCGTGGGCACATCCCGCCTTCTTACCGCCGACGAC<br>ATGCCTCGTCTCACCTACCTCCGCTGCATCATCGACGAGACCATGCGCCTGT<br>ACCCGGCCGCACCACTTCTGCTGCCACACGAGTCCTCGACACACTGCAAGGT<br>CGGCGGCTACGACGTGCCCGCCGGCACGATGCTGCTCGTCAACGTGTACGCC<br>ATCCACAGGGACCCCGCGGTGTGGGACGGGCCGACCGAGTTCGTGCCGGAG<br>CGGTTCGAGGATGGCAAGGCAGAAGGCCGGCTGCTGATGCCGTTCGGGATG<br>GGACGGCGCAAGTGTCCCGGCGAGACGCTCGCGCTGCGGACGATCGGGCTG<br>GTGCTCGGCACGCTGATCCAGTGTTTCGACTGGGACCGGGTTGATGGTCTTG<br>AGGTCGACATGACTGAAAGTGGTGGGCTCACGATCCCCAGGGCTGTCCCGTT<br>GGAGGCCATGTGCAGGCCTCGTGCGACGATGCGTGAGGTTTTGCAGGAGCTC | |
| 8 | 1590 | ATGGCGGCGACCATGGCGTCCAACGCTGCGGCTGCGGCTGCGGTGTCCCTGG<br>ACCAGGCCGTGGCTGCGTCGGCAGCGTTCTCGTCGCGGAAGCAGCTGCGGCT<br>GCCTGCCGCAGCGCGCGGAGGGATGCGGGTGCGGGTGCGGGCGCGGGGTCG<br>GCGGGAGGCGGTGGTGGTGGCGTCCGCGTCGTCGTCGTCGGTGGCAGCGCC<br>GGCGGCGAAGGCTGAGATGCTACACGGTGCAAGCAGCCGGCCGGCAACCGC<br>TCGCAAATCTTCCGGCCTTTCGGGAACGGTCAGGATTCCGGGCGATAAGTCC<br>ATATCCCACCGGTCGTTCATGTTCGGCGGTCTTGCCAGCGGTGAGACGCGCA<br>TCACGGGCCTGCTTGAAGGTGAGGACGTGATCAATACCGGGAAGGCCATGC<br>AGGCTATGGGAGCGCGTATCCGCAAGGAAGGTGACACATGGATCATTGACG<br>GCGTTGGGAATGGCGGTCTGCTCGCCCCTGAGGCCCCTCTCGACTTCGGCAA<br>TGCGGCGACGGGCTGCAGGCTCACTATGGGACTGGTCGGGGTGTACGACTTC<br>GATAGCACGTTCATCGGAGACGCCTCGCTCACAAAGCGCCCAATGGGCCGC<br>GTTCTGAACCCGTTGCGCGAGATGGGCGTACAGGTCAAATCCGAGGATGGTG<br>ACCGTTTGCCCGTTACGCTGCGCGGGCCGAAGACGCCTACCCCGATTACCTA<br>CCGCGTGCCAATGGCATCCGCCCAGGTCAAGTCAGCCGTGCTCCTCGCCGGA<br>CTGAACACTCCGGGCATCACCACGGTGATCGAGCCCATCATGACCAGGGATC<br>ATACCGAAAAGATGCTTCAGGGGTTTGGCGCCAACCTGACGGTCGAGACGG<br>ACGCTGACGGCGTCAGGACCATCCGCCTTGAGGGCAGGGGTAAACTGACTG<br>GCCAAGTCATCGATGTTCCGGGAGACCCGTCGTCCACGGCCTTCCCGTTGGT<br>TGCGGCGCTGCTCGTGCCGGGGAGTGACGTGACCATCCTGAACGTCCTCATG<br>AACCCGACCAGGACCGGCCTGATCCTCACGCTTCAGGAGATGGGAGCCGAC<br>ATCGAGGTGATCAACCCGCGCCTGGCAGGCGGTGAAGACGTTGCGGATCTG<br>CGCGTGCGCTCCTCTACCCTGAAAGGCGTGACGGTCCCGGAAGATCGCGCGC<br>CGTCCATGATAGACGAGTATCCTATTCTGGCCGTCGCCGCTGCGTTCGCCGA<br>AGGGGCCACGGTCATGAACGGTCTTGAGGAACTCCGCGTGAAGGAATCGGA<br>TCGCCTGTCGGCGGTGGCCAATGGCCTGAAGCTCAACGGTGTTGACTGCGAC<br>GAGGGTGAGACCTCACTCGTGGTCCGTGGCCGGCCTGATGGCAAGGGCCTCG<br>GCAACGCCAGTGGAGCGGCCGTCGCCACGCACCTCGATCATCGCATCGCGAT<br>GTCCTTCTTGGTGATGGGTCTCGTCTCAGAGAACCCGGTGACCGTCGATGAC<br>GCCACGATGATAGCGACGAGCTTCCCAGAGTTCATGGATCTGATGGCGGGCC<br>TCGGGGCCAAGATCGAACTGTCTGACACGAAGGCCGCTTGA | A8cp4-<br>epsps |
| 9 | 195 | GCTCCTACAA ATGCCATCAT TGCGATAAAG GAAAGGCTAT CATTCAAGAT<br>GCCTCTGCCG ACAGTGGTCC CAAAGATGGA CCCCCACCCA CGAGGAGCAT<br>CGTGGAAAAA GAAGACGTTC CAACCACGTC TTCAAAGCAA GTGGATTGAT<br>GTGATACTTC CACTGACGTA AGGGATGACG CACAATCCCA CTATC | B.1CaM<br>V35S |
| 10 | 210 | AAGACATCCA CCGAAGACTT AAAGTTAGTG GGCATCTTTG AAAGTAATCT<br>TGTCAACATC GAGCAGCTGG CTTGTGGGGA CCAGACAAAA AAGGAATGGT<br>GCAGAATTGT TAGGCGCACC TACCAAAAGC ATCTTTGCAT TTATTGCAAA<br>GATAAAGCAG ATTCCTCTAG TACAAGTGGG GAACAAAATA ACGTGGAAAA<br>GAGCTGTCCT | B.2FMV<br>35S |
| 11 | 183 | GCCGTTTTAC GTTTGGAACT GACAGAACCG CAACGTTGAA GGAGCCACTC<br>AGCCGCGGGT TTCTGGAGTT TAATGAGCTA AGCACATACG TCAGAAACCA<br>TTATTGCGCG TTCAAAAGTC GCCTAAGGTC ACTATCAGCT AGCAAATATT<br>TCTTGTCAAA AATGCTCCAC TGACGTTCCA TAA | B.3NOS |
| 12 | 217 | ATCGTTCAAA CATTTGGCAA TAAAGTTTCT TAAGATTGAA TCCTGTTGCC<br>GGTCTTGCGA TGATTATCAT ATTAATTICTG TTGAATTACG TTAAGCATGT<br>AATAATTAAC ATIGTAATCCA TGACGTTATT TATGAGATGG GTTTTTATGA<br>TTAGAGTCCC GCAATTATAC ATTTAATACG CGATAGAAAA CAATATAG<br>CGCGCAAACT AGGATAA | B.4NOS |
| 13 | 121 | GTTTCGCTCA TGTGTTGAGC GTATAAGAAA CCCTTAGTAT GTATTTGTAT<br>TTGTAAAATA CTTCTATCAA TAAAATTTCT AATTCCTAAA ACCAAAATCC<br>AGTACTAAAA TCCAGATCCC C | B.5CaM<br>V35S |
| 14 | 795 | ATGATTGAACAAGATGGATTGCACGCAGGTTCTCCGGCCGCTTGGGTGGAGA<br>GGCTATTCGGCTATGACTGGGCACAACAGACAATCGGCTGCTCTGATGCCGC | NPTII |

SEQUENCE LISTING

```
SEQ
 ID  Sequence                                                                    Gene
No.  length     Sequence information                                             name
```

```
            CGTGTTCCGGCTGTCAGCGCAGGGGCGCCCGGTTCTTTTTGTCAAGACCGAC
            CTGTCCGGTGCCCTGAATGAACTGCAGGACGAGGCAGCGCGGCTATCGTGGC
            TGGCCACGACGGGCGTTCCTTGCGCAGCTGTGCTCGACGTTGTCACTGAAGC
            GGGAAGGGACTGGCTGCTATTGGGCGAAGTGCCGGGGCAGGATCTCCTGTC
            ATCTCACCTTGCTCCTGCCGAGAAAGTATCCATCATGGCTGATGCAATGCGG
            CGGCTGCATACGCTTGATCCGGCTACCTGCCCATTCGACCACCAAGCGAAAC
            ATCGCATCGAGCGAGCACGTACTCGGATGGAAGCCGGTCTTGTCGATCAGGA
            TGATCTGGACGAAGAGCATCAGGGGCTCGCGCCAGCCGAACTGTTCGCCAG
            GCTCAAGGCGCGCATGCCCGACGGCGATGATCTCGTCGTGACCCATGGCGAT
            GCCTGCTTGCCGAATATCATGGTGGAAAATGGCCGCTTTTCTGGATTCATCG
            ACTGTGGCCGGCTGGGTGTGGCGGACCGCTATCAGGACATAGCGTTGGCTAC
            CCGTGATATTGCTGAAGAGCTTGGCGGCGAATGGGCTGACCGCTTCCTCGTG
            CTTTACGGTATCGCCGCTCCCGATTCGCAGCGCATCGCCTTCTATCGCCTTCT
            TGACGAGTTCTTCTGA
```

What is claimed is:

1. A liquid-phase chip for *Gossypium hirsutum* L. constructed by using a targeted capture sequencing technology, wherein the liquid-phase chip is a whole genome SNP chip of *Gossypium hirsutum* L. consisting of probes for detecting 894 SNP loci and 14 major transgenes; wherein the 14 major transgenes comprise: A1Bt, referring to *Bacillus thuringiensis* gene comprising of SEQ ID NO. 15; A2CPTI, referring to Cowpea Trypsin Inhibitor comprising of SEQ ID NO. 16; A3CP4-epsps, referring to 5-enolpyruvylshikimate-3-phosphate synthase gene derived from *Agrobacterium* sp. Cp-4 and comprising of SEQ ID NO. 17; A4CP4-epsps, referring to 5-enolpyrulshikimate-3-phosphate synthase gene derived from *Agrobacterium* sp. Cp-4 2 and comprising of SEQ ID NO. 18; A5bar, referring to bialaphos resistance gene comprising of SEQ ID NO. 19; A6pat, referring to phosphinthricin acetyltransferase gene comprising of SEQ ID NO. 20; A7CdP450, referring to Cytochrome P450 comprising of SEQ ID NO. 21; A8cp4-epsps, referring to 5-enolpyruvylshikimate-3-phosphate synthase gene derived from *Agrobacterium* sp. Cp-4 and comprising of SEQ ID NO. 22; B.1CaMV35S, referring to 35S promoter from cauliflower mosaic virus comprising of SEQ ID NO. 23; B.2FMV35S, referring to 35S promoter from figwort mosaic virus comprising of SEQ ID NO. 24; B.3NOS, referring to promoter of nopaline synthase gene comprising of SEQ ID NO. 25; B.4NOS, referring to terminator of nopaline synthase gene comprising of SEQ ID NO. 26; B.5CaMV35S, referring to 35S terminator from the cauliflower mosaic virus comprising of SEQ ID NO. 27; and NPTII, referring to neomycin-3'-phosphotransferase gene comprising of SEQ ID NO. 28; and the 894 SNP loci comprises: SNP No. 001 at Genome position 110747518 of Chromosome A01 with Ref C and Alt T, which is a functional locus; SNP No. 002 at Genome position 11727109 of Chromosome A03 with Ref T and Alt C, which is a functional locus; SNP No. 003 at Genome position 20665441 of Chromosome A03 with Ref A and Alt G, which is a functional locus; SNP No. 004 at Genome position 2166240 of Chromosome A03 with Ref A and Alt G, which is a functional locus; SNP No. 005 at Genome position 22543857 of Chromosome A03 with Ref C and Alt T, which is a functional locus; SNP No. 006 at Genome position 8450966 of Chromosome A03 with Ref A and Alt T, which is a functional locus; SNP No. 007 at Genome position 766233 of Chromosome A05 with Ref C and Alt A, which is a functional locus; SNP No. 008 at Genome position 111125064 of Chromosome A10 with Ref A and Alt G, which is a functional locus; SNP No. 009 at Genome position 111437317 of Chromosome A10 with Ref G and Alt A, which is a functional locus; SNP No. 010 at Genome position 112338179 of Chromosome A10 with Ref A and Alt T, which is a functional locus; SNP No. 011 at Genome position 112651380 of Chromosome A10 with Ref T and Alt G, which is a functional locus; SNP No. 012 at Genome position 112940238 of Chromosome A10 with Ref G and Alt A, which is a functional locus; SNP No. 013 at Genome position 113053553 of Chromosome A10 with Ref G and Alt A, which is a functional locus; SNP No. 014 at Genome position 30523772 of Chromosome A11 with Ref A and Alt G, which is a functional locus; SNP No. 015 at Genome position 87529643 of Chromosome A12 with Ref A and Alt G, which is a functional locus; SNP No. 016 at Genome position 103027858 of Chromosome A13 with Ref C and Alt A, which is a functional locus; SNP No. 017 at Genome position 4110390 of Chromosome D02 with Ref T and Alt G, which is a functional locus; SNP No. 018 at Genome position 15331946 of Chromosome D03 with Ref G and Alt A, which is a functional locus; SNP No. 019 at Genome position 31088497 of Chromosome D03 with Ref C and Alt T, which is a functional locus; SNP No. 020 at Genome position 34610610 of Chromosome D03 with Ref A and Alt G, which is a functional locus; SNP No. 021 at Genome position 39193206 of Chromosome D03 with Ref C and Alt T, which is a functional locus; SNP No. 022 at Genome position 39600506 of Chromosome D03 with Ref A and Alt T, which is a functional locus; SNP No. 023 at Genome position 40070059 of Chromosome D03 with Ref G and Alt A, which is a functional locus; SNP No. 024 at Genome position 43229382 of Chromosome D03 with Ref A and Alt G, which is a functional locus; SNP No. 025 at Genome position 43511381 of Chromosome D03 with Ref A and Alt G, which is a functional locus; SNP No. 026 at Genome position 43821808 of Chromosome D03 with Ref A and Alt G, which is a functional locus; SNP No. 027 at Genome position 44126802 of Chromosome D03 with Ref T and Alt C, which is a functional locus; SNP No. 028 at Genome position 45101555 of Chromosome D03 with Ref G and Alt A, which is a functional locus; SNP No. 029 at Genome position 45114135 of Chromosome D03 with Ref A and Alt G, which is a functional locus; SNP No. 030 at Genome position 45162922 of Chromosome D03 with Ref A and Alt T, which is a functional locus; SNP No. 031 at Genome position 45219545 of Chromosome D03 with Ref C and Alt T, which is a functional locus; SNP No. 032 at Genome position 45904637 of Chromosome D03 with Ref A and Alt C, which is a functional locus; SNP No. 033 at Genome position 46030279 of Chromosome D03 with Ref A and Alt C, which is a functional locus; SNP No. 034 at Genome position 53296491 of Chromosome D04 with Ref T and Alt A, which is a functional locus; SNP No. 035 at Genome position 53338317 of Chromosome D04 with Ref A and Alt G, which is a functional locus; SNP No. 036 at Genome position 55873730 of Chromosome D04 with Ref G and Alt T, which is a functional locus; SNP No. 037 at Genome position 55895101 of Chromosome D04 with Ref A and Alt T, which is a functional locus; SNP No. 038 at Genome position 11366732 of Chromosome D06 with Ref G and Alt T, which is a functional locus; SNP No. 039 at Genome position 7626032 of Chromosome D09 with Ref T and Alt C, which is a functional locus; SNP No. 040 at Genome position 5613642 of Chromosome D10 with Ref C and Alt T, which is a functional locus; SNP No. 041 at Genome position 65188256 of Chromosome D10 with Ref T and Alt C, which is a functional locus; SNP No. 042 at Genome position 171062 of Chromosome D11 with Ref T and Alt C, which is a functional locus; SNP No. 043 at Genome position 23848335 of Chromosome D11 with Ref T and Alt C, which is a functional locus; SNP No. 044 at Genome position 23889334 of Chromosome D11 with Ref T and Alt C, which is a functional locus; SNP No. 045 at Genome position 23957256 of Chromosome D11 with Ref A and Alt T, which is a functional locus; SNP No. 046 at Genome position 24042912 of Chromosome D11 with Ref C and Alt T, which is a functional locus; SNP No. 047 at Genome position 9255660 of Chromosome D11 with Ref C and Alt T, which is a functional locus; SNP No. 048 at Genome position 4503413 of Chromosome D13 with Ref G and Alt A, which is a functional locus; SNP No. 049 at Genome position 103887986 of Chromosome A02 with Ref G and Alt A, which is a functional locus; SNP No. 050 at Genome position 103969684 of Chromosome A02 with Ref T and Alt C, which is a functional locus; SNP No. 051 at Genome position 103980780 of Chromosome A02 with Ref A and Alt G, which is a functional locus; SNP No. 052 at Genome position 7639601 of Chromosome A03 with Ref A and Alt G, which is a functional locus; SNP No. 053 at Genome position 4584038 of Chromosome A04 with Ref G and Alt A, which is a functional locus; SNP No. 054 at Genome position 4584101 of Chromosome A04 with Ref C and Alt T, which is a functional locus; SNP No. 055 at Genome position 69623179 of Chromosome A05 with Ref C and Alt T, which is a functional locus; SNP No. 056 at Genome position 28180129 of Chromosome A06 with Ref G and Alt G, which is a functional locus; SNP No. 057 at Genome position 28338559 of Chromosome A06 with Ref T and Alt G, which is a functional locus; SNP No. 058 at Genome position 28760155 of Chromosome A06 with Ref A and Alt G, which is a functional locus; SNP No. 059 at Genome position 37577336 of Chromosome A06 with Ref T and Alt C, which is a functional locus; SNP No. 060 at Genome position 10774519 of Chromosome A07 with Ref G and Alt A, which is a functional locus; SNP No. 061 at Genome position 89225727 of Chromosome A07 with Ref T and Alt C, which is a functional locus; SNP No. 062 at Genome position 90178382 of Chromosome A07 with Ref T and Alt C, which is a functional locus; SNP No. 063 at Genome position 90300535 of Chromosome A07 with Ref G and Alt T, which is a functional locus; SNP No. 064 at Genome position 90432981 of Chromosome A07 with Ref T and Alt C, which is a functional locus; SNP No. 065 at Genome position 90438470 of Chromosome A07 with Ref G and Alt A, which is a functional locus; SNP No. 066 at Genome position 90497386 of Chromosome A07 with Ref C and Alt T, which is a functional locus; SNP No. 067 at Genome position 4830640 of Chromosome A09 with Ref G and Alt A, which is a functional locus; SNP No. 068 at Genome position 77528103 of Chromosome A09 with Ref G and Alt T, which is a functional locus; SNP No. 069 at Genome position 109602998 of Chromosome A10 with Ref G and Alt A, which is a functional locus; SNP No. 070 at Genome position 112187864 of Chromosome A10 with Ref C and Alt A, which is a functional locus; SNP No. 071 at Genome position 112213784 of Chromosome A10 with Ref T and Alt C, which is a functional locus; SNP No. 072 at Genome position 75431311 of Chromosome A10 with Ref A and Alt G, which is a functional locus; SNP No. 073 at Genome position 75517245 of Chromosome A10 with Ref C and Alt G, which is a functional locus; SNP No. 074 at Genome position 7883291 of Chromosome A10 with Ref T and Alt C, which is a functional locus; SNP No. 075 at Genome position 114890178 of Chromosome A11 with Ref C and Alt T, which is a functional locus; SNP No. 076 at Genome position 15811782 of Chromosome A11 with Ref G and Alt A, which is a functional locus; SNP No. 077 at Genome position 23909944 of Chromosome A11 with Ref C and Alt, which is a functional locus; SNP No. 078 at Genome position 360614 of Chromosome A11 with Ref A and Alt C, which is a functional locus; SNP No. 079 at Genome position 90244406 of Chromosome A11 with Ref C and Alt A, which is a functional locus; SNP No. 080 at Genome position 57229716 of Chromosome A12 with Ref A and Alt G, which is a functional locus; SNP No. 081 at Genome position 88694205 of Chromosome A12 with Ref C and Alt T, which is a functional locus; SNP No. 082 at Genome position 90492050 of Chromosome A12 with Ref C and Alt T, which is a functional locus; SNP No. 083 at Genome position 98576530 of Chromosome A12 with Ref C and Alt T, which is a functional locus; SNP No. 084 at Genome position 105476632 of Chromosome A13 with Ref G and Alt T, which is a functional locus; SNP No. 085 at Genome position 105477213 of Chromosome A13 with Ref G and Alt A, which is a functional locus; SNP No. 086 at Genome position 105486165 of Chromosome A13 with Ref G and Alt A, which is a functional locus; SNP No. 087 at Genome position 105603690 of Chromosome A13 with Ref T and Alt C, which is a functional locus; SNP No. 088 at Genome position 64087028 of Chromosome D01 with Ref G and Alt C, which is a functional locus; SNP No. 089 at Genome position 1013903 of Chromosome D02 with Ref T and Alt C, which is a functional locus; SNP No. 090 at Genome position 1396386 of Chromosome D02 with Ref T and Alt C, which is a functional locus; SNP No. 091 at Genome position 43272859 of Chromosome D03 with Ref G and Alt C, which is a functional locus; SNP No. 092 at Genome position 43289074 of Chromosome D03 with Ref A and Alt T, which is a functional locus; SNP No. 093 at Genome position 23684485 of Chromosome D05 with Ref C and Alt A, which is a functional locus; SNP No. 094 at Genome position 5720265 of Chromosome D05 with Ref G and Alt T, which is a functional locus; SNP No. 095 at Genome position 57485276 of Chromosome D05 with Ref C and Alt A, which is a functional locus; SNP No. 096 at Genome position 58079007 of Chromosome D05 with Ref G and Alt A, which is a functional locus; SNP No. 097 at Genome position 58177617 of Chromosome D05 with Ref C and Alt T, which is a functional locus; SNP No. 098 at Genome position 12003138 of Chromosome D06 with Ref G and Alt A, which is a functional locus; SNP No. 099 at Genome position 17773574 of Chromosome D06 with Ref A and Alt G, which is a functional locus; SNP No. 100 at Genome position 60207647 of Chromosome D06 with Ref G and Alt C, which is a functional locus; SNP No. 101 at Genome position 8776619 of Chromosome D06 with Ref G and Alt, which is a functional locus; SNP No. 102 at Genome position 19075384 of Chromosome D07 with Ref A and Alt G, which is a functional locus; SNP No. 103 at Genome position 51856497 of Chromosome D07 with Ref T and Alt C, which is a functional locus; SNP No. 104 at Genome position 6729179 of Chromosome D07 with Ref A and Alt C, which is a functional locus; SNP No. 105 at Genome position 2896926 of Chromosome D08 with Ref A and Alt C, which is a functional locus; SNP No. 106 at Genome position 2901847 of Chromosome D08 with Ref A and Alt G, which is a functional locus; SNP No. 107 at Genome position 2904400 of Chromosome D08 with Ref A and Alt G, which is a functional locus; SNP No. 108 at Genome position 5505113 of Chromosome D08 with Ref G and Alt T, which is a functional locus; SNP No. 109 at Genome position 63065133 of Chromosome D08 with Ref G and Alt C, which is a functional locus; SNP No. 110 at Genome position 6549285 of Chromosome D09 with Ref G and Alt A, which is a functional locus; SNP No. 111 at Genome position 2524436 of Chromosome D10 with Ref C and Alt A, which is a functional locus; SNP No. 112 at Genome position 57041068 of Chromosome D11 with Ref C and Alt T, which is a functional locus; SNP No. 113 at Genome position 58261390 of Chromosome D11 with Ref A and Alt C, which is a functional locus; SNP No. 114 at Genome position 64752270 of Chromosome D11 with Ref C and Alt A, which is a functional locus; SNP No. 115 at Genome position 64756382 of Chromosome D11 with Ref T and Alt C, which is a functional locus; SNP No. 116 at Genome position 64904998 of Chromosome D11 with Ref G and Alt C, which is a functional locus; SNP No. 117 at Genome position 64926164 of Chromosome D11 with Ref C and Alt T, which is a functional locus; SNP No. 118 at Genome position 64930470 of Chromosome D11 with Ref T and Alt C, which is a functional locus; SNP No. 119 at Genome position 64937064 of Chromosome D11 with Ref G and Alt C, which is a functional locus; SNP No. 120 at Genome position 65065455 of Chromosome D11 with Ref C and Alt A, which is a functional locus; SNP No. 121 at Genome position 53158662 of Chromosome D12 with Ref G and Alt A, which is a functional locus; SNP No. 122 at Genome position 60059695 of Chromosome D12 with Ref T and Alt C, which is a functional locus; SNP No. 123 at Genome position 1774748 of Chromosome D13 with Ref C and Alt T, which is a functional locus; SNP No. 124 at Genome position 229536 of Chromosome D13 with Ref C and Alt G, which is a functional locus; SNP No. 125 at Genome position 45090184 of Chromosome D13 with Ref T and Alt G, which is a functional locus; SNP No. 126 at Genome position 53340754 of Chromosome D13 with Ref A and Alt C, which is a functional locus; SNP No. 127 at Genome position 8371110 of Chromosome D13 with Ref A and Alt C, which is a functional locus; SNP No. 128 at Genome position 39098148 of Chromosome seq1 with Ref T and Alt A, which is a functional locus; SNP No. 129 at Genome position 39098165 of Chromosome seq1 with Ref A and Alt C, which is a functional locus; SNP No. 130 at Genome position 39098173 of Chromosome seq1 with Ref G and Alt C, which is a functional locus; SNP No. 131 at Genome position 9660644 of Chromosome seq1 with Ref C and Alt G, which is a functional locus; SNP No. 132 at Genome position 2102346 of Chromosome A01 with Ref T and Alt C, which is a functional locus; SNP No. 133 at Genome position 8820452 of Chromosome A01 with Ref A and Alt C, which is a functional locus; SNP No. 134 at Genome position 1689682 of Chromosome A02 with Ref C and Alt T, which is a functional locus; SNP No. 135 at Genome position 51260473 of Chromosome A03 with Ref T and Alt A, which is a functional locus; SNP No. 136 at Genome position 6518897 of Chromosome A04 with Ref C and Alt T, which is a functional locus; SNP No. 137 at Genome position 11730945 of Chromosome A05 with Ref G and Alt A, which is a functional locus; SNP No. 138 at Genome position 75751203 of Chromosome A05 with Ref T and Alt C, which is a functional locus; SNP No. 139 at Genome position 8750649 of Chromosome A06 with Ref T and Alt C, which is a functional locus; SNP No. 140 at Genome position 1032070 of Chromosome A07 with Ref A and Alt C, which is a functional locus; SNP No. 141 at Genome position 1032071 of Chromosome A07 with Ref G and Alt T, which is a functional locus; SNP No. 142 at Genome position 12032478 of Chromosome A07 with Ref C and Alt T, which is a functional locus; SNP No. 143 at Genome position 95507309 of Chromosome A07 with Ref C and Alt G, which is a functional locus; SNP No. 144 at Genome position 989813 of Chromosome A07 with Ref T and Alt A, which is a functional locus; SNP No. 145 at Genome position 117118370 of Chromosome A08 with Ref A and Alt G, which is a functional locus; SNP No. 146 at Genome position 119190686 of Chromosome A08 with Ref T and Alt C, which is a functional locus; SNP No. 147 at Genome position 124176460 of Chromosome A08 with Ref A and Alt G, which is a functional locus; SNP No. 148 at Genome position 6187342 of Chromosome A08 with Ref T and Alt C, which is a functional locus; SNP No. 149 at Genome position 97074019 of Chromosome A08 with Ref C and Alt T, which is a functional locus; SNP No. 150 at Genome position 13706113 of Chromosome A09 with Ref T and Alt C, which is a functional locus; SNP No. 151 at Genome position 109236405 of Chromosome A10 with Ref A and Alt G, which is a functional locus; SNP No. 152 at Genome position 114220963 of Chromosome A10 with Ref C and Alt T, which is a functional locus; SNP No. 153 at Genome position 94150095 of Chromosome A12 with Ref C and Alt T, which is a functional locus; SNP No. 154 at Genome position 106412709 of Chromosome A13 with Ref C and Alt T, which is a functional locus; SNP No. 155 at Genome position 109879969 of Chromosome A13 with Ref C and Alt T, which is a functional locus; SNP No. 156 at Genome position 6433021 of Chromosome A13 with Ref T and Alt C, which is a functional locus; SNP No. 157 at Genome position 1150200 of Chromosome D01 with Ref T and Alt A, which is a functional locus; SNP No. 158 at Genome position 18933398 of Chromosome D01 with Ref C and Alt T, which is a functional locus; SNP No. 159 at Genome position 600285 of Chromosome D01 with Ref C and Alt T, which is a functional locus; SNP No. 160 at Genome position 12661527 of Chromosome D02 with Ref T and Alt C, which is a functional locus; SNP No. 161 at Genome position 1920733 of Chromosome D02 with Ref C and Alt G, which is a functional locus; SNP No. 162 at Genome position 1946913 of Chromosome D02 with Ref A and Alt G, which is a functional locus; SNP No. 163 at Genome position 44762375 of Chromosome D02 with Ref T and Alt C, which is a functional locus; SNP No. 164 at Genome position 6392666 of Chromosome D02 with Ref G and Alt A, which is a functional locus; SNP No. 165 at Genome position 68951786 of Chromosome D02 with Ref C and Alt A, which is a functional locus; SNP No. 166 at Genome position 2487227 of Chromosome D03 with Ref A and Alt G, which is a functional locus; SNP No. 167 at Genome position 1347244 of Chromosome D04 with Ref A and Alt G, which is a functional locus; SNP No. 168 at Genome position 52647897 of Chromosome D04 with Ref A and Alt G, which is a functional locus; SNP No. 169 at Genome position 26764654 of Chromosome D05 with Ref C and Alt T, which is a functional locus; SNP No. 170 at Genome position 45810951 of Chromosome D05 with Ref A and Alt G, which is a functional locus; SNP No. 171 at Genome position 1497967 of Chromosome D06 with Ref G and Alt A, which is a functional locus; SNP No. 172 at Genome position 1624645 of Chromosome D06 with Ref A and Alt C, which is a functional locus; SNP No. 173 at Genome position 54504155 of Chromosome D06 with Ref A and Alt T, which is a functional locus; SNP No. 174 at Genome position 59180787 of Chromosome D06 with Ref G and Alt A, which is a functional locus; SNP No. 175 at Genome position 61085437 of Chromosome D06 with Ref T and Alt A, which is a functional locus; SNP No. 176 at Genome position 46303166 of Chromosome D07 with Ref A and Alt G, which is a functional locus; SNP No. 177 at Genome position 61439658 of Chromosome D08 with Ref G and Alt A, which is a functional locus; SNP No. 178 at Genome position 68631323 of Chromosome D08 with Ref C and Alt T, which is a functional locus; SNP No. 179 at Genome position 9335830 of Chromosome D08 with Ref C and Alt T, which is a functional locus; SNP No. 180 at Genome position 2749569 of Chromosome D09 with Ref A and Alt C, which is a functional locus; SNP No. 181 at Genome position 38068242 of Chromosome D09 with Ref T and Alt C, which is a functional locus; SNP No. 182 at Genome position 1280801 of Chromosome D11 with Ref G and Alt A, which is a functional locus; SNP No. 183 at Genome position 15727440 of Chromosome D12 with Ref T and Alt C, which is a functional locus; SNP No. 184 at Genome position 58551591 of Chromosome D12 with Ref C and Alt T, which is a functional locus; SNP No. 185 at Genome position 7113678 of Chromosome D12 with Ref G and Alt A, which is a functional locus; SNP No. 186 at Genome position 59655465 of Chromosome D13 with Ref T and Alt G, which is a functional locus; SNP No. 187 at Genome position 60649746 of Chromosome D13 with Ref G and Alt A, which is a functional locus; SNP No. 188 at Genome position 110967771 of Chromosome A01 with Ref A and Alt C, which is a functional locus; SNP No. 189 at Genome position 107361717 of Chromosome A02 with Ref T and Alt A, which is a functional locus; SNP No. 190 at Genome position 1707434 of Chromosome A02 with Ref G and Alt A, which is a functional locus; SNP No. 191 at Genome position 26551420 of Chromosome A02 with Ref G and Alt A, which is a functional locus; SNP No. 192 at Genome position 14504864 of Chromosome A05 with Ref C and Alt T, which is a functional locus; SNP No. 193 at Genome position 14504889 of Chromosome A05 with Ref A and Alt G, which is a functional locus; SNP No. 194 at Genome position 15429410 of Chromosome A05 with Ref C and Alt G, which is a functional locus; SNP No. 195 at Genome position 42902490 of Chromosome A07 with Ref C and Alt G, which is a functional locus; SNP No. 196 at Genome position 90603512 of Chromosome A07 with Ref T and Alt G, which is a functional locus; SNP No. 197 at Genome position 90783146 of Chromosome A07 with Ref G and Alt A, which is a functional locus; SNP No. 198 at Genome position 112071927 of Chromosome A08 with Ref C and Alt T, which is a functional locus; SNP No. 199 at Genome position 110613300 of Chromosome A10 with Ref T and Alt C, which is a functional locus; SNP No. 200 at Genome position 104539963 of Chromosome A11 with Ref T and Alt C, which is a functional locus; SNP No. 201 at Genome position 1913626 of Chromosome D02 with Ref A and Alt G, which is a functional locus; SNP No. 202 at Genome position 1915388 of Chromosome D02 with Ref T and Alt C, which is a functional locus; SNP No. 203 at Genome position 6362048 of Chromosome D02 with Ref C and Alt T, which is a functional locus; SNP No. 204 at Genome position 1546736 of Chromosome D04 with Ref T and Alt A, which is a functional locus; SNP No. 205 at Genome position 14240130 of Chromosome D05 with Ref T and Alt G, which is a functional locus; SNP No. 206 at Genome position 45390691 of Chromosome D06 with Ref C and Alt T, which is a functional locus; SNP No. 207 at Genome position 46672551 of Chromosome D06 with Ref C and Alt T, which is a functional locus; SNP No. 208 at Genome position 18841330 of Chromosome D08 with Ref A and Alt C, which is a functional locus; SNP No. 209 at Genome position 20428933 of Chromosome D11 with Ref A and Alt T, which is a functional locus; SNP No. 210 at Genome position 114857126 of Chromosome A01 with Ref G and Alt A, which is a functional locus; SNP No. 211 at Genome position 115721972 of Chromosome A01 with Ref A and Alt G, which is a functional locus; SNP No. 212 at Genome position 117760175 of Chromosome A01 with Ref T and Alt C, which is a functional locus; SNP No. 213 at Genome position 117760658 of Chromosome A01 with Ref T and Alt A, which is a functional locus; SNP No. 214 at Genome position 106224475 of Chromosome A02 with Ref A and Alt G, which is a functional locus; SNP No. 215 at Genome position 3111851 of Chromosome A02 with Ref A and Alt G, which is a functional locus; SNP No. 216 at Genome position 110233891 of Chromosome A03 with Ref A and Alt G, which is a functional locus; SNP No. 217 at Genome position 67550448 of Chromosome A04 with Ref A and Alt T, which is a functional locus; SNP No. 218 at Genome position 86560855 of Chromosome A04 with Ref C and Alt T, which is a functional locus; SNP No. 219 at Genome position 86568861 of Chromosome A04 with Ref C and Alt T, which is a functional locus; SNP No. 220 at Genome position 105715349 of Chromosome A05 with Ref A and Alt G, which is a functional locus; SNP No. 221 at Genome position 15876258 of Chromosome A05 with Ref T and Alt C, which is a functional locus; SNP No. 222 at Genome position 15876308 of Chromosome A05 with Ref C and Alt G, which is a functional locus; SNP No. 223 at Genome position 1874595 of Chromosome A05 with Ref A and Alt G, which is a functional locus; SNP No. 224 at Genome position 2124121 of Chromosome A05 with Ref C and Alt T, which is a functional locus; SNP No. 225 at Genome position 22775565 of Chromosome A05 with Ref G and Alt A, which is a functional locus; SNP No. 226 at Genome position 22924264 of Chromosome A05 with Ref T and Alt A, which is a functional locus; SNP No. 227 at Genome position 22938538 of Chromosome A05 with Ref A and Alt T, which is a functional locus; SNP No. 228 at Genome position 31423050 of Chromosome A05 with Ref T and Alt C, which is a functional locus; SNP No. 229 at Genome position 119255407 of Chromosome A06 with Ref C and Alt T, which is a functional locus; SNP No. 230 at Genome position 124093748 of Chromosome A06 with Ref C and Alt T, which is a functional locus; SNP No. 231 at Genome position 1503775 of Chromosome A06 with Ref C and Alt G, which is a functional locus; SNP No. 232 at Genome position 21563371 of Chromosome A07 with Ref C and Alt T, which is a functional locus; SNP No. 233 at Genome position 23460168 of Chromosome A07 with Ref C and Alt T, which is a functional locus; SNP No. 234 at Genome position 83188617 of Chromosome A07 with Ref G and Alt C, which is a functional locus; SNP No. 235 at Genome position 88838111 of Chromosome A07 with Ref C and Alt T, which is a functional locus; SNP No. 236 at Genome position 90625054 of Chromosome A07 with Ref C and Alt T, which is a functional locus; SNP No. 237 at Genome position 90633925 of Chromosome A07 with Ref C and Alt T, which is a functional locus; SNP No. 238 at Genome position 90639206 of Chromosome A07 with Ref T and Alt C, which is a functional locus; SNP No. 239 at Genome position 104027372 of Chromosome A08 with Ref A and Alt G, which is a functional locus; SNP No. 240 at Genome position 107661059 of Chromosome A08 with Ref T and Alt G, which is a functional locus; SNP No. 241 at Genome position 123086263 of Chromosome A08 with Ref C and Alt G, which is a functional locus; SNP No. 242 at Genome position 123101111 of Chromosome A08 with Ref T and Alt C, which is a functional locus; SNP No. 243 at Genome position 31131479 of Chromosome A08 with Ref C and Alt T, which is a functional locus; SNP No. 244 at Genome position 6469161 of Chromosome A08 with Ref T and Alt A, which is a functional locus; SNP No. 245 at Genome position 73717101 of Chromosome A09 with Ref C and Alt A, which is a functional locus; SNP No. 246 at Genome position 108187386 of Chromosome A10 with Ref C and Alt T, which is a functional locus; SNP No. 247 at Genome position 114006682 of Chromosome A10 with Ref G and Alt A, which is a functional locus; SNP No. 248 at Genome position 2516523 of Chromosome A10 with Ref C and Alt T, which is a functional locus; SNP No. 249 at Genome position 4309496 of Chromosome A10 with Ref C and Alt A, which is a functional locus; SNP No. 250 at Genome position 118950829 of Chromosome A11 with Ref A and Alt T, which is a functional locus; SNP No. 251 at Genome position 24222 of Chromosome A11 with Ref G and Alt A, which is a functional locus; SNP No. 252 at Genome position 9073286 of Chromosome A11 with Ref G and Alt A, which is a functional locus; SNP No. 253 at Genome position 99926974 of Chromosome A11 with Ref A and Alt G, which is a functional locus; SNP No. 254 at Genome position 104493499 of Chromosome A12 with Ref T and Alt A, which is a functional locus; SNP No. 255 at Genome position 95983460 of Chromosome A12 with Ref C and Alt G, which is a functional locus; SNP No. 256 at Genome position 100671788 of Chromosome A13 with Ref C and Alt T, which is a functional locus; SNP No. 257 at Genome position 104864916 of Chromosome A13 with Ref T and Alt G, which is a functional locus; SNP No. 258 at Genome position 107008682 of Chromosome A13 with Ref A and Alt G, which is a functional locus; SNP No. 259 at Genome position 5759232 of Chromosome A13 with Ref A and Alt G, which is a functional locus; SNP No. 260 at Genome position 68442801 of Chromosome A13 with Ref C and Alt A, which is a functional locus; SNP No. 261 at Genome position 89442130 of Chromosome A13 with Ref G and Alt A, which is a functional locus; SNP No. 262 at Genome position 98283310 of Chromosome A13 with Ref T and Alt C, which is a functional locus; SNP No. 263 at Genome position 19034036 of Chromosome D01 with Ref T and Alt A, which is a functional locus; SNP No. 264 at Genome position 54855218 of Chromosome D01 with Ref T and Alt C, which is a functional locus; SNP No. 265 at Genome position 54866986 of Chromosome D01 with Ref C and Alt T, which is a functional locus; SNP No. 266 at Genome position 54890106 of Chromosome D01 with Ref T and Alt C, which is a functional locus; SNP No. 267 at Genome position 54896281 of Chromosome D01 with Ref G and Alt A, which is a functional locus; SNP No. 268 at Genome position 57261588 of Chromosome D01 with Ref A and Alt G, which is a functional locus; SNP No. 269 at Genome position 58881229 of Chromosome D01 with Ref C and Alt T, which is a functional locus; SNP No. 270 at Genome position 51851185 of Chromosome D02 with Ref A and Alt G, which is a functional locus; SNP No. 271 at Genome position 52987299 of Chromosome D02 with Ref A and Alt G, which is a functional locus; SNP No. 272 at Genome position 53034743 of Chromosome D02 with Ref G and Alt T, which is a functional locus; SNP No. 273 at Genome position 53253589 of Chromosome D02 with Ref A and Alt C, which is a functional locus; SNP No. 274 at Genome position 54901956 of Chromosome D02 with Ref C and Alt T, which is a functional locus; SNP No. 275 at Genome position 63310106 of Chromosome D02 with Ref T and Alt C, which is a functional locus; SNP No. 276 at Genome position 6401616 of Chromosome D02 with Ref T and Alt A, which is a functional locus; SNP No. 277 at Genome position 68030533 of Chromosome D02 with Ref A and Alt T, which is a functional locus; SNP No. 278 at Genome position 7489387 of Chromosome D02 with Ref T and Alt G, which is a functional locus; SNP No. 279 at Genome position 7531127 of Chromosome D02 with Ref A and Alt G, which is a functional locus; SNP No. 280 at Genome position 2503186 of Chromosome D03 with Ref G and Alt T, which is a functional locus; SNP No. 281 at Genome position 52350838 of Chromosome D04 with Ref T and Alt G, which is a functional locus; SNP No. 282 at Genome position 6848742 of Chromosome D04 with Ref A and Alt C, which is a functional locus; SNP No. 283 at Genome position 6861687 of Chromosome D04 with Ref C and Alt T, which is a functional locus; SNP No. 284 at Genome position 851577 of Chromosome D04 with Ref G and Alt A, which is a functional locus; SNP No. 285 at Genome position of Chromosome D05 with 14718765 Ref A and Alt G, which is a functional locus; SNP No. 286 at Genome position of Chromosome D05 with 55154526 Ref T and Alt C, which is a functional locus; SNP No. 287 at Genome position 56805649 of Chromosome D05 with Ref A and Alt G, which is a functional locus; SNP No. 288 at Genome position 18372518 of Chromosome D06 with Ref T and Alt A, which is a functional locus; SNP No. 289 at Genome position 47311286 of Chromosome D06 with Ref G and Alt T, which is a functional locus; SNP No. 290 at Genome position 64318600 of Chromosome D06 with Ref T and Alt C, which is a functional locus; SNP No. 291 at Genome position 10130687 of Chromosome D07 with Ref G and Alt C, which is a functional locus; SNP No. 292 at Genome position 54754308 of Chromosome D07 with Ref T and Alt C, which is a functional locus; SNP No. 293 at Genome position of Chromosome D07 with 54818140 Ref G and Alt A, which is a functional locus; SNP No. 294 at Genome position 54821539 of Chromosome DO7 with Ref T and Alt A, which is a functional locus; SNP No. 295 at Genome position 2748641 of Chromosome D08 with Ref C and Alt T, which is a functional locus; SNP No. 296 at Genome position 430878 of Chromosome D08 with Ref C and Alt A, which is a functional locus; SNP No. 297 at Genome position 4868113 of Chromosome D08 with Ref C and Alt T, which is a functional locus; SNP No. 298 at Genome position 608978 of Chromosome D08 with Ref C and Alt T, which is a functional locus; SNP No. 299 at Genome position 49092148 of Chromosome D09 with Ref A and Alt G, which is a functional locus; SNP No. 300 at Genome position 6069425 of Chromosome D09 with Ref C and Alt T, which is a functional locus; SNP No. 301 at Genome position 63443095 of Chromosome D10 with Ref G and Alt C, which is a functional locus; SNP No. 302 at Genome position 63918764 of Chromosome D10 with Ref C and Alt T, which is a functional locus; SNP No. 303 at Genome position 64184291 of Chromosome D10 with Ref A and Alt T, which is a functional locus; SNP No. 304 at Genome position 826050 of Chromosome D10 with Ref A and Alt G, which is a functional locus; SNP No. 305 at Genome position 10658879 of Chromosome D11 with Ref T and Alt C, which is a functional locus; SNP No. 306 at Genome position 13890576 of Chromosome D11 with Ref T and Alt C, which is a functional locus; SNP No. 307 at Genome position 21988164 of Chromosome D11 with Ref G and Alt A, which is a functional locus; SNP No. 308 at Genome position 23924389 of Chromosome D11 with Ref T and Alt A, which is a functional locus; SNP No. 309 at Genome position 23924409 of Chromosome D11 with Ref C and Alt T, which is a functional locus; SNP No. 310 at Genome position 23944152 of Chromosome D11 with Ref C and Alt T, which is a functional locus; SNP No. 311 at Genome position 24002127 of Chromosome D11 with Ref A and Alt G, which is a functional locus; SNP No. 312 at Genome position 24004889 of Chromosome D11 with Ref C and Alt T, which is a functional locus; SNP No. 313 at Genome position 24034422 of Chromosome D11 with Ref G and Alt C, which is a functional locus; SNP No. 314 at Genome position 24036519 of Chromosome D11 with Ref A and Alt G, which is a functional locus; SNP No. 315 at Genome position 3229941 of Chromosome D11 with Ref A and Alt G, which is a functional locus; SNP No. 316 at Genome position 3230659 of Chromosome D11 with Ref C and Alt T, which is a functional locus; SNP No. 317 at Genome position 62899476 of Chromosome D11 with Ref G and Alt A, which is a functional locus; SNP No. 318 at Genome position 1201966 of Chromosome D12 with Ref C and Alt A, which is a functional locus; SNP No. 319 at Genome position position 69399954 of Chromosome A01 with Ref A and Alt G, which is not a functional locus; SNP No. 361 at Genome position 72356977 of Chromosome A01 with Ref A and Alt G, which is not a functional locus; SNP No. 362 at Genome position 73066978 of Chromosome A01 with Ref C and Alt T, which is not a functional locus; SNP No. 363 at Genome position 83056539 of Chromosome A01 with Ref G and Alt C, which is not a functional locus; SNP No. 364 at Genome position 9307886 of Chromosome A01 with Ref T and Alt C, which is not a functional locus; SNP No. 365 at Genome position 94433050 of Chromosome A01 with Ref C and Alt G, which is not a functional locus; SNP No. 366 at Genome position 97114671 of Chromosome A01 with Ref G and Alt A, which is not a functional locus; SNP No. 367 at Genome position 9928461 of Chromosome A01 with Ref A and Alt G, which is not a functional locus; SNP No. 368 at Genome position 9992909 of Chromosome A01 with Ref T and Alt C, which is not a functional locus; SNP No. 369 at Genome position 104702522 of Chromosome A02 with Ref C and Alt G, which is not a functional locus; SNP No. 370 at Genome position 106564817 of Chromosome A02 with Ref G and Alt A, which is not a functional locus; SNP No. 371 at Genome position 126465 of Chromosome A02 with Ref A and Alt G, which is not a functional locus; SNP No. 372 at Genome position 18537125 of Chromosome A02 with Ref A and Alt G, which is not a functional locus; SNP No. 373 at Genome position 19418124 of Chromosome A02 with Ref T and Alt C, which is not a functional locus; SNP No. 374 at Genome position 3608260 of Chromosome A02 with Ref T and Alt A, which is not a functional locus; SNP No. 375 at Genome position 3753565 of Chromosome A02 with Ref C and Alt G, which is not a functional locus; SNP No. 376 at Genome position 39122586 of Chromosome A02 with Ref T and Alt C, which is not a functional locus; SNP No. 377 at Genome position 44761669 of Chromosome A02 with Ref C and Alt A, which is not a functional locus; SNP No. 378 at Genome position 44836527 of Chromosome A02 with Ref T and Alt C, which is not a functional locus; SNP No. 379 at Genome position 52198772 of Chromosome A02 with Ref A and Alt G, which is not a functional locus; SNP No. 380 at Genome position 63519897 of Chromosome A02 position 47819857 of Chromosome A07 with Ref A and Alt G, which is not a functional locus; SNP No. 502 at Genome position 54517045 of Chromosome A07 with Ref G and Alt A, which is not a functional locus; SNP No. 503 at Genome position 64238084 of Chromosome A07 with Ref C and Alt T, which is not a functional locus; SNP No. 504 at Genome position 80217572 of Chromosome A07 with Ref C and Alt T, which is not a functional locus; SNP No. 505 at Genome position 80388490 of Chromosome A07 with Ref A and Alt T, which is not a functional locus; SNP No. 506 at Genome position 82916184 of Chromosome A07 with Ref T and Alt C, which is not a functional locus; SNP No. 507 at Genome position 83105438 of Chromosome A07 with Ref G and Alt A, which is not a functional locus; SNP No. 508 at Genome position 8422752 of Chromosome A07 with Ref G and Alt C, which is not a functional locus; SNP No. 509 at Genome position 89161736 of Chromosome A07 with Ref A and Alt G, which is not a functional locus; SNP No. 510 at Genome position 9478030 of Chromosome A07 with Ref A and Alt C, which is not a functional locus; SNP No. 511 at Genome position 10429943 of Chromosome A08 with Ref C and Alt G, which is not a functional locus; SNP No. 512 at Genome position 106893339 of Chromosome A08 with Ref C and Alt T, which is not a functional locus; SNP No. 513 at Genome position 109696323 of Chromosome A08 with Ref G and Alt A, which is not a functional locus; SNP No. 514 at Genome position 112025642 of Chromosome A08 with Ref C and Alt T, which is not a functional locus; SNP No. 515 at Genome position 113464785 of Chromosome A08 with Ref A and Alt G, which is not a functional locus; SNP No. 516 at Genome position 116730869 of Chromosome A08 with Ref A and Alt G, which is not a functional locus; SNP No. 517 at Genome position 1713011 of Chromosome A08 with Ref T and Alt C, which is not a functional locus; SNP No. 518 at Genome position 19121855 of Chromosome A08 with Ref C and Alt A, which is not a functional locus; SNP No. 519 at Genome position 20388949 of Chromosome A08 with Ref G and Alt A, which is not a functional locus; SNP No. 520 at Genome position 25642734 of Chromosome A08 with Ref C and Alt T, which is not a functional locus; SNP No. 521 at Genome position 3134551 of Chromosome D13 with Ref A and Alt T, which is not a functional locus; SNP No. 885 at Genome position 39085839 of Chromosome D13 with Ref G and Alt A, which is not a functional locus; SNP No. 886 at Genome position 42257012 of Chromosome D13 with Ref A and Alt G, which is not a functional locus; SNP No. 887 at Genome position 49441679 of Chromosome D13 with Ref A and Alt G, which is not a functional locus; SNP No. 888 at Genome position 49745988 of Chromosome D13 with Ref A and Alt G, which is not a functional locus; SNP No. 889 at Genome position 55874078 of Chromosome D13 with Ref A and Alt G, which is not a functional locus; SNP No. 890 at Genome position 57525048 of Chromosome D13 with Ref T and Alt G, which is not a functional locus; SNP No. 891 at Genome position 58479149 of Chromosome D13 with Ref A and Alt G, which is not a functional locus; SNP No. 892 at Genome position 63605335 of Chromosome D13 with Ref A and Alt G, which is not a functional locus; SNP No. 893 at Genome position 64125386 of Chromosome D13 with Ref T and Alt C, which is not a functional locus; and SNP No. 894 at Genome position 9724970 of Chromosome D13 with Ref T and Alt A, which is not a functional locus, wherein, Ref represents base type of a SNP locus in a reference genome, and Alt represents base type of SNP locus in a population.

2. The liquid-phase chip for *Gossypium hirsutum* L. according to claim 1, wherein the probes for detecting the 14 major transgenes consist of SEQ ID NOs. 1-14.

*    *    *    *    *